United States Patent

Annoura et al.

[11] Patent Number: 6,048,876
[45] Date of Patent: *Apr. 11, 2000

[54] MEDICAMENT FOR THE ALLEVIATION OR TREATMENT OF SYMPTOM DERIVED FROM ISCHEMIC DISEASE AND COMPOUND USEFUL THEREFOR

[75] Inventors: Hirokazu Annoura, Nagaokakyo; Mayumi Uesugi, Ikoma-gun; Shinsuke Matsuki, Ibaraki; Atsuko Fukunaga, Yokohama; Toshio Tatsuoka, Nishinomiya; Shigeki Tamura, Ibaraki; Norio Inomata, Mino, all of Japan

[73] Assignee: Suntory Limited, Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/714,104

[22] PCT Filed: Jan. 23, 1996

[86] PCT No.: PCT/JP96/00119

§ 371 Date: Sep. 23, 1996

§ 102(e) Date: Sep. 23, 1996

[87] PCT Pub. No.: WO96/22977

PCT Pub. Date: Aug. 1, 1996

[30] Foreign Application Priority Data

Jan. 23, 1995 [JP] Japan .................................. 7-008241
Jan. 23, 1995 [JP] Japan .................................. 7-008403
Jan. 23, 1995 [JP] Japan .................................. 7-008470

[51] Int. Cl.[7] ...................... A61K 31/445; C07D 211/20; C07D 405/06
[52] U.S. Cl. .................. 514/317; 514/320; 546/196; 546/217; 546/236
[58] Field of Search ..................... 546/236, 217, 546/196; 514/317, 320

[56] References Cited

U.S. PATENT DOCUMENTS 4,241,071  12/1980  Martin et al. .......................... 514/278
5,110,816  5/1992  Houziaux et al. ...................... 514/255

FOREIGN PATENT DOCUMENTS

| 0 347 305 | 12/1989 | European Pat. Off. . |
|---|---|---|
| 53-95963 | 8/1978 | Japan . |
| 64-47776 | 2/1989 | Japan . |
| 2-218651 | 8/1990 | Japan . |
| 2-225464 | 9/1990 | Japan . |
| 3-505456 | 11/1991 | Japan . |
| WO93/11107 | 6/1993 | WIPO . |
| WO93/22302 | 11/1993 | WIPO . |
| WO95/03291 | 2/1995 | WIPO . |
| WO95/11238 | 4/1995 | WIPO . |
| WO95/11240 | 4/1995 | WIPO . |

OTHER PUBLICATIONS

Journal of Medicinal Chemistry, Laurence L. Martin et al., 1979, vol. 22, No. 11, pp. 1347–1354.

Foguet Ambros et al, "Improvements in the object of patent 8,702,460 regarding a 'process for preparation of new 1-[2-(phenylmethyl)phenyl]piperazines,' useful as antidepressants", *Chemical Abstracts*, 116: 106319q (1992).

Scarpelli et al. "Cell injury" p. 44, 1986.

Webster dictionary, pp. 438, 1057, 1984.

*Primary Examiner*—Ceila Chang
*Attorney, Agent, or Firm*—Burns, Doane, Swecker & Mathis, L.L.P.

[57] ABSTRACT

A medicine having the following basic structure, for the alleviation or treatment of symptoms derived from ischemic diseases and seizures, epilepsy, and migraine, having a powerful action in suppressing cytotoxic $Ca^{2+}$ overload and free from side-effects:

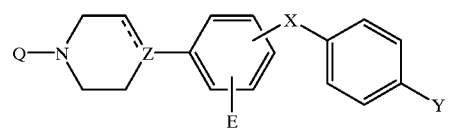

wherein Z═C, CH, or N, X═O or $CH_2$, E and Y═H, OH, a halogen, alkoxy, alkyl, or a halogen-substituted alkyl.

31 Claims, No Drawings

MEDICAMENT FOR THE ALLEVIATION OR TREATMENT OF SYMPTOM DERIVED FROM ISCHEMIC DISEASE AND COMPOUND USEFUL THEREFOR

TECHNICAL FIELD

The present invention relates to medicaments for the alleviation or treatment of symptoms based on ischemic diseases, for example, cerebral infarction, intracerebral hemorrhage, transient ischemic attack, subarachnoid hemorrhage, head trauma, after effects of brain surgery, after effects of cerebral arteriosclerosis and other cerebrovascular disorders, or variant angina, unstable angina, myocardial infarction, cardiovascular system disorders accompanying surgery for revascularization by PTCA/PTCR/CABG etc., malignant arrhythmia, and other myocardial ischemia-reperfusion injury, and further symptoms due to disorders of transplanted organs at the time of organ transplants, temporary blockage of the blood flow in organs at the time of surgery, etc. or symptoms derived from seizures, epilepsy, migraine, etc.

The present invention further relates to novel piperidine derivatives, tetrahydropyridine derivatives, piperazinodiphenylether derivatives, and piperazinodiphenylmethane derivatives useful for the alleviation or treatment of symptoms based on aforementioned ischemic diseases and intermediates for the synthesis of aforementioned compounds.

BACKGROUND ART

In cellular disorders caused by advanced ischemia, the depletion of ATP, the fall in the pH in the cells, and the destruction of the mechanism for maintenance of the energy-dependent ion homeostasis inside and outside the cell cause the accumulation of a large amount of intracellular divalent Ca ions ($Ca^{2+}$) ($Ca^{2+}$ overload). It is believed that the $Ca^{2+}$ overload causes functional disorders in the mitochondria and randomly activates various enzyme reactions and invites further $Ca^{2+}$ overload to cause a repeated vicious cycle and in the end causes irreparable damage to the cell wall and cell death [F. B. Meyer: Brain Res. Rev., 14, 227 (1989); E. Boddeke et al.: Trends Pharmacol. Sci., 10, 397 (1989)].

Medicament for suppressing cytotoxic $Ca^{2+}$ overload are considered useful for the alleviation or treatment of various ischemic diseases, for example, cerebral infarction, intracerebral hemorrhage, transient ischemic attack, subarachnoid hemorrhage, head trauma, after effects of brain surgery, after effects of cerebral arteriosclerosis and other cerebrovascular disorders, or variant angina, unstable angina, myocardial infarction, cardiovascular system disorders accompanying surgery for revascularization by PTCA/PTCR/CABG etc., malignant arrhythmia and myocardial ischemia-reperfusion injury, and further disorders of transplanted organs at the time of organ transplants and temporary blockage of the blood flow in organs at the time of surgery, however, no medicament with sufficient activity has yet been obtained.

DISCLOSURE OF INVENTION

In consideration of the state of the prior art, the objective of the present invention is to provide medicaments which have the powerful action of suppressing cytotoxic $Ca^{2+}$ overload for the alleviation and treatment without side effects of symptoms based on ischemic diseases or symptoms derived from seizures, epilepsy, migraine, etc.

Another objective of the present invention is to provide novel compounds and their salts useful as the medicaments and intermediates for synthesizing the same.

The present inventors screened compounds by evaluating the inhibitory effects on the non-L type $Ca^{2+}$ channel and $Na^+$ channel reported to be involved in the mechanism of cause of the $Ca^{2+}$ overload [P. J. Pauwels et al., Life Science, 48, 1881 (1991)].

As a result, we found that compounds of the general formula (I):

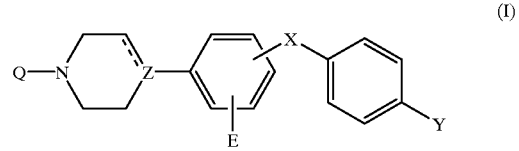

wherein, Q represents a group having the formula:

in which R represents a hydrogen atom, substituted or unsubstituted phenyl group, substituted or unsubstituted phenoxy group, or substituted or unsubstituted benzoyl group, A represents a connecting bond, a cycloalkylene group, an alkenylene group which may be substituted by a lower alkyl group, a dialkoxymethylene group, or a hydroxyiminomethylene group, and B represents an alkylene group which may be substituted by a hydroxyl group or an alkoxy group;

a group having the formula:

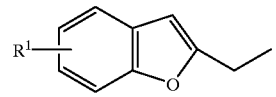

in which $R^1$ represents a hydrogen atom, a halogen atom, an alkyl group which may be substituted by a halogen atom, an alkoxy group, or a hydroxyl group; or a group having the formula:

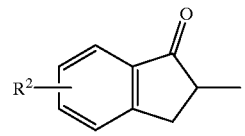

in which $R^2$ represents a hydrogen atom, a halogen atom, an alkyl group which may be substituted by a halogen atom, an alkoxy group, or a hydroxyl group;

X represents an oxygen atom or a methylene group, the substitution of X for the benzene ring being in an ortho, meta, or para position, E and Y may be the same or different from each other and represent a hydrogen atom, a hydroxyl group, a halogen atom, an alkoxy group, or an alkyl group which may be substituted by a halogen atom, the dotted line shows the presence or absence of a bond, when said dotted line shows the presence of a bond, Z represents a carbon atom, and when said dotted line shows the absence of a bond, Z represents CH or a nitrogen atom have powerful inhibitory actions on one type of the non-L type $Ca^{2+}$ channel, that is, the T-type $Ca^{2+}$ channel, and $Na^+$ channel and are effective in various types of animal disease models and thereby completed the present invention.

BEST MODE FOR CARRYING OUT THE INVENTION

Flunarizine which is used as an agent for improvement of the brain circulation [P. J. Pauwels et al.; Life Science, 48, 1881 (1991); G. E. Billman; Eur. J. Pharmacol., 212, 231 (1992)] suffers from the problem that it causes as a side effect the onset of symptoms of Parkinson's disease due to its action of blocking dopamine $D_2$ receptors. This is a major defect in its use. The compounds of the general formula (I) of the present invention, however, were found to have an extremely low affinity for the dopamine $D_2$ receptors causing the side effects of flunarizine.

In the present invention, ischemic diseases include cerebral ischemic diseases, for example, cerebral infarction, intracerebral hemorrhage, transient ischemic attack, subarachnoid hemorrhage, head trauma, after effects of brain surgery, after effects of cerebral arteriosclerosis, and other functional and organic diseases of the brain, ischemic cardiac diseases, for example, variant angina, unstable angina, myocardial infarction, cardiovascular system disorders accompanying surgery for revascularization by PTCA/PTCR/CABG etc., malignant arrhythmia and other myocardial ischemia-reperfusion injury, and also disorders of transplanted organs at the time of organ transplants, and temporary blockage of the blood flow in organs at the time of surgery.

The compounds having the general formula (I) of the present invention include compounds of the following general formulas (Ia), (Ib), (Ic), (Id), (Ie), (If), (Ig), (Ih), and (Ii).

In the general formula (Ia):

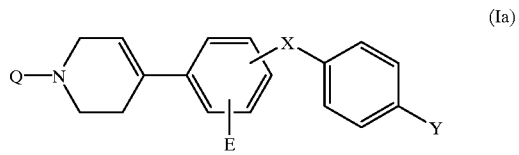

wherein, Q represents a group having the formula R—A—B—, the formula:

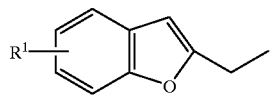

or the formula:

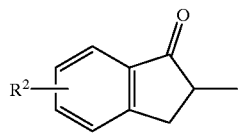

and A, B, E, R, $R^1$, $R^2$, X, and Y are as defined above, preferable examples of substituents for the substituted or unsubstituted phenyl group, substituted or unsubstituted phenoxy group, or substituted or unsubstituted benzoyl group represented by R include a halogen atom such as a fluorine atom, a chlorine atom and a bromine atom, a hydroxyl group, a $C_1$–$C_5$ alkokyl group which may be branched such as a methoxy group and an ethoxy group, and a $C_1$–$C_5$ alkyl group which may be branched and may be substituted by a halogen atom, such as a methyl group, an ethyl group and a trifluoromethyl group. Examples of a halogen atom of the $C_1$–$C_5$ alkyl group which may be branched and may be substituted by a halogen atom include a fluorine atom, a chlorine atom, and a bromine atom.

Examples of the cycloalkylene group represented by A include a 1,1-cyclopropylene group, a 1,2-cyclopropylene group, a 1,1-cyclobutylene group, a 1,1-cyclopentylene group, a 1,1-cyclohexylene group, etc., preferably a $C_3$–$C_6$ cycloalkylene group, particularly preferably a 1,1-cyclopropylene group or a 1,2-cyclopropylene group; preferable examples of the alkenylene group of the alkenylene group which may be substituted by a lower alkyl group include, preferably a $C_2$–$C_4$ alkenylene group such as a vinylene group and a butadienylene group, particularly preferably a vinylene group; preferable examples of the lower alkyl group of the alkenylene group which may be substituted by a lower alkyl group include a methyl group, ethyl group, propyl group, or isopropyl group; preferable examples of the alkoxyl group of the dialkoxymethylene group include a $C_1$–$C_5$ alkoxy group which may be branched such as a methoxy group and an ethoxy group; and, further, the dialkoxymethylene group may be a cyclic acetal such as an ethylene acetal.

Preferable examples of the alkylene group of the alkylene group which may be substituted by a hydroxyl group or an alkoxy group represented by B include preferably a $C_1$–$C_6$ alkylene group which may be branched such as a methylene group, dimethylene group, trimethylene group, tetramethylene group, methylmethylene group, propylene group, cyclopropylmethylene group, etc., particularly preferably a methylene group, dimethylene group, tetramethylene group, or cyclopropylmethylene group. Preferable examples of the alkoxy group of the alkylene group which may be substituted by an alkoxy group include a $C_1$–$C_5$ alkoxy group which may be branched, such as a methoxy group and an ethoxy group.

Preferable examples of the halogen atom represented by $R^1$ or $R^2$ include a fluorine atom, a chlorine atom, or a bromine atom; preferable examples of the alkyl group which may be substituted by a halogen include $C_1$–$C_5$ alkyl group which may be branched, such as a methyl group, an ethyl group, and a trifluoromethyl group; and preferable examples of the alkoxy group include a $C_1$–$C_5$ alkoxy group which may be branched, such as a methoxy group and an ethoxy group. Preferable examples of the halogen atom of the alkyl group which may be substituted by a halogen atom include a fluorine atom, chlorine atom, and bromine atom.

Preferable examples of the halogen atom represented by E or Y include a fluorine atom, chlorine atom, and bromine atom may be mentioned; preferable examples of the alkoxy group include a $C_1$–$C_5$ alkoxyl group which may be branched, such as a methoxy group and an ethoxy group; and preferable examples of the alkyl group which may be substituted by a halogen atom include a $C_1$–$C_5$ alkyl group which may be branched, such as a methyl group, ethyl group, trifluoromethyl group. Examples of the halogen atom of the alkyl group which may be substituted by a halogen atom include a fluorine atom, chlorine atom, and bromine atom.

When X is an oxygen atom, the substitution of X for the benzene ring is in an ortho, meta, or para position, preferably, a para position.

When X is a methylene group, the substitution of X for benzene ring is in an ortho, meta, or para position, preferably a meta or para position.

In the general formula (Ib):

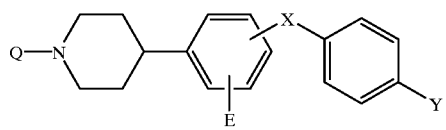

(Ib)

Q represents a group having the formula R—A—B—, the formula:

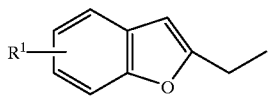

or the formula:

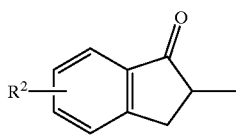

and A, B, E, R, $R^1$, $R^2$, X, and Y are as defined above, preferable examples of substituents for the substituted or unsubstituted phenyl group, substituted or unsubstituted phenoxy group, or substituted or unsubstituted benzoyl group represented by R include a halogen atom such as a fluorine atom, a chlorine atom and a bromine atom, a hydroxyl group, a $C_1$–$C_5$ alkokyl group which may be branched such as a methoxy group and an ethoxy group, and a $C_1$–$C_5$ alkyl group which may be branched and may be substituted by a halogen atom, such as a methyl group, an ethyl group and a trifluoromethyl group. Examples of a halogen atom of the $C_1$–$C_5$ alkyl group which may be branched and may be substituted by a halogen atom include a fluorine atom, a chlorine atom, and a bromine atom.

Examples of the cycloalkylene group represented by A include a 1,1-cyclopropylene group, a 1,2-cyclopropylene group, a 1,1-cyclobutylene group, a 1,1-cyclopentylene group, a 1,1-cyclohexylene group, etc., preferably a $C_3$–$C_6$ cycloalkylene group, particularly preferably a 1,1-cyclopropylene group or a 1,2-cyclopropylene group; preferable examples of the alkenylene group of the alkenylene group which may be substituted by a lower alkyl group include, preferably a $C_2$–$C_4$ alkenylene group such as a vinylene group and a butadienylene group, particularly preferably a vinylene group; preferable examples of the lower alkyl group of the alkenylene group which may be substituted by a lower alkyl group include a methyl group, ethyl group, propyl group, or isopropyl group; preferable examples of the alkoxyl group of the dialkoxymethylene group include a $C_1$–$C_5$ alkoxy group which may be branched such as a methoxy group and an ethoxy group; and, further, the dialkoxymethylene group may be a cyclic acetal such as an ethylene acetal.

Preferable examples of the alkylene group of the alkylene group which may be substituted by a hydroxyl group or an alkoxy group represented by B include preferably a $C_1$–$C_6$ alkylene group which may be branched such as a methylene group, dimethylene group, trimethylene group, tetramethylene group, methylmethylene group, propylene group, cyclopropylmethylene group, etc., particularly preferably a methylene group, dimethylene group, tetramethylene group, or cyclopropylmethylene group. Preferable examples of the alkoxy group of the alkylene group which may be substituted by an alkoxy group include a $C_1$–$C_5$ alkoxy group which may be branched, such as a methoxy group and an ethoxy group.

Preferable examples of the halogen atom represented by $R^1$ or $R^2$ include a fluorine atom, a chlorine atom, or a bromine atom; preferable examples of the alkyl group which may be substituted by a halogen include $C_1$–$C_5$ alkyl group which may be branched, such as a methyl group, an ethyl group, and a trifluoromethyl group; and preferable examples of the alkoxy group include a $C_1$–$C_5$ alkoxy group which may be branched, such as a methoxy group and an ethoxy group. Preferable examples of the halogen atom of the alkyl group which may be substituted by a halogen atom include a fluorine atom, chlorine atom, and bromine atom.

Preferable examples of the halogen atom represented by E or Y include a fluorine atom, chlorine atom, and bromine atom may be mentioned; preferable examples of the alkoxy group include a $C_1$–$C_5$ alkoxyl group which may be branched, such as a methoxy group and an ethoxy group; and preferable examples of the alkyl group which may be substituted by a halogen atom include a $C_1$–$C_5$ alkyl group which may be branched, such as a methyl group, ethyl group, trifluoromethyl group. Examples of the halogen atom of the alkyl group which may be substituted by a halogen atom include a fluorine atom, chlorine atom, and bromine atom.

When X is an oxygen atom, the substitution of X for the benzene ring is in an ortho, meta, or para position, preferably a para position.

When X is a methylene group, the substitution of X for the benzene ring is in an ortho, meta, or para position, preferably a meta or para position.

In the general formula (Ic):

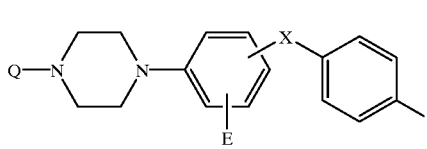

(Ic)

Q represents a group of the formula R—A—B—, the formula:

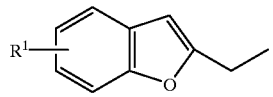

or the formula:

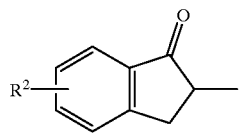

and A, B, E, R, $R^1$, $R^2$, X, and Y are as defined above, preferable examples of substituents for the substituted or unsubstituted phenyl group, substituted or unsubstituted phenoxy group, or substituted or unsubstituted benzoyl group represented by R include a halogen atom such as a fluorine atom, a chlorine atom and a bromine atom, a hydroxyl group, a $C_1$–$C_5$ alkokyl group which may be branched such as a methoxy group and an ethoxy group, and a $C_1$–$C_5$ alkyl group which may be branched and may be substituted by a halogen atom, such as a methyl group, an ethyl group and a trifluoromethyl group. Examples of a halogen atom of the $C_1$–$C_5$ alkyl group which may be branched and may be substituted by a halogen atom include a fluorine atom, a chlorine atom, and a bromine atom.

Examples of the cycloalkylene group represented by A include a 1,1-cyclopropylene group, a 1,2-cyclopropylene group, a 1,1-cyclobutylene group, a 1,1-cyclopentylene group, a 1,1-cyclohexylene group, etc., preferably a $C_3$–$C_6$ cycloalkylene group, particularly preferably a 1,1-cyclopropylene group or a 1,2-cyclopropylene group; preferable examples of the alkenylene group of the alkenylene group which may be substituted by a lower alkyl group include, preferably a $C_2$–$C_4$ alkenylene group such as a vinylene group and a butadienylene group, particularly preferably a vinylene group; preferable examples of the lower alkyl group of the alkenylene group which may be substituted by a lower alkyl group include a methyl group, ethyl group, propyl group, or isopropyl group; preferable examples of the alkoxyl group of the dialkoxymethylene group include a $C_1$–$C_5$ alkoxy group which may be branched such as a methoxy group and an ethoxy group; and, further, the dialkoxymethylene group may be a cyclic acetal such as an ethylene acetal.

Preferable examples of the alkylene group of the alkylene group which may be substituted by a hydroxyl group or an alkoxy group represented by B include preferably a $C_1$–$C_6$ alkylene group which may be branched such as a methylene group, dimethylene group, trimethylene group, tetramethylene group, methylmethylene group, propylene group, cyclopropylmethylene group, etc., particularly preferably a methylene group, dimethylene group, tetramethylene group, or cyclopropylmethylene group. Preferable examples of the alkoxy group of the alkylene group which may be substituted by an alkoxy group include a $C_1$–$C_5$ alkoxy group which may be branched, such as a methoxy group and an ethoxy group.

Preferable examples of the halogen atom represented by $R^1$ or $R^2$ include a fluorine atom, a chlorine atom, or a bromine atom; preferable examples of the alkyl group which may be substituted by a halogen include $C_1$–$C_5$ alkyl group which may be branched, such as a methyl group, an ethyl group, and a trifluoromethyl group; and preferable examples of the alkoxy group include a $C_1$–$C_5$ alkoxy group which may be branched, such as a methoxy group and an ethoxy group. Preferable examples of the halogen atom of the alkyl group which may be substituted by a halogen atom include a fluorine atom, chlorine atom, and bromine atom.

Preferable examples of the halogen atom represented by E or Y include a fluorine atom, chlorine atom, and bromine atom may be mentioned; preferable examples of the alkoxy group include a $C_1$–$C_5$ alkoxyl group which may be branched, such as a methoxy group and an ethoxy group; and preferable examples of the alkyl group which may be substituted by a halogen atom include a $C_1$–$C_5$ alkyl group which may be branched, such as a methyl group, ethyl group, trifluoromethyl group. Examples of the halogen atom of the alkyl group which may be substituted by a halogen atom include a fluorine atom, chlorine atom, and bromine atom.

The substitution of X for the benzene ring may be in an ortho, meta, or para position, preferably a meta or para position.

In the general formula (Id):

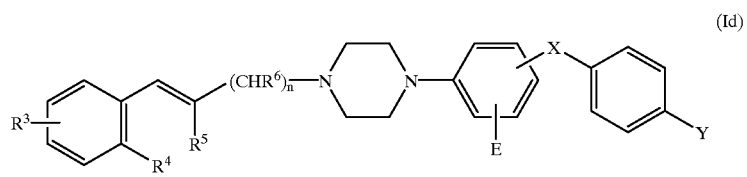

$R^3$ represents a hydrogen atom, a halogen atom, an alkyl group which may be substituted by a halogen atom, an alkoxy group, or a hydroxyl group, $R^4$ and $R^5$ are the same or different from each other and represent a hydrogen atom or a lower alkyl group, or $R^4$ and $R^5$ are taken together to represent —O—, $R^6$ represents a hydrogen atom, a hydroxyl group, an alkoxy group, or an alkyl group, n is an integer of 1 to 6, and E, X, and Y are as defined above, preferable examples of the halogen atom represented by $R^3$ include a fluorine atom, a chlorine atom and a bromine atom; preferable examples of the alkyl group which may be substituted by a halogen atom include a $C_1$–$C_5$ alkyl group which may be branched such as a methyl group, an ethyl group and a trifluoromethyl group; and preferable examples of the alkoxy group include a $C_1$–$C_5$ alkoxy group which may be branched such as a methoxy group and an ethoxy group. Examples of the halogen atom of the alkyl group which may be substituted by a halogen atom include a fluorine atom, a chlorine atom, and a bromine atom. Examples of the lower alkyl group represented by $R^4$ or $R^5$ include a methyl group, an ethyl group, a propyl group, and an isopropyl group. Preferable examples of the alkoxyl group represented by $R^6$ include a $C_1$–$C_5$ alkoxyl group which may be branched such as a methoxy group and an ethoxy group; and preferable examples of the alkyl group include a $C_1$–$C_5$ alkyl group which may be branched such as a methyl group, an ethyl group, and a propyl group.

Preferable examples of the integer shown by n include 1, 2, and 3.

When X is an oxygen atom, the substitution of X for the benzene ring is in an ortho, meta, or para position, preferably a para position.

When X is a methylene group, the substitution of x for the benzene ring is in an ortho, meta, or para position, preferably a meta or para position.

In the general formula (Ie):

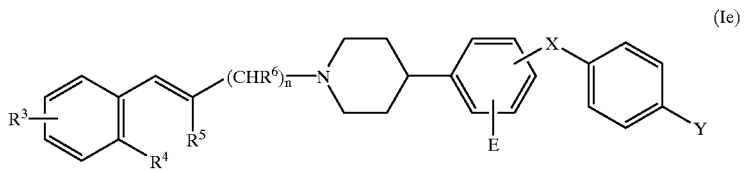

(Ie)

E, $R^3$, $R^4$, $R^5$, $R^6$, X, Y, and n are as defined above, preferable examples of the halogen atom represented by $R^3$ include a fluorine atom, a chlorine atom and a bromine atom; preferable examples of the alkyl group which may be substituted by a halogen atom include a $C_1$–$C_5$ alkyl group which may be branched such as a methyl group, an ethyl group and a trifluoromethyl group; and preferable examples of the alkoxyl group include a $C_1$–$C_5$ alkoxy group which may be branched such as a methoxy group and an ethoxy group. Examples of the halogen atom of the alkyl group which may be substituted by a halogen atom include a fluorine atom, a chlorine atom, and a bromine atom. Examples of the lower alkyl group represented by $R^4$ or $R^5$ include a methyl group, an ethyl group, a propyl group, and an isopropyl group. Preferable examples of the alkoxyl group represented by $R^6$ include a $C_1$–$C_5$ alkoxyl group which may be branched such as a methoxy group and an ethoxy group; and preferable examples of the alkyl group include a $C_1$–$C_5$ alkyl group which may be branched such as a methyl group, an ethyl group, and a propyl group.

Preferable examples of the integer shown by n include 1, 2, and 3.

When X is an oxygen atom, the substitution of X for the benzene ring is in an ortho, meta, or para position, preferably a para position.

When X is a methylene group, the substitution of X for the benzene ring is in an ortho, meta, or para position, preferably a meta or para position.

In the general formula (If):

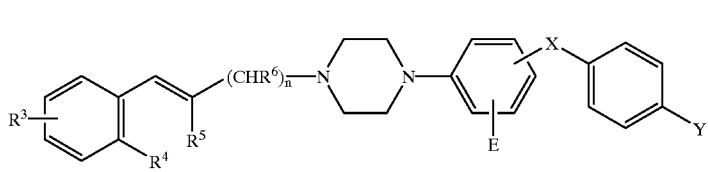

(If)

E, $R^3$, $R^4$, $R^5$, $R^6$, X, Y, and n are as defined above, preferable examples of the halogen atom represented by $R^3$ include a fluorine atom, a chlorine atom and a bromine atom; preferable examples of the alkyl group which may be substituted by a halogen atom include a $C_1$–$C_5$ alkyl group which may be branched such as a methyl group, an ethyl group and a trifluoromethyl group; and preferable examples of the alkoxyl group include a $C_1$–$C_5$ alkoxy group which may be branched such as a methoxy group and an ethoxy group. Examples of the halogen atom of the alkyl group which may be substituted by a halogen atom include a fluorine atom, a chlorine atom, and a bromine atom. Examples of the lower alkyl group represented by $R^4$ or $R^5$ include a methyl group, an ethyl group, a propyl group, and an isopropyl group. Preferable examples of the alkoxyl group represented by $R^6$ include a $C_1$–$C_5$ alkoxyl group which may be branched such as a methoxy group and an ethoxy group; and preferable examples of the alkyl group include a $C_1$–$C_5$ alkyl group which may be branched such as a methyl group, an ethyl group, and a propyl group.

Preferable examples of the integer shown by n include 1, 2, and 3.

The substitution of X for the benzene ring is in an ortho, meta, or para position, preferably a meta or para position.

In the general formula (Ig):

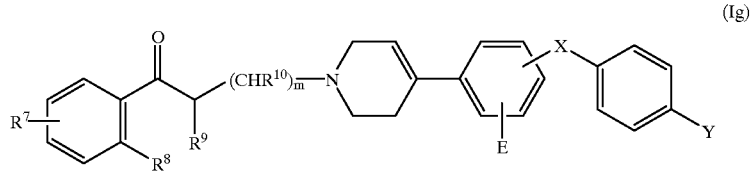

(Ig)

$R^7$ represents a hydrogen atom, a halogen atom, an alkyl group which may be substituted by a halogen atom, an alkoxy group, or a hydroxyl group, $R^8$ and $R^9$ are the same or different from each other and represent a hydrogen atom, or an alkyl group, or $R^8$ and $R^9$ are taken together to represent a methylene group, $R^{10}$ represents a hydrogen atom, a hydroxyl group, an alkoxy group or an alkyl group, m is an integer from 0 to 6, and E, X and Y are as defined above, preferable examples of the halogen atom represented by $R^7$ include a fluorine atom, a chlorine atom, and a bromine atom; preferable examples of the alkyl group which may be substituted by a halogen atom include a $C_1$–$C_5$ alkyl group which may be branched such as a methyl group, an ethyl group and a trifluoromethyl group; and preferable examples of the alkoxyl group include a $C_1$–$C_5$ alkoxy group which may be branched such as a methoxy group, and an ethoxy group. Examples of the halogen atom of the alkyl group which may be substituted by a halogen atom include a fluorine atom, a chlorine atom, and a bromine atom. Preferable examples of the alkyl group represented by $R^8$ or $R^9$ include a $C_1$–$C_5$ alkyl group which may be branched such as a methyl group, an ethyl group, and a propyl group. Preferable examples of the alkoxy group represented by $R^{10}$ include a $C_1$–$C_5$ alkoxy group which may be branched such as a methoxy group and an ethoxy group; and preferable examples of the alkyl group include a $C_1$–$C_5$ alkyl group which may be branched such as a methyl group, an ethyl group, and a propyl group.

Preferable examples of the integer of 0 to 6 shown by m include 0, 1, 2, 3, and 4.

When X is an oxygen atom, the substitution of X for the benzene ring is in an ortho, meta, or para position, preferably a para position.

When X is a methylene group, the substitution of X for the benzene ring is in an ortho, meta or para position, preferably a meta or para position.

In the general formula (Ih):

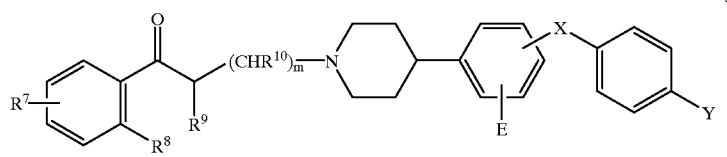

(Ih)

E, $R^7$, $R^8$, $R^9$, $R^{10}$, X, Y and m are as defined above, preferable examples of the halogen atom represented by $R^7$ include a fluorine atom, a chlorine atom, and a bromine atom; preferable examples of the alkyl group which may be substituted by a halogen atom include a $C_1$–$C_5$ alkyl group which may be branched such as a methyl group, an ethyl group and a trifluoromethyl group; and preferable examples of the alkoxyl group include a $C_1$–$C_5$ alkoxy group which may be branched such as a methoxy group, and an ethoxy group. Examples of the halogen atom of the alkyl group which may be substituted by a halogen atom include a fluorine atom, a chlorine atom, and a bromine atom. Preferable examples of the alkyl group represented by $R^8$ or $R^9$ include a $C_1$–$C_5$ alkyl group which may be branched such as a methyl group, an ethyl group, and a propyl group. Preferable examples of the alkoxy group represented by $R^{10}$ include a $C_1$–$C_5$ alkoxy group which may be branched such as a methoxy group and an ethoxy group; and preferable examples of the alkyl group include a $C_1$–$C_5$ alkyl group which may be branched such as a methyl group, an ethyl group, and a propyl group.

Preferable examples of the integer of 0 to 6 shown by m include 0, 1, 2, 3, and 4.

When X is an oxygen atom, the substitution of X for the benzene ring is in an ortho, meta or para position, preferably a para position.

When X is a methylene group, the substitution of X for the benzene ring is in an ortho, meta, or para position, preferably a meta or para position.

In the general formula (Ii):

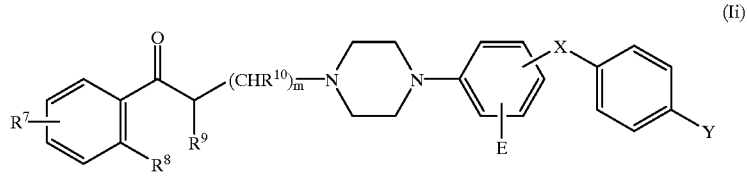

(Ii)

E, $R^7$, $R^8$, $R^9$, $R^{10}$, X, Y and m are as defined above, preferable examples of the halogen atom represented by $R^7$ include a fluorine atom, a chlorine atom, and a bromine atom; preferable examples of the alkyl group which may be substituted by a halogen atom include a $C_1$–$C_5$ alkyl group which may be branched such as a methyl group, an ethyl group and a trifluoromethyl group; and preferable examples of the alkoxyl group include a $C_1$–$C_5$ alkoxy group which may be branched such as a methoxy group, and an ethoxy group. Examples of the halogen atom of the alkyl group which may be substituted by a halogen atom include a fluorine atom, a chlorine atom, and a bromine atom. Preferable examples of the alkyl group represented by $R^8$ or $R^9$ include a $C_1$–$C_5$ alkyl group which may be branched such as a methyl group, an ethyl group, and a propyl group. Preferable examples of the alkoxy group represented by $R^{10}$ include a $C_1$–$C_5$ alkoxy group which may be branched such as a methoxy group and an ethoxy group; and preferable examples of the alkyl group include a $C_1$–$C_5$ alkyl group which may be branched such as a methyl group, an ethyl group, and a propyl group.

Preferable examples of the integer of 0 to 6 shown by m include 0, 1, 2, 3, and 4.

The substitution of X for the benzene ring is in an ortho, meta, or para position, preferably a meta or para position.

Among the compounds represented by the general formula (I), particularly preferable compounds are as follows:

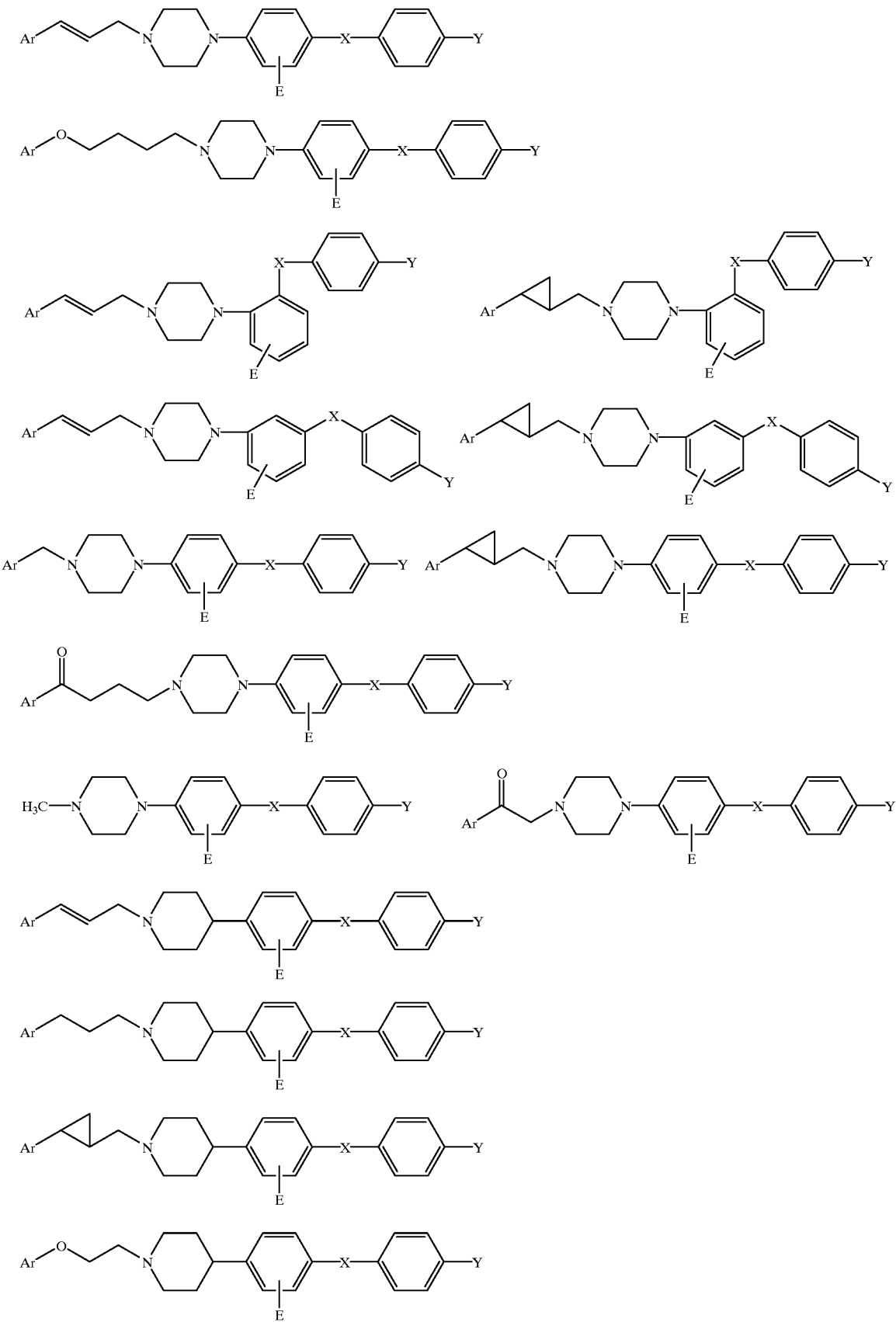

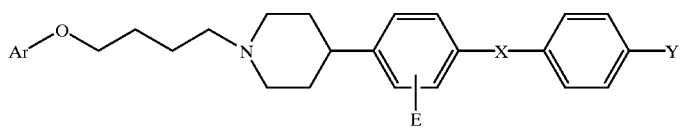
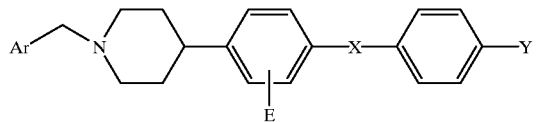
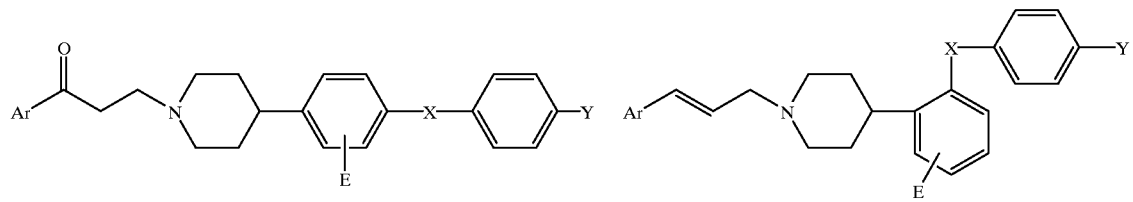
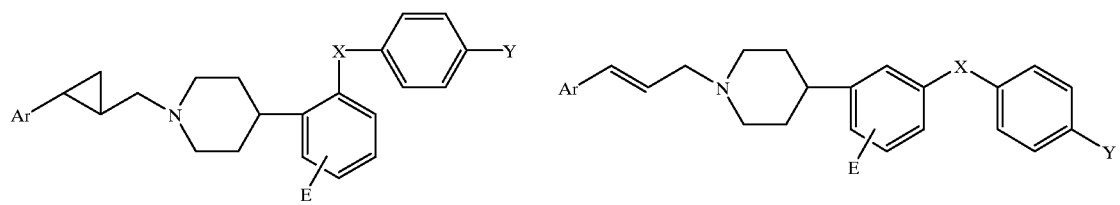
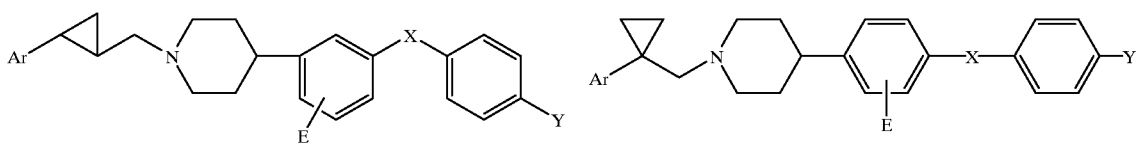
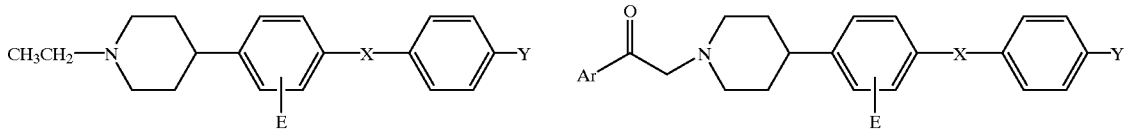
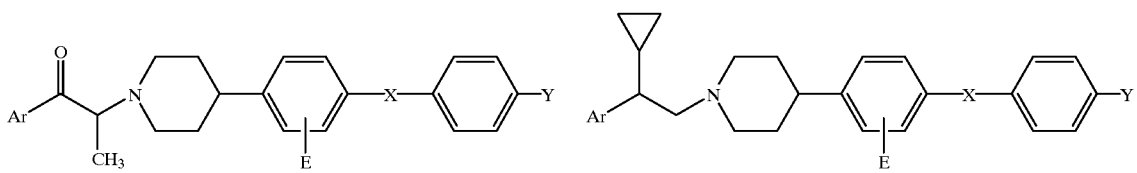
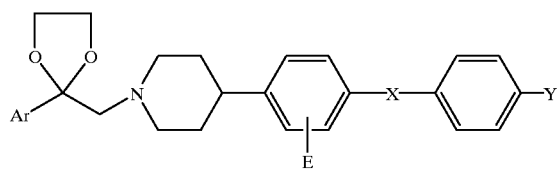
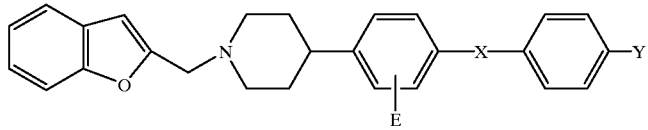
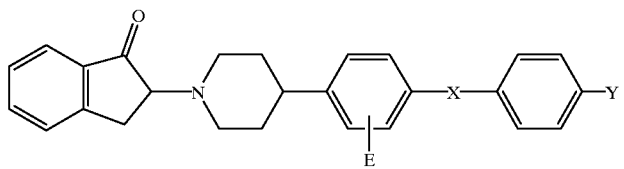

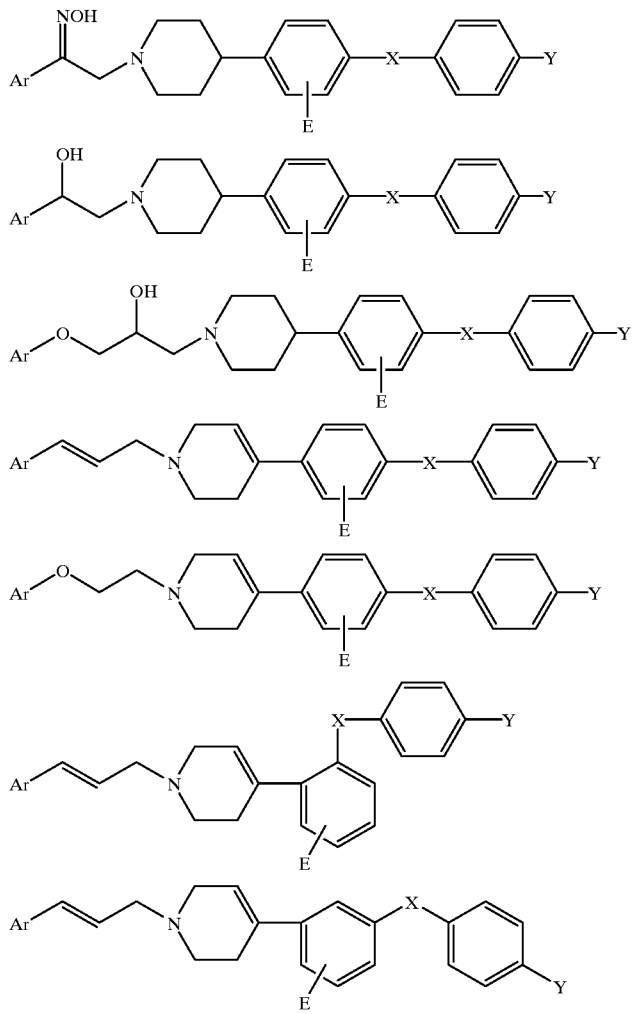

wherein, Ar represents a phenyl group and E, X, and Y are as defined above.

Further, the present invention provides compounds having the general formula (I') and their salts:

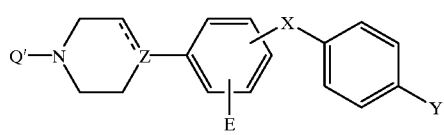

(I')

wherein, Q' represents a group having the formula:

R'—A—B— in which R' represents a substituted or unsubstituted phenyl group, a substituted or unsubsituted phenoxy group, or substituted or unsubstituted benzoyl group, A represents a connecting bond, a cycloalkylene group, an alkenylene group which may be substituted by a lower alkyl group, a dialkoxymethylene group, or a hydroxyiminomethylene group, and B represents an alkylene group which may be substituted by a hydroxy group or an alkoxy group;

a group having the formula:

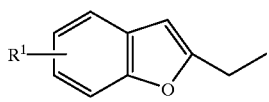

in which $R^1$ represents a hydrogen atom, a halogen atom, an alkyl group which may be substituted by a halogen atom, an alkoxy group, or a hydroxyl group; or a group having the formula:

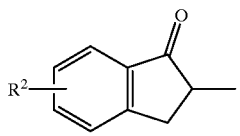

in which $R^2$ represents a hydrogen atom, a halogen atom, an alkyl group which may be substituted by a halogen atom, an alkoxy group, or a hydroxyl group, X represents an oxygen atom or a methylene group, the substitution of X for the benzene ring is in an ortho, meta, or para position, E and Y may be the same or different from each oher and represent a hydrogen atom, a hydroxyl group, a halogen atom, an alkoxy group, or an alkyl group which may be substituted by a halogen atom, the dotted line shows the presence or absence of a bond, when said dotted line shows the presence of a bond, Z represents a carbon atom, when said dotted line shows the absence of a bond, Z represents CH or a nitrogen atom, when Z is a carbon atom or CH, X is a methylene group, A is a connecting bond, and B is an unsubstituted alkylene group, R' does not represent an unsubstituted phenyl group.

Preferable examples of substituent for the substituted or unsubstituted phenyl group, substituted or unsubstituted phenoxy group or substituted or unsubstituted benzoyl group represented by R' include a halogen atom such as a fluorine atom, a chlorine atom, and a bromine atom, a hydroxyl group, a $C_1$–$C_5$ alkoxy group which may be branched such as a methoxy group and an ethoxy group, a $C_1$–$C_5$ alkyl group which may be branched and may be substituted by a halogen atom such as a methyl group, an ethyl group and a trifluoromethyl group. Examples of the halogen atom of the $C_1$–$C_5$ alkyl group which may be branched and may be substituted by a halogen atom include a fluorine atom, a chlorine atom, and a bromine atom.

The preferable examples of the cycloalkylene group, the alkenylene group which may be substituted by a lower alkyl group, or the dialkoxymethylene group represented by A, preferable examples of the alkylene group which may be substituted by a hydroxyl group or an alkoxy group represented by B, preferable examples of the halogen atom, the alkoxy group, or the alkyl group which may be substituted by a halogen atom represented by E or Y, and preferable examples of the halogen atom, the alkyl group which may be substituted by a halogen atom, and the alkoxy group represented by $R^1$ or $R^2$ are the same as with A, B, E, Y, $R^1$ and $R^2$ in the above general formula (I).

The present invention further provides compounds having the general formula (I″) and their salts:

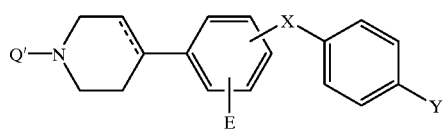

(I″)

wherein, Q' represents a group having the formula:

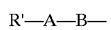

R'—A—B— in which R' represents a substitued or unsubstituted phenyl group, substituted or unsubstituted phenoxy group, or substituted or unsubstituted benzoyl group, A represents a connecting bond, a cycloalkylene group, an alkenylene group which may be substituted by a lower alkyl group, a dialkoxymethylene group, or a hydroxyiminomethylene group, and B represents a hydroxyl group- or alkoxyl group-substitutable an alkylene group which may be substituted by a hydroxyl group or an alkoxy group;

a group having the formula:

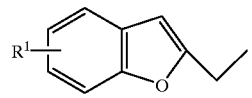

in which $R^1$ represents a hydrogen atom, a halogen atom, an alkyl group which may be substituted by a halogen atom, an alkoxy group, or a hydroxyl group; or a group having the formula:

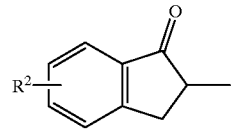

in which $R^2$ represents a hydrogen atom, a halogen atom, an alkyl group which may be substituted by a halogen atom, an alkoxy group, or a hydroxyl group, X represents an oxygen atom or a methylene group, the substitution of X for the benzene ring is in an ortho, meta, or para position, E and Y may be the same or different from each other and represent a hydrogen atom, a hydroxyl group, a halogen atom, an alkoxy group, or an alkyl group which may be substituted by a halogen atom, the dotted line shows the presence or absence of a bond, and when X is a methylene group, A is a connecting bond and B is an unsubstituted alkylene group, R' does not represent an unsubstituted phenyl group.

The preferable examples of the substituent of the substituted or unsubstituted phenyl group, substituted or unsubstituted phenoxy group, or substituted or unsubstituted benzoyl group represented by R', preferable examples of the cycloalkylene group, the alkenylene group which may be substituted by a lower alkyl group or the dialkoxymethylene group represented by A, preferable examples of the alkylene group which may be substituted by a hydroxyl group or an alkoxy group represented by B, preferable examples of the halogen atom, the alkoxy group, or the alkyl group which may be substituted by a halogen atom represented by E or Y, and preferable examples of the halogen atom, the alkyl group which may be substituted by a halogen atom, and the alkoxyl group represented by $R^1$ or $R^2$ are the same as with R', A, B, E, Y, $R^1$ and $R^2$ in the above general formula (I').

The compounds having the general formula (I″) include the compounds having the general formulas (I″a) and (I″b).

In the general formula (I″a):

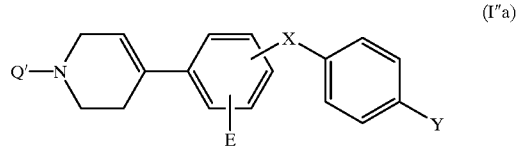

(I″a)

wherein, Q', E, X, and Y are as defined above.

In the general formula (I″b):

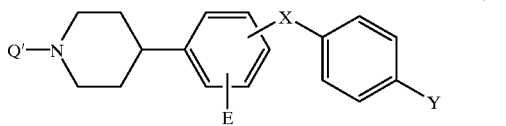
(I″b)

wherein, Q', E, X, and Y are as defined above.

The present invention further provides compounds having the general formula (I‴) and their salts:

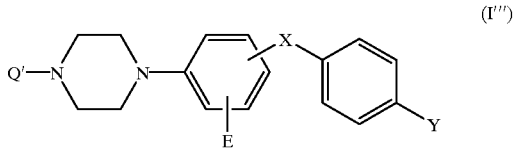
(I‴)

wherein, Q' represents a group having the formula:

R'—A—B— in which R' represents a substituted or unsubstituted phenyl group, substituted or unsubstituted phenoxy group, or substituted or unsubstituted benzoyl group, A represents a connecting bond, a cycloalkylene group, an alkenylene group which may be substituted by a lower alkyl group, a dialkoxymethylene group, or a hydroxyiminomethylene group, and B represents an alkylene group which may be substituted by a hydroxy group or an alkoxy group;

a group having the formula:

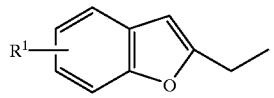

in which $R^1$ represents a hydrogen atom, a halogen atom, an alkyl group which may be substituted by a halogen atom, an alkoxyl group, or a hydroxyl group; or a group having the formula:

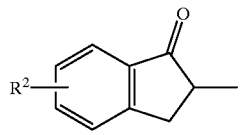

in which $R^2$ represents a hydrogen atom, a halogen atom, an alkyl group which may be substituted by a halogen atom, an alkoxy group, or a hydroxyl group, X represents an oxygen atom or methylene group, the substitution of X for the benzene ring is in an ortho, meta, or para position, and E and Y may be the same or different from each other and represent a hydrogen atom, a hydroxyl group, a halogen atom, an alkoxy group, or an alkyl group which may be substituted by a halogen atom-substitutable alkyl group.

The examples of the preferable substituent for the substituted or unsubstituted phenyl group, substituted or unsubstituted phenoxy group, or substituted or unsubstituted benzoyl group represented by R', preferable examples of the cycloalkylene group, the alkenylene group which may be substituted by a lower alkyl group, or the dialkoxymethylene group represented by A, preferable examples of the alkylene group which may be substituted by a hydroxyl group or alkoxyl group represented by B, preferable examples of the halogen atom, the alkoxy group, or the alkyl group which may be substituted by a halogen atom represented by E or Y and preferable examples of the halogen atom, the alkyl group which may be substituted by a halogen atom, or an alkoxy group represented by $R^1$ or $R^2$ are the same as with R', A, B, E, Y, $R^1$ and $R^2$ in the above general formula (I').

The compounds having the general formulas (I), (I'), (I″), and (I‴) of the present invention include isomers. The present invention includes all of these isomers and mixtures of the same. For example, in the general formulas (I), (I'), (I″) and (I‴), when B represents an alkylene group which may be substituted by a hydroxyl group or an alkoxyl group, there are two optical isomers, when A represents a hydroxyiminomethylene group and an alkenylene group which may be substituted by a lower alkyl group, there are two geometric isomers, (E)-form and (Z)-form. The compounds of the present invention include the individual isomers and all mixtures of combinations of the same.

According to the present invention, further, there are provided compounds of the general formula (IIa):

In the general formula (IIa):

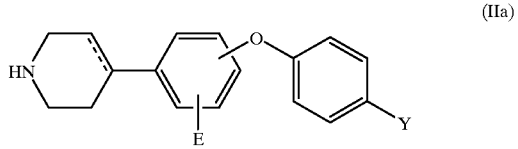
(IIa)

wherein, E and Y may be the same or different from each other and represent a hydrogen atom, a hydroxyl group, a halogen atom, an alkoxy group, or an alkyl group which may be substituted by a halogen atom, the dotted line shows the presence or absence of a bond, and the substitution of the benzene ring bonding with the piperidine ring or tetrahydropyridine ring and the group —$OC_6H_4Y$ is in an ortho, meta, or para position.

According to the present invention, further, there are provided compounds having the general formula (IIb):

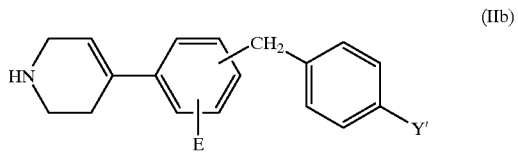
(IIb)

wherein, E represents a hydrogen atom, hydroxyl group, a halogen atom, an alkoxy group, or an alkyl group which may be substituted by a halogen atom, Y' represents a hydroxyl group, a halogen atom, an alkoxy group, or an alkyl group which may be substituted by a halogen atom, and the substitution of the benzene ring bonding with the tetrahydropyridine ring and group —$CH_2C_6H_4Y'$ is in an ortho, meta, or para position.

According to the present invention, further, there are provided compounds having the general formula (IIc):

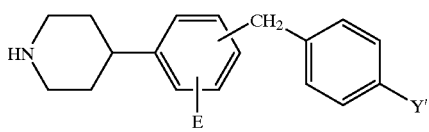

(IIc)

wherein, E represents a hydrogen atom, a hydroxyl group, a halogen atom, an alkoxyl group, or an alkyl group which may be substituted by a halogen atom, Y' represents a hydroxyl group, a halogen atom, alkoxyl group, or an alkyl group which may be substituted by a halogen atom, and the substitution of the benzene ring bonding with the piperidine ring and the group —$CH_2C_6H_4Y'$ is in a meta or para position.

According to the present invention, further, there are provided compounds having the general formula (IIIa):

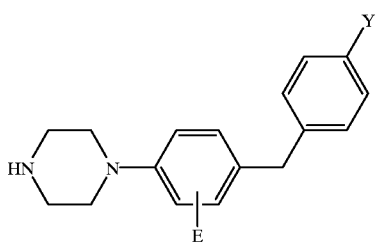

(IIIa)

wherein, E and Y may be the same or different from each other and represent a hydrogen atom, a hydroxyl group, a halogen atom, an alkoxy group, or an alkyl group which may be substituted by a halogen atom.

According to the present invention, further, there are provided compounds having the general formula (IIIb):

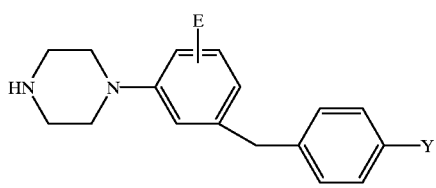

(IIIb)

wherein, E and Y may be the same or different from each other and represent a hydrogen atom, a hydroxyl group, a halogen atom, an alkoxyl group, or an alkyl group which may be substituted by a halogen atom.

The compounds (Ia), (Id), (Ig) and (I''a) in the general formulas (I), (I'), and (I'') wherein Z represents a carbon atom and the compounds (Ib), (Ie), (Ih) and (I''b) wherein Z represents CH may be synthesized from compounds having the general formula (II):

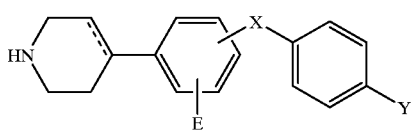

(II)

wherein, E and Y may be the same or different from each other and represent a hydrogen atom, a hydroxyl group, a halogen atom, an alkoxy group, or an alkyl group which may be substituted by a halogen atom, and the dotted line shows the presence or absence of a bond.

The compounds (II) are explained by the general formulas (IId), (IIe), (IIf) and (IIg).

In the general formula (IId):

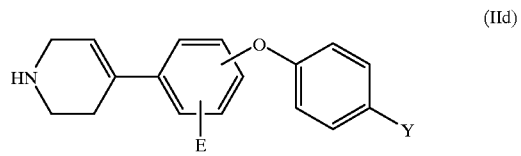

(IId)

wherein, E and Y are as defined above, preferable examples of the halogen atom represented by E or Y include a fluorine atom, a chlorine atom, and a bromine atom; preferable examples of the alkoxyl group include a $C_1$–$C_5$ alkoxy group which may be branched such as a methoxy group, and an ethoxy group; and preferable examples of the alkyl group which may be substituted by a halogen atom include a $C_1$–$C_5$ alkyl group which may be branched such as a methyl group, an ethyl group, and a trifluoromethyl group. Examples of the halogen atom of the alkyl group which may be substituted by a halogen atom include a fluorine atom, a chlorine atom, and a bromine atom. The substitution of the benzene ring bonding with the tetrahydropyridine ring and the group —$OC_6H_4Y$ is in an ortho, meta, or para position, preferably a para position.

In the general formula (IIe):

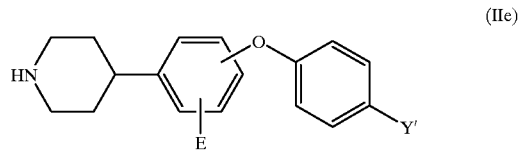

(IIe)

E and Y are as defined above, preferable examples of the halogen atom represented by E or Y include a fluorine atom, a chlorine atom, and a bromine atom; preferable examples of the alkoxyl group include a $C_1$–$C_5$ alkoxy group which may be branched such as a methoxy group, and an ethoxy group; and preferable examples of the alkyl group which may be substituted by a halogen atom include a $C_1$–$C_5$ alkyl group which may be branched such as a methyl group, an ethyl group, and a trifluoromethyl group. Examples of the halogen atom of the alkyl group which may be substituted by a halogen atom include a fluorine atom, a chlorine atom, and a bromine atom. The substitution of the benzene ring bonding with the piperidine ring and the group —$OC_6H_4Y$ is in an ortho, meta, or para position, preferably a para position.

In the general formula (IIf):

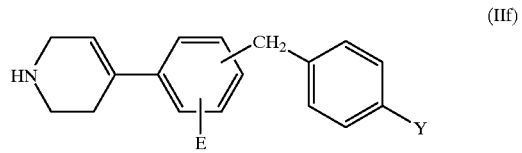

(IIf)

E and Y are as defined above, preferable examples of the halogen atom represented by E or Y include a fluorine atom, a chlorine atom, and a bromine atom; preferable examples of the alkoxyl group include a $C_1$–$C_5$ alkoxy group which may be branched such as a methoxy group, and an ethoxy group; and preferable examples of the alkyl group which may be substituted by a halogen atom include a $C_1$–$C_5$ alkyl group which may be branched such as a methyl group, an ethyl group, and a trifluoromethyl group. Examples of the halogen atom of the alkyl group which may be substituted by a halogen atom include a fluorine atom, a chlorine atom, and a bromine atom. The substitution of the benzene ring bonding with the tetrahydropyridine ring and the group —$CH_2C_6H_4Y$ is in an ortho, meta, or para position, preferably meta or para position.

In the general formula (IIg):

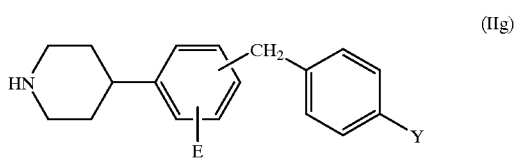

(IIg)

wherein, E and Y are as defined above, preferable examples of the halogen atom represented by E or Y include a fluorine atom, a chlorine atom, and a bromine atom; preferable examples of the alkoxyl group include a $C_1$–$C_5$ alkoxy group which may be branched such as a methoxy group, and an ethoxy group; and preferable examples of the alkyl group which may be substituted by a halogen atom include a $C_1$–$C_5$ alkyl group which may be branched such as a methyl group, an ethyl group, and a trifluoromethyl group. Examples of the halogen atom of the alkyl group which may be substituted by a halogen atom include a fluorine atom, a chlorine atom, and a bromine atom. The substitution of the benzene ring bonding with the piperidine ring and the group —$CH_2C_6H_4Y$ is in an ortho, meta, or para position, preferably meta or para position.

The compounds of the general formulas (I), (I'), (I") or (I'''), for example, may be synthesized in the following manners. These methods will be successively explained below.

The compounds (Ia), (Id), (Ig), and (I"a), (If) of the general formulas (I), (I'), and (I") wherein Z represents a carbon atom and the compounds (Ib), (Ie), (Ih), and (I"b), (Ig) wherein Z represents CH can be obtained as follows:

The compound (IIh) is obtained from a known starting material (IV) (step 1), then the compound (IIi) is obtained from the compound (IIh) (step 2). The compounds (Ia), (Id), (Ig), or (I"a) can be obtained from the compound (IIh) (step 3) and the compound (Ib), (Ie), (Ih), or (I"b) can be obtained from the compound (IIi) (step 4).

For compounds having the general formulas (I), (I'), and (I") wherein A represents an alkenylene group, the compound (Ij) can be obtained from the compound (IIh) (step 5) and the compound (Ik) can be obtained from the compound (IIi) (step 6).

For compounds having the general formulas (I), (I'), and (I") wherein B represents a hydroxyl group-substituted alkylene group, the compound (II) can be obtained from the compound (IIh) (step 7) and the compound (Im) can be obtained from the compound (IIi) (step 8).

For compounds having the general formulas (I), (I'), and (I") wherein B represents a methylene group, the compound (In) can be obtained from the compound (IIh) (step 9) and the compound (Io) can be obtained from the compound (IIi) (step 10).

Further, the compounds (Ic), (If), or (Ii) having the general formula (I) wherein Z represents a nitrogen atom or the compound (I''') having the general formula (I') wherein Z represents a nitrogen atom can be obtained from the known starting material (X) (step 11).

Step 1:

The compound (IIh) can be synthesized in accordance with the following method from the known starting material (IV):

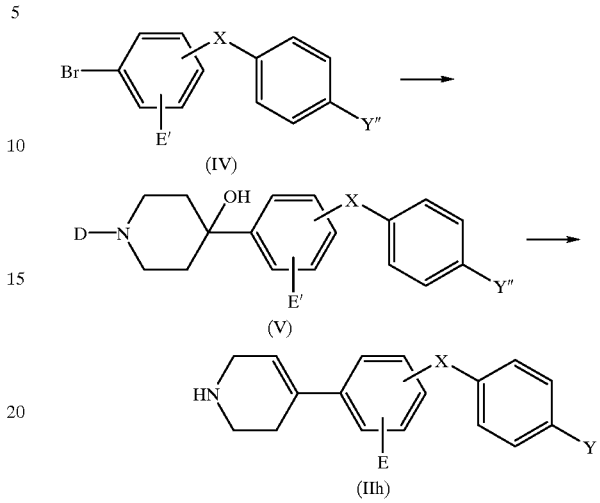

wherein, E, X, and Y are as defined above, E' and Y" may be the same or different and represent a hydrogen atom, a halogen atom, alkoxyl group, or a halogen atom-substitutable alkyl group, and D represents a tert-butoxycarbonyl group, ethoxycarbonyl group, or acetyl group.

That is, the aryl bromide derivative having the general formula (IV) is converted by the conventional method to the corresponding aryl Grignard reagent or aryl lithium reagent, then is allowed to react in tetrahydrofuran, diethylether, ethyleneglycol dimethylether, toluene, or another solvent not participating in the reaction, at –100 to 50° C., preferably –78° C. to room temperature, with 1 to 1.5 equivalents of the known starting material N-tert-butoxycarbonyl-4-piperidone, N-ethoxy carbonyl-4-piperidone, or N-acetyl-4-piperidone for 1 to 6 hours so as to obtain the compound having the general formula (V).

The starting substance (IV) used in the reaction is a known compound as described in Martin et al. [L. Martin et al: J. Med. Chem., 22, 1347 (1979)] or can be synthesized by the similar method. For example, 4-bromodiphenylether, 4-bromophenylether, 2-bromodiphenylmethane, 3-bromodiphenylmethane, 4-bromodiphenylmethane, 2-bromo-4'-fluorodiphenylmethane, 3-bromo-4'-fluorodiphenylmethane, 4-bromo-4'-fluorodiphenylmethane, 2-bromo-4'-chlorodiphenylmethane, 3-bromo-4'-chlorodiphenylmethane, 4-bromo-4'-chlorodiphenylmethane, 2-bromo-4'-methoxydiphenylmethane, 3-bromo-4'-methoxydiphenylmethane, 4-bromo-4'-methoxydiphenylmethane, 2-bromo-4'-trifluoromethyldiphenylmethane, 3-bromo-4'-trifluoromethyldiphenylmethane, 4-bromo-4'-trifluoromethyldiphenylmethane, 3-bromo-4-fluorodiphenylmethane, 3-bromo-4,4'-difluorodiphenylmethane, 3-bromo-4-fluoro-4'-chlorodiphenylmethane, 3-bromo-4-fluoro-4'-methoxydiphenylmethane, 3-bromo-4'-fluoro-4'-trifluoromethyldiphenylmethane, 3-bromo-4-methoxydiphenylmethane, 3-bromo-4-methoxy-4'-fluorodiphenylmethane, 3-bromo-4-methoxy-4'-chlorodiphenylmethane, 3-bromo-4,4'-dimethoxydiphenylmethane, 3-bromo-4-methoxy-4'- trifluoromethyldiphenylmethane, 5-bromo-2-methoxydiphenylmethane, 5-bromo-2-methoxy-4'-fluorodiphenylmethane, 5-bromo-2-methoxy-4'-chlorodiphenylmethane, 5-bromo-2,4'-dimethoxydiphenylmethane, 5-bromo-2-methoxy-4'-trifluoromethyldiphenylmethane, and the like may be used. Further, as the conditions for preparing the Grignard reagent and the organolithium reagent, use may be made of the various methods described in the "Compendium for Organic Synthesis" (Wiley-Interscience: A Division of John Wiley & Sons Ltd.) etc.

The compound obtained from the reaction can be used as is for the next step or if necessary can be used after purification by a generally used purification method such as recrystallization or column chromatography.

Next, the compound (V) thus obtained is treated under non-solvent conditions or in tetrahydrofuran, diethyl ether, ethyleneglycol dimethylether, benzene, toluene, methylene chloride, chloroform, carbon tetrachloride, water, methanol, ethanol, or another solvent not participating in the reaction, at −20 to 150° C., preferably 0 to 80° C., with 1 to 20 equivalents of organic acids such as acetic acid, trifluoroacetic acid, methanesulfonic acid, trifluoromethanesulfonic acid, and the like or inorganic acids such as hydrochloric acid, sulfuric acid, nitric acid, and the like for 1 to 12 hours, or the compound (V) is let to react in benzene, toluene, methylene chloride, chloroform, carbon tetrachloride, or another solvent not participating in the reaction, if necessary in the presence of triethylamine, pyridine, diisopropylethylamine, or other bases, at −20 to 150° C., preferably 0 to 100° C., with 1 to 5 equivalents of thionylchloride, methane sulfonylchloride, trifluoromethane sulfonylchloride, trifluoromethanesulfonic acid anhydride, p-toluene sulfonylchloride, phosphorus oxychloride, or other acid chloride derivatives for 1 to 6 hours, then performing an acid treatment similar to the above, so as to obtain a compound having the general formula (IIh).

Further, compounds having the general formula (IIh) wherein E or Y represents a hydroxyl group can be obtained by dealkylating a compound having the general formula (IIh) wherein E or Y represents an alkoxy group using the various methods described in "Protective Groups in Organic Synthesis" (T. W. Greene, John Wiley & Sons Ltd.) etc.

Step 2:

The compound (IIh) obtained in step 1 can be reduced to synthesize the compound (IIi):

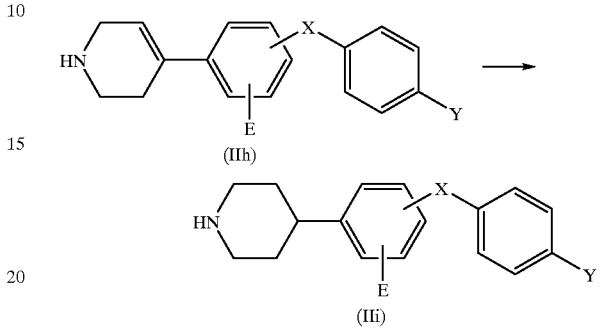

(wherein, E, X, and Y are as defined above.)

That is, the compound (IIh) obtained in step 1 can be hydrogenated in the presence of palladium carbon, platinum, or another catalyst in methanol, ethanol, ethyl acetate, or another solvent not participating in the reaction at room temperature so as to convert it to the compound having the general formula (IIi). Further, in the present reaction, if necessary, acetic acid, hydrochloric acid, or another acid may be added.

Step 3:

The compound (IIh) obtained in step 1 can be reacted with the compound (VI) or (VI') to synthesize the compounds (Ia), (Id), (Ig), or (I"a) having the general formula (I), (I') and (I") wherein Z is a carbon atom.

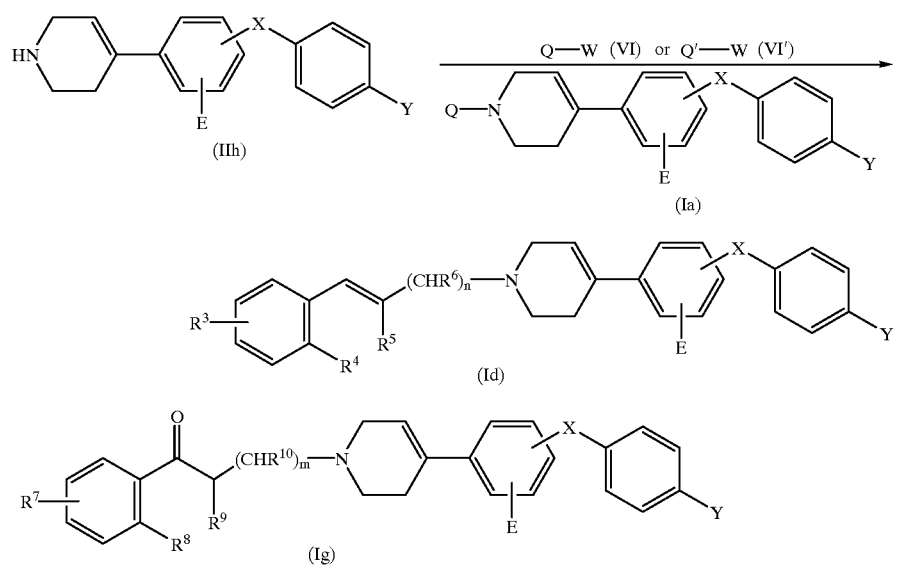

or

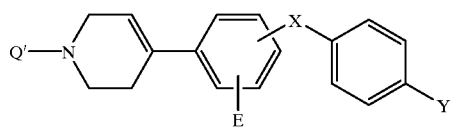

(I″a)

(wherein, Q, Q', E, X, Y, $R^3$, $R^4$, $R^5$, $R^6$, $R^7$, $R^8$, $R^9$, $R^{10}$, m, and n are as defined above, and W represents a group able to be easily exchanged with an amine group).

That is, the compound (IIh) obtained in step 1 may be allowed to react in tetrahydrofuran, diethylether, ethyleneglycol dimethylether, dioxane, acetonitrile, benzene, toluene, dimethylformamide, dimethylsulfoxide, or another solvent not participating in the reaction, in the presence of triethylamine, diisopropylethylamine, pyridine, or another organic base or sodium, potassium, sodium hydride, potassium hydride, sodium amide, sodium ethoxide, potassium tert-butoxide, sodium hydroxide, potassium hydroxide, sodium carbonate, potassium carbonate, cesium carbonate, cesium fluoride, or other inorganic bases, at −20 to 150° C., preferably room temperature to 100° C., with 1 to 1.5 equivalents of the compound (VI) or (VI') for 1 to 24 hours so as to obtain the tetrahydropyridine derivative of the general formula (Ia), (Id), (Ig), or (I″a). Further, in the present reaction, if necessary, sodium iodide or tetrabutylammonium iodide may be added.

W is a leaving group capable of being easily exchanged with an amine group and for example is a chlorine atom, bromine atom, or other halogen atom, alkylsulfonyloxy group such as a methane sulfonyloxy group or arylsulfonyloxy group such as a p-toluene sulfonyloxy group.

As the compound (VI) or (VI') usable in the present reaction, a commercially available or known compound may be used, for example, methyl iodide, ethyl iodide, ethyl bromide, propyl bromide, cinnamyl bromide, 3-bromo-2-methyl-1-phenyl-1-propene, 4-fluorocinnamyl bromide, (2,3,4-trimethoxy)cinnamyl bromide, 1-bromo-3-phenylpropane, (1-bromoethyl)benzene, (2-bromoethyl) benzene, 4-methoxycinnamyl bromide, 2-(4-fluorophenyl) oxyethyl bromide, 2-phenyloxyethyl bromide, 4-(4-fluorophenyl)oxybutyl bromide, 4-phenyloxybutyl bromide, 2-phenyloxypropyl bromide, trans-(2-phenyl) cyclopropylmethyl bromide, 1-phenyl-1-cyclopropylmethyl bromide, 1-phenyl-1-cyclopropanemethyl bromide, 1-phenyl-1-cyclopentanemethyl bromide, phenacyl bromide, 2-bromo-4'-methoxyacetophenone, 2-bromo-4'-fluoroacetophenone, 2-bromo-4'-chloroacetophenone, 2-bromopropiophenone, 2-bromo-2',4'-dimethoxyacetophenone, 2-bromo-2',5'-dimethoxyacetophenone, 2-bromo-4'-methylacetophenon, 4-chlorobutyrophenone, 4-chloro-4'-fluorobutyrophenone, 2-bromomethyl-2-phenyl-1,3-dioxolane, 2-bromomethyl-2-(4-fluorophenyl)-1,3-dioxolane, 2-bromomethyl-2-(4-chlorophenyl)-1,3-dioxolane, 2-bromomethyl-2-(4-methoxyphenyl)-1,3-dioxolane, 2-(1-bromoethyl)-2-phenyl-1,3-dioxolane, 2-bromomethyl-2-(4-methylphenyl)-1,3-dioxolane, 2-bromomethyl-2-(2,4-dimethoxyphenyl)-1,3-dioxolane, 2-bromomethyl-2-(2,5-dimethoxyphenyl)-1,3-dioxolane, 2,3,4-trimethoxybenzylchloride, benzyl bromide, 4-fluorobenzyl bromide, 2-fluorobenzyl bromide, 3-fluorobenzyl bromide, 4-(trifluoromethyl)benzyl bromide, 2-(trifluoromethyl)benzyl bromide, 3-(trifluoromethyl) benzyl bromide, 2-bromo-1-indanone, 2-bromomethylbenzofuran, (2-bromo-1-hydroxyiminoethyl)benzene, 3-methoxybenzyl chloride, 4-methoxybenzyl chloride, cinnamyl chloride, (2-bromo-1-methoxyethyl)benzene, 1-(4-chlorophenyl) cyclobutanemethyl bromide, 1-(4-chlorophenyl) cyclopentanemethyl bromide, 1-(4-methoxyphenyl) cyclopentanemethyl bromide, (2-bromo-1,1-diethoxy ethyl) benzene, etc. may be used.

Further, the compounds of the general formulas (Ia) and (I″a) where A is a hydroxyiminomethylene group may be obtained by causing the corresponding ketone obtained in this step to react in pyridine, water, alcohol, water/alcohol or other solvent in the presence of pyridine, sodium hydroxide, potassium hydroxide, sodium hydrogencarbonate, potassium hydrogencarbonate, sodium carbonate, potassium carbonate or other base with hydroxyamine or its acid addition salt. Further, the compounds of the general formulas (Ia) and (I″a) where B is a hydroxyl group-substituted alkylene group may be obtained by reducing the corresponding ketone obtained in this step by sodium borohydride, lithium aluminum hydride, aluminum dibutyl hydride, borane, and other metal reducing agents or by catalyzing hydrogenation in the presence of a catalytic amount of palladium carbon, platinum, etc.

Step 4:

The compound (VI) can be reacted with the compound (IIi) obtained in step 2 by a similar method as in step 3 to synthesize the compound (Ib):

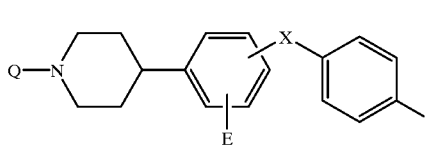

(Ib)

Compound (Ie):

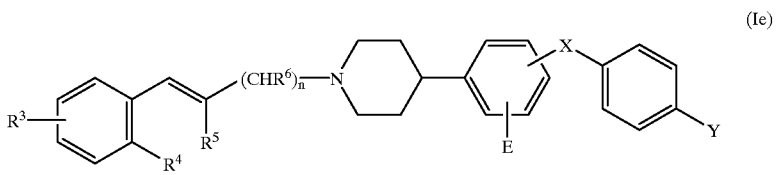

(Ie)

Compound (Ih):

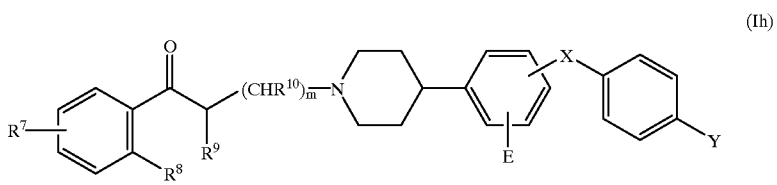

(Ih)

or Compound (I"b):

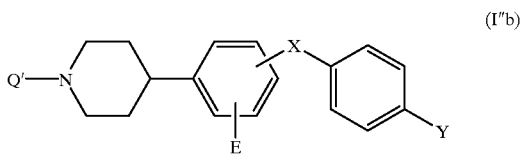

(I"b)

(wherein, Q', E, X, Y, $R^3$, $R^4$, $R^5$, $R^6$, $R^7$, $R^8$, $R^9$, $R^{10}$, n, and m are as defined above) having the general formula (I), (I'), and (I") where Z is CH.

Step 5:

The compounds (Ij) having the general formulas (I), (I'), and (I") wherein A is an alkenylene group and Z is a carbon atom can be synthesized from the compound (IIh) obtained in step 1:

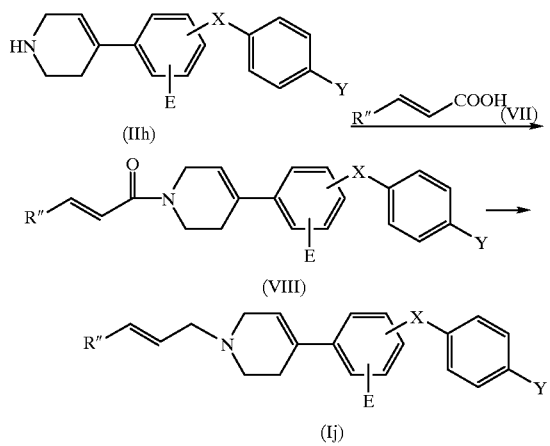

(wherein, E, X, and Y are as defined above, and R" represents a substituted or unsubstituted phenyl group.)

That is, the compound (IIh) obtained at step 1 and the cinnamic acid derivative (VII) may be condensed by an ordinary method to convert to the amide derivative of the general formula (VIII), then reduced in tetrahydrofuran, diethylether, ethyleneglycol dimethylether, or another solvent not participating in the reaction at −100° C. to 80° C., preferably −78° C. to room temperature, by 1 to 5 equivalents of lithium aluminum hydride or sodium bis(2-methoxyethoxy) aluminum hydride for 1 to 12 hours.

As the conditions of aforementioned amidation reaction, the various methods described in the "Compendium for Organic Synthesis" (Wiley-Interscience: A Division of John Wiley & Sons Ltd.)) etc. may be used. For example, the method of treating the cinnamic acid derivative (VII) if necessary in the presence of an organic or inorganic base with diethylphosphate cyanide (DEPC), diphenylphosphate adide (DPPA), dicyclohexylcarbodiimide (DCC), 1-ethyl-3-(3-dimethylaminopropyl)carbodiimide hydrochloride, 2-iodo-1-methylpyridinium iodide, and the like may be used, or the cinnamic acid derivative (VII) may be made by an ordinary method into an acid halide, symmetric acid anhydride, mixed acid anhydride, or other active ester, etc., then condensed with the compound (IIh).

As the cinnamic acid derivative (VII) usable in the present reaction, a commercially available or known compound may be used, for example, cinnamic acid, 2,3,4-trimethoxycinnamic acid, α-methylcinnamic acid, 4-hydroxy-3-methoxycinnamic acid, 3-hydroxy-4-methoxycinnamic acid, 4-chlorocinnamic acid, 3-chlorocinnamic acid, 2-chlorocinnamic acid, 4-fluorocinnamic acid, 3-fluorocinnamic acid, 2-fluorocinnamic acid, 3,4,5-trimethoxycinnamic acid, 2-(trifluoromethyl)cinnamic acid, 3-(trifluoromethyl)cinnamic acid, 4-(trifluoromethyl)cinnamic acid, 2-hydroxycinnamic acid, 3-hydroxycinnamic acid, 4-hydroxycinnamic acid, 2-methoxycinnamic acid, 3-methoxycinnamic acid, 4-methoxycinnamic acid, 2,6-difluorocinnamic acid, 2,4-difluorocinnamic acid, 2,5-difluorocinnamic acid, 3,4-difluorocinnamic acid, 3,5-difluorocinnamic acid, 2,6-dichlorocinnamic acid, 2,4-dichlorocinnamic acid, 3,4-dichlorocinnamic acid, 2,3-dimethoxycinnamic acid, 2,4-dimethoxycinnamic acid, 2,5-dimethoxycinnamic acid, 3,4-dimethoxycinnamic acid, 3,4-(methylenedioxy)cinnamic acid, 3,5-dimethoxycinnamic acid, 3,4-dihydroxycinnamic acid, 3,4-dimethoxy-4-hydroxycinnamic acid, 2,4,5-trimethoxycinnamic acid, α-methyl-2 4,5-trimethoxycinnamic acid, etc. may be used.

The compounds obtained in aforementioned reactions may be used as they are for the next step, but may also be used after purification if necessary by a generally used purification method such as recrystallization or column chromatography etc.

Step 6:

The compounds (Ik) having the general formulas (I), (I'), and (I") where A is an alkenylene group and Z is CH:

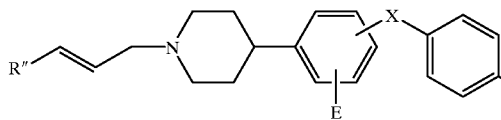

(Ik)

wherein E, R", X, and Y are as defined above can be synthesized from the compound (IIi) obtained in step 2 by the similar method as step 5.

Step 7:

The compounds (Il) having the general formulas (I), (I'), and (I") where A is a connecting bond, B is a hydroxyl group-substituted alkylene group, and Z is a carbon atom:

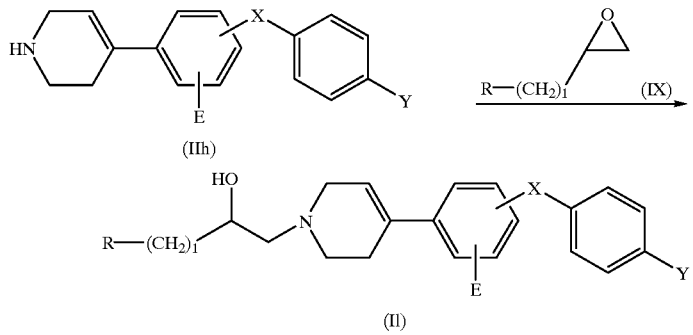

(wherein, l represents an integer of 0 or 1, and E, R, X, and Y are as defined above), can be synthesized from the compound (IIh) obtained at step 1.

That is, compound (IIh) obtained at step 1 may be allowed to react in tetrahydrofuran, diethylether, ethyleneglycol dimethylether, dioxane, acetonitrile, benzene, toluene, dimethylformamide, dimethylsulfoxide, methanol, ethanol, isopropylalcohol, tert-butylalcohol, ethyleneglycol, or another solvent not participating in the reaction, at room temperature to 200° C., preferably 50° C. to 150° C., with 0.9 to 1.5 equivalents of the compound (IX) for 1 to 24 hours.

As the compound (IX) usable in the present reaction, a commercially available or known compound may be used, for example, 1,2-epoxyethylbenzene, (R)-(+)-1,2-epoxyethylbenzene, (S)-(−)-1,2-epoxyethylbenzene, (1R,2R)-(+)-1-phenylpropylene oxide, (1S,2S)-(−)-1-phenylpropylene oxide, 1,2-epoxy-3-phenoxypropylene, (K)-(−)-2-(benzyloxymethyl)oxirane, (S)-(+)-2-(benzyloxymethyl)oxirane, 2,3-epoxypropylbenzene, glycidyl 2-methylphenyl ether, 4-tert-butylphenyl 2,3-epoxypropyl ether, 4-chlorophenyl 2,3-epoxypropyl ether, 2,3-epoxypropyl 4-methoxyphenyl ether, etc. may be used.

Further, in the present reaction, if necessary, triethylamine, diisopropylethylamine, pyridine and other organic bases, sodium, potassium, sodium hydroxide, potassium hydroxide, sodium amide, sodium ethoxide, potassium tert-butoxide, sodium hydroxide, potassium hydroxide, sodium carbonate, potassium carbonate, cesium carbonate, cesium fluoride, and other inorganic bases, or sodium iodide, tetrabutylammonium iodide, lithium carbonate, lithium chloride, zinc bromide, magnesium bromide, and other metal salts may be added alone or in combinations of a plurality of types.

Step 8:

Using the same method as in step 7, the compounds (Im) of the general formulas (I), (I'), and (I") where A is a connecting bond, B is a hydroxyl group-substituted alkylene group, Z is CH:

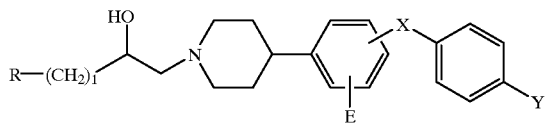

(Im)

(wherein, l, E, R, X, and Y are as defined above) can be synthesized from the compound (III) obtained at step 2.

Step 9:

The compounds (In) of the general formulas (I), (I'), and (I") wherein A is a connecting bond, B is a methylene group, and Z is a carbon atom can be synthesized from the compound (IIh) obtained in step 1.

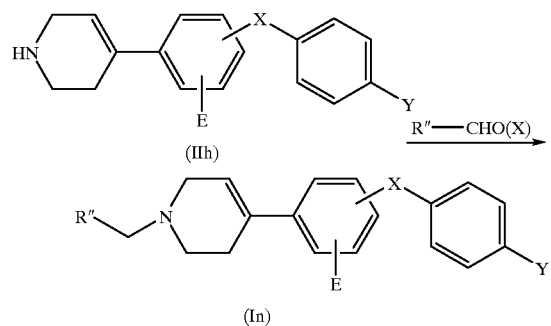

(wherein, E, R", X, and Y are as defined above.)

That is, the compound (IIh) obtained at step 1 and 1 to 1.2 equivalents of aldehyde (X) may be treated at room temperature to 200° C., preferably 80 to 150° C., while agitating, with 1 to 2 equivalents of formic acid to obtain the compound (In). Alternatively, the compound (IIh) and 1 to 1.2 equivalents of aldehyde may be treated in methanol, ethanol, isopropylalcohol, water, methanol/water or another solvent not participating in the reaction, if necessary adding sodium hydrogencarbonate, sodium dihydrogenphosphate, potassium dihydrogenphosphate, or aqueous solutions of the same, at −20 to 50° C., preferably 0° C. to room temperature, by 0.3 to 2 equivalents of sodium cyanoborohydride to obtain the compound (In).

As the compound (X) usable in the present reaction, a commercially available or known compound may be used, for example, benzaldehyde, 2-fluorobenzaldehyde, 2-chlorobenzaldehyde, o-anisaldehyde, m-anisaldehyde, p-anisaldehyde, α,α,α-trifluoro-o-tolualdehyde, α,α,α-trifluoro-m-tolualdehyde, α,α,α-trifluoro-p-tolualdehyde, 3-fluorobenzaldehyde, 3-chlorobenzaldehyde, 4-fluorobezaldehyde, 4-chlorobenzaldehyde, o-tolualdehyde, m-tolualdehyde, p-tolualdehyde, 3-fluoro-2-methylbenzaldehyde, 2-fluoro-3-(trifluoromethyl)benzaldehyde, 3,4-difluorobenzaldehyde, 2,3-difluorobenzaldehyde, 3-fluoro-p-anisaldehyde, 2,4-dimethoxybenzaldehyde, 2,5-dimethoxybenzaldehyde, 3,4-dimethoxybenzaldehyde, piperonal, 1,4-benzodioxane-6-carbaldehyde, 3,5-bis(trifluoromethyl)benzaldehyde, 3,5-dimethoxybenzaldehyde, 2,3-dimethyl-p-anisaldehyde, 2,3,4-trimethoxybenzaldehyde, 3,4,5-trimethoxybenzaldehyde, 2,4,5-trimethoxybenzaldehyde, 2,4,6-trimethoxybenzaldehyde, etc. may be used.

Step 10:

Using the similar method as in step 9, the compound (Io) of the general formulas (I), (I'), and (I") wherein A is a connecting bond, B is a methylene group, and Z is CH:

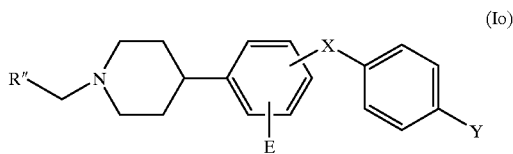

wherein, E, R", X, and Y are as defined above can be synthesized from the compound (IIi) obtained in step 2.

Step 11:

The compounds (Ic), (If), or (Ii) having the general formula (I) wherein Z is a nitrogen atom or the compound (I''') having the general formula (II) wherein Z is a nitrogen atom:

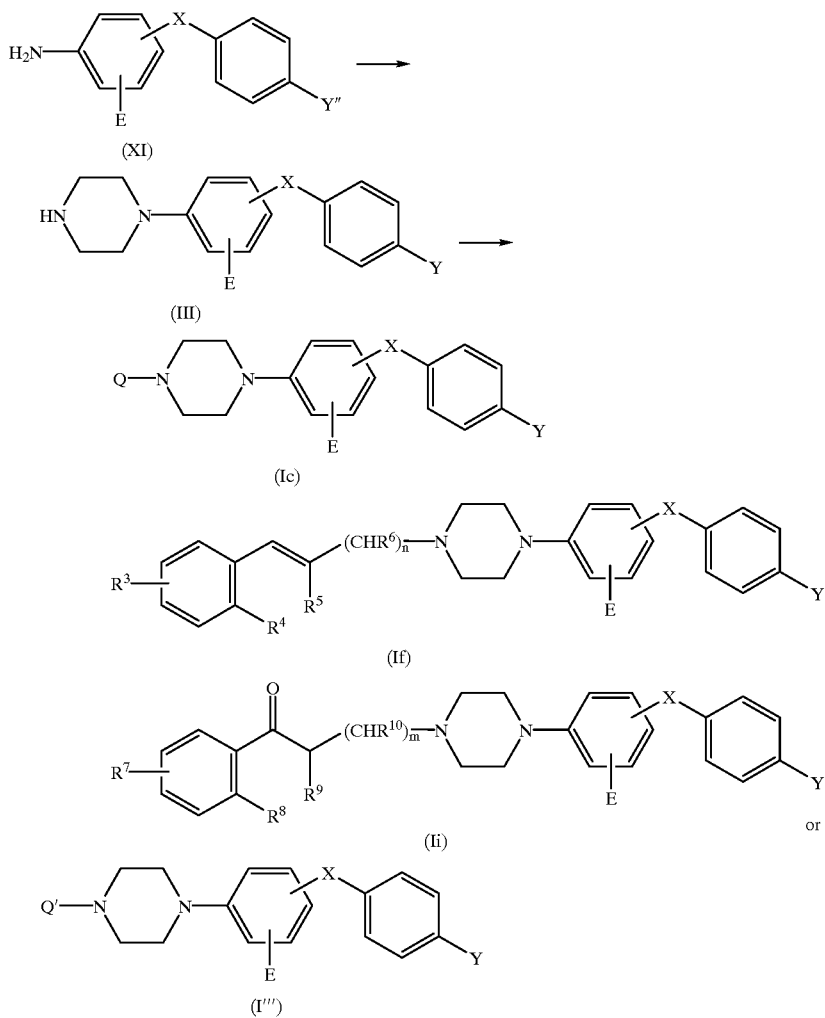

(wherein, Q, Q', E, E', X, Y, Y", $R^3$, $R^4$, $R^5$, $R^6$, $R^7$, $R^8$, $R^9$, $R^{10}$, n, and m are as defined above) can be synthesized from the known starting material (XI).

That is, by causing the aniline derivative having the general formula (XI) to react under non-solvent conditions or in n-butanol, tert-butylalcohol or another solvent not participating in the reaction at 80° C. to 300° C., preferably 150° C. to 250° C., with 1 to 1.5 equivalents of a known bis-2-chloroethylamine hydrochloride for 1 to 12 hours, the compound of the general formula (III) can be obtained.

The starting material (XI) usable in the present reaction may be a compound which is commercially available or known through the literature [K. Suzuki et al.: J. Org. Chem., 26, 2239 (1961)] or may be synthesized by a known method as described for example in Japanese Examined Patent Publication (Kokoku) No. 6-25191. For example, 2-phenoxyaniline, 3-phenoxyaniline, 4-phenoxyaniline, 2-benzylaniline, 4-benzylaniline, 4-(4-fluorophenyl) methylaniline, 2-(4-fluorophenyl)methylaniline, 4-(4-methoxyphenyl)methylaniline, 2-(4-methoxyphenyl) methylaniline, 4-(4-chlorophenyl)methylaniline, 2-(4-chlorophenyl)methylaniline, 4-methylaniline, 2-methylaniline, 2-benzyl-5-methoxyaniline, 4-benzyl-3-methoxyaniline, 2-(4-fluorophenyl) methyl-5-methoxyaniline, 4-(4-fluorophenyl) methyl-3-methoxyaniline, 5-fluoro-2-(4-fluorophenyl)methylaniline, 3-fluoro-4-(4-fluorophenyl)methylaniline, 5-fluoro-2-(4-methoxyphenyl)methylaniline, 3-fluoro-4-(4-methoxyphenyl)methylaniline, 5-methoxy-2-(4-methoxyphenyl)methylaniline, 3-methoxy-4-(4-methoxyphenyl)methylaniline, etc. may be used.

Further in the reaction according to the present invention, if necessary, sodium hydrogencarbonate, potassium hydrogencarbonate, sodium carbonate, potassium carbonate or other inorganic bases may be added.

Further, the compound having the general formula (III) wherein E or Y is a hydroxyl group may be obtained by removing the protective group from the compound having the general formula (III) where E or Y is an alkoxy group using the various methods described in "Protective Groups in Organic Synthesis" (T. W. Greene, John Wiley & Sons Ltd.) etc.

The compound (III) obtained in the aforementioned reaction can be used as it is for the next step, but can also be used after purification if necessary by a generally used purification method such as recrystallization or column chromatography etc.

The resultant compound (III) can be converted to the aryl piperadine derivatives having the general formulas (Ic), (If), (Ii), or (I''') by treating the said compound by the same methods as in, step 3, step 5, step 7, or step 9.

The isomers included in the compounds having the general formulas (I), (I'), (I''), and (I''') of the present invention may be separated by ordinary methods, for example, recrystallization, column chromatography, thin layer chromatography, high pressure liquid chromatography, or the similar methods using optically active reagents.

The compound having general formulas (I), (I'), (I''), and (I''') according to the present invention may be dissolved in a suitable organic solvent, for example, ether, tetrahydrofuran, methylene chloride, chloroform, benzene, toluene, etc. and treated by an inorganic or organic acid to obtain the corresponding salt. The inorganic acid used here include hydrochloric acid, sulfuric acid, nitric acid, phosphoric acid, periodic acid, and the like and the organic acid include formic acid, acetic acid, lactic acid, oxalic acid, malonic acid, propionic acid, valeric acid, succinic acid, fumaric acid, maleic acid, citric acid, malic acid, benzoic acid, p-toluenesulfonic acid, methanesulfonic acid, and the like.

The compounds having the general formula (I), (I'), (I'') and (I''') of the present invention are low in toxicity and can be used alone by themselves or if desired can be prepared with other normal pharmaceutically allowable known and generally used carriers into preparations designed for the alleviation and treatment of symptoms based on ischemic diseases and symptoms derived from seizures, epilepsy, and migraine. For example, the effective ingredient can be administered orally or nonorally by itself or made into a capsule, tablet, injection, or other suitable preparation together with usually used excipients. For example, capsule preparations are prepared by mixing the powder with lactose, starch or its derivatives, cellulose derivatives or other excipients and packing the mixture into gelatin capsules. Further, tablets can be prepared by adding and kneading in, in addition to said excipient, sodium carboxycarboxymethylcellulose, alginic acid, arabia gum, and other binders and water, if necessary granulating the same, then further adding talc, stearic acid, and other lubricants and preparing the final form using a usual compression tablet-making machine. At the time of non-oral administration using injection, the effective ingredient is dissolved together with a solubilizer in sterilized distilled water or sterilized physiological saline and sealed in an ampule to make the injection preparation. If necessary, a stabilizing agent, buffer, etc. may also be included.

The dosage of the medicine for alleviation or treatment of symptoms based on ischemic diseases and symptoms derived from seizures, epilepsy and migraine of the present invention depends on various factors, for example, the symptoms and age of the patient to be treated, the route of administration, the form of the preparation, the frequency of administration, etc., but usually is 0.1 to 1000 mg/day/person, preferably 1 to 500 mg/day/person.

EXAMPLES

The present invention will now be explained in further detail with reference to Reference Examples and Examples, but the present invention is of course not limited in scope to these Examples.

Reference Example 1

Synthesis of N-tert-butoxycarbonyl-4-(4-phenoxyphenyl)-4-piperidinol (1) (Note: Table 1 Compound No. 1 (same below))

To a 100 ml tetrahydrofuran solution of 3.5 g of N-tert-butoxycarbonyl-4-piperidone was added dropwise, under ice cooling, 35 ml of 4-phenoxyphenyl magnesium bromide (0.6 mol/l tetrahydrofuran solution) prepared from 4-bromodiphenylether. This was stirred for 1 hour. To the reaction mixture was added 30 ml of a saturated aqueous solution of ammonium chloride. This was then extracted with ether. The extract was washed with saturated saline, dried, filtered, then concentrated under reduced pressure to obtain a residue which was then purified by silica gel column chromatography (hexane:ethyl acetate=3:1) to obtain the above-referenced compound (1) in an amount of 2.92 g (yield 45%).

Reference Example 2

Synthesis of N-tert-butoxycarbonyl-4-[4-(4-fluorophenyl)methylphenyl]-4-piperidinol (2)

To a 25 ml ether solution of 2.5 g of 4-bromo-4'-fluorodiphenylmethane was gradually added dropwise at −78° C. 6.5 ml of n-butyl lithium (1.6 mol/l hexane solution). This was warmed up to −20° C. and stirred for 1 hour, then an 8 ml tetrahydrofuran solution of 1.8 g of N-tert-butoxycarbonyl-4-piperidone was added dropwise. This was stirred at 0° C. for one hour, then 15 ml of a saturated aqueous solution of ammonium chloride was added and extraction was performed with ether. The extract was washed with saturated saline, dried, filtered, then concentrated under reduced pressure to obtain a residue, which was then purified by silica gel column chromatography (hexane:ethyl acetate=4:1) to obtain the above-referenced compound (2) in an amount of 2.69 g (yield 77%).

Reference Example 3

Synthesis of N-tert-butoxycarbonyl-4-[3-(4-fluorophenyl)methylphenyl]-4-piperidinol (3)

The same procedure was followed as in Reference Example 2 using 3-bromo-4'-fluorodiphenylmethane to produce the above.

Reference Example 4

Synthesis of N-tert-butoxycarbonyl-4-[4-(4-methoxyphenyl)methylphenyl]-4-piperidinol (4)

The same procedure was followed as in Reference Example 2 using 4-bromo-4'-methoxydiphenylmethane to produce the above.

Reference Example 5

Synthesis of (E)-1-[3-(4-hydroxy-3-methoxyphenyl)-1-oxo-2-propenyl]-4-(4-phenoxyphenyl)piperidine (5)

To a 25 ml methylene chloride solution of 0.95 g of 4-hydroxy-3-methoxycinnamic acid and 1.24 g of the compound (9) synthesized in Example 2 was added under ice cooling 1.41 g of 1-ethyl-3-(3-dimethylaminopropyl) carbodiimide hydrochloride, then the resulting mixture was stirred at room temperature for two hours. The reaction was washed with saturated saline, dried, filtered, then concentrated under reduced pressure to obtain a residue which was then purified by silica gel column chromatography (hexane:ethyl acetate= 3:1) to obtain the above-referenced compound (5) in an amount of 1.62 g (yield 91%).

Reference Example 6

Synthesis of (E)-1-[3-(4-hydroxy-3-methoxyphenyl)-1-oxo-2-propenyl]-4-(4-phenoxyphenyl)-1,2,3,6-tetrahydropyridine (6)

The same procedure was followed as in Reference Example 5 using the compound (8) synthesized in Example 1 to produce the above.

Reference Example 7

Synthesis of (E)-4-[4-(4-fluorophenyl) methylphenyl]-1-[3-(4-hydroxy-3-methoxyphenyl)-1-oxo-2-propenyl]piperazine (7)

The same procedure was followed as in Reference Example 5 using the compound (10) synthesized in Example 3 to produce the above.

Example 1

Synthesis of 4-(4-phenoxyphenyl)-1,2,3,6-tetrahydropyridine (8)

To a 3 ml methylene chloride solution 772 mg of the compound (1) synthesized in Reference Example 1 was added dropwise under ice cooling 3 ml of trifluoroacetic acid. The resulting mixture was stirred at room temperature for two hours, then was adjusted by a 10% aqueous solution of sodium hydroxide to a pH=9 to 10 and extracted with ether. The extract was dried, filtered, then concentrated under reduced pressure to obtain a crude crystal which was then recrystallized from ether/methylene chloride to obtain the above-referenced compound (8) in an amount of 250 mg (yield 47%).

Example 2

Synthesis of 4-(4-phenoxyphenyl)piperidine (9)

To a 100 ml methanol solution of 3.51 g of the compound (8) synthesized in Example 1 were added 200 mg of palladium carbon and 1 ml of acetic acid for hydrogenation at atmospheric pressure and room temperature. After the completion of the reaction, the insolubles were filtered off, then the filtrate was concentrated under reduced pressure. The obtained residue was dissolved in methylene chloride and adjusted by a 10% aqueous solution of sodium hydroxide to a pH 9 to 10, then was shaken. The organic layer was dried, filtered, then condensed under reduced pressure to obtain a residue which was then purified by silica gel column chromatography (methylene chloride:methanol=20:1) to obtain the above-referenced compound (9) in an amount of 2.32 g (yield 66%).

Example 3

Synthesis of 1-[4-(4-fluorophenyl)methylphenyl] piperazine (10)

A mixture of 500 mg of 4-(4-fluorophenyl)methylaniline and 445 mg of bis(2-chloroethyl)amine hydrochloride was stirred at 100° C. for two hours, then gradually raised in temperature and stirred at 200° C. for a further two hours. This was cooled to room temperature, then the product was purified by silica gel column chromatography (chloroform:methanol:water (2% acetic acid)=65:35:5) to obtain the above-referenced compound (10) in an amount of 503 mg (yield 75%).

Example 4

Synthesis of 4-[4-(4-fluorophenyl)methylphenyl]-1,2,3,6-tetrahydropyridine (11)

The same procedure was followed as in Example 1 using the compound (2) synthesized in Reference Example 2 to produce the above.

Example 5

Synthesis of 4-[4-(4-fluorophenyl)methylphenyl] piperidine (12)

The same procedure was followed as in Example 2 using the compound (11) synthesized in Example 4 to produce the above.

Example 6

Synthesis of 4-[3-(4-fluorophenyl)methylphenyl]-1,2,3,6-tetrahydropyridine (13)

The same procedure was followed as in Example 1 using the compound (3) synthesized in Reference Example 3 to produce the above.

Example 7

Synthesis of 4-[3-(4-fluorophenyl)methylphenyl] piperidine (14)

The same procedure was followed as in Example 2 using the compound (13) synthesized in Example 6 to produce the above.

Example 8

Synthesis of 1-[2-(4-fluorophenyl)methylphenyl] piperazine (15)

The same procedure was followed as in Example 3 using 2-(4-fluorophenyl)methylaniline to produce the above.

Example 9

Synthesis of 4-[4-(4-methoxynhenyl)methylphenyl]-1,2,3,6-tetrahydropyridine (16)

The same procedure was followed as in Example 1 using the compound (4) synthesized in Reference Example 4 to produce the above.

Example 10

Synthesis of 4-[4-(4-methoxyphenyl)methylphenyl] piperidine (17)

The same procedure was followed as in Example 2 using the compound (16) synthesized in Example 9 to produce the above.

Example 11

Synthesis of (E)-4-(4-phenoxyphenyl)-1-(3-phenyl-2-propenyl)-1,2,3,6-tetrahydropyridine (18)

To an 8 ml acetonitrile solution of 300 mg of the compound (8) synthesized in Example 1 were added 234 mg cinnamyl bromide and 0.5 ml of triethylamine. This was then heated and refluxed for 3 hours. To the reaction mixture was added 10 ml of ice water. This was then extracted with ethyl acetate. The extract was dried, filtered, then concentrated under reduced pressure to obtain a residue which was then purified by silica gel column chromatography (methylene chloride:methanol=25:1) to obtain the above-referenced compound (18) in an amount of 320 mg (yield 73%).

Example 12

Synthesis of (E)-1-[3-(4-hydroxy-3-methoxyphenyl)-2-propenyl]-4-(4-phenoxyphenyl) piperidine (9)

To an 8 ml tetrahydrofuran solution of 400 mg of the compound (5) synthesized in Reference Example 5 was added under ice cooling 60 mg of lithium aluminum hydride, then the resulting mixture was stirred at room temperature for two hours. A 10% aqueous solution of sodium hydroxide solution was added, then the product was extracted with methylene chloride. The extract was dried, filtered, then concentrated under reduced pressure to obtain a residue which was then purified by silica gel column chromatography (methylene chloride;methanol=20:1) to obtain the above-referenced compound (19) in an amount of 273 mg (yield 72%).

Example 13

Synthesis of 1-[2-(4-fluorophenyl)oxyethyl]-4-(4-phenoxyphenyl)-1,2,3,6-tetrahydropyridine (20)

The same procedure was followed as in Example 11 using the compound (8) synthesized in Example 1 and 2-(4-fluorophenyl)oxyethyl bromide to produce the above.

Example 14

Synthesis of (E)-4-(4-phenoxyohenyl)-1-(3-phenyl-2-propenyl)piperidine (21)

The same procedure was followed as in Example 11 using the compound (9) synthesized in Example 2 and cinnamyl bromide to produce the above.

Example 15

Synthesis of 4-(4-phenoxyphenyl)-1-(3-phenylpropyl)piperidine (22)

The same procedure was followed as in Example 11 using the compound (9) synthesized in Example 2 and 1-bromo-3-phenylpropane to produce the above.

Example 16

Synthesis of 4-(4-phenoxyphenyl)-1-[3-(2,3,4-trimethoxyphenyl)-2-propenyl]piperidine (23)

The same procedure was followed as in Example 11 using the compound (9) synthesized in Example 2 and (2,3,4-trimethoxy)cinnamyl bromide to produce the above.

Example 17

Synthesis of (E)-1-[3-(4-hydroxy-3-methoxyphenyl)-2-propenyl]-4-(4-phenoxyphenyl)-1,2,3,6-tetrahydropyridine (24)

The same procedure was followed as in Example 12 using the compound (6) synthesized in Reference Example 6 to produce the above.

Example 18

Synthesis of (E)-1-[3-(4-fluorophenyl)-2-propenyl]-4-(4-phenoxyphenyl)piperidine (25)

The same procedure was followed as in Example 11 using the compound (9) synthesized in Example 2 and 4-fluorocinnamyl bromide to produce the above.

Example 19

Synthesis of 4-(phenoxyphenyl)-1-[trans-(2-phenyl)cyclopropylmethyl]piperidine (26)

The same procedure was followed as in Example 11 using the compound (9) synthesized in Example 2 and trans-(2-phenyl)cyclopropylmethyl bromide to produce the above.

Example 20

Synthesis of 1-[2-(4-fluorophenyl)oxyethyl]-4-(4-phenoxyphenyl)piperidine (27)

The same procedure was followed as in Example 11 using the compound (9) synthesized in Example 2 and 2-(4-fluorophenyl)oxyethyl bromide to produce the above.

Example 21

Synthesis of 1-[4-(4-fluorophenyl)oxybutyl]-4-(4-phenoxyphenyl)piperidine (28)

The same procedure was followed as in Example 11 using the compound (9) synthesized in Example 2 and 2-(4-fluorophenyl)oxybutyl bromide to produce the above.

Example 22

Synthesis of 4-(4-phenoxyphenyl)-1-[(2,3,4-trimethoxyphenyl)methyl]piperidine (29)

A mixture of 1.27 g of the compound (9) synthesized in Example 2 and 0.8 g of 2,3,4-trimethoxybenzaldehyde was stirred at 120° C., then, 0.18 ml of formic acid was added dropwise. This was stirred for one hour at the same temperature, then ethyl acetate and a saturated aqueous solution of sodium hydrogencarbonate were added and the results were shaken. The organic layer was dried, filtered, then concentrated under reduced pressure to obtain a residue which was then purified by silica gel column chromatography (hexane:ethyl acetate=3:2) to obtain the above-referenced compound (29) in an amount of 1.46 g (yield 73%).

Example 23

Synthesis of 1-[4-((4-fluorophenyl)-4-oxo)butyl]-4-(4-phenoxyphenyl)piperidine (30)

To a 6 ml dimethylformamide solution of 350 mg of the compound (9) synthesized in Example 2 were added 278 mg of 4-chloro-4'-fluorobutylophenone, 230 mg of potassium carbonate, and 415 mg of sodium iodide, then the mixture was stirred at 80° C. for 2 hours. 15 ml of ice water was added, then the product was extracted with ethyl acetate. The extract was washed with saturated saline, dried, filtered, then concentrated under reduced pressure to obtain a residue, which was then purified by silica gel column chromatography (methylene chloride:methanol=20:1) to obtain the above-referenced compound (30) in an amount of 392 mg (yield 68%).

Example 24

Synthesis of (E)-4-[4-(4-fluorophenyl)methylphenyl]-1-(3-phenyl-2-propenyl)-1,2,3,6-tetrahydropyridine (31)

The same procedure was followed as in Example 11 using the compound (11) synthesized in Example 4 to produce the above.

Example 25

Synthesis of (E)-4-[4-(4-fluorophenyl)methylphenyl]-1-(3-phenyl-2-propenyl)piperidine (32)

The same procedure was followed as in Example 11 using the compound (12) synthesized in Example 5 to produce the above.

Example 26

Synthesis of 4-[4-(4-fluorophenyl)methylphenyl]-1-[trans-(2-phenyl)cyclopropylmethyl]piperidine (33)

The same procedure was followed as in Example 11 using the compound (12)-synthesized in Example 5 and trans-(2-phenyl)cyclopropylmethyl bromide to produce the above.

Example 27

Synthesis of (E)-4-[2-(4-fluorophenyl)methylphenyl]-(3-phenyl-2-propenyl)-1,2,3,6-tetrahydropyridine (34)

The same procedure was followed as in Example 11 using 4-[2-(4-fluorophenyl)methylphenyl]-1,2,3,6-tetrahydropyridine and cinnamyl bromide to produce the above.

Example 28

Synthesis of (E)-4-[2-(4-fluorophenyl)methylphenyl]-1-(3-phenyl-2-propenyl)piperidine (35)

The same procedure was followed as in Example 11 using 4-[2-(4-fluorophenyl)methylphenyl]piperidine to produce the above.

Example 29

Synthesis of 4-[2-(4-fluorophenyl)methylphenyl]-1-[trans-(2-phenyl)cyclopropylmethyl]piperidine (36)

The same procedure was followed as in Example 11 using 4-[2-(4-fluorophenyl)methylphenyl]piperidine and trans-(2-phenyl)cyclopropylmethyl bromide to produce the above.

Example 30

Synthesis of (E)-4-[3-(4-fluorophenyl)methylphenyl]-1-(3-phenyl-2-propenyl)-1,2,3,6-tetrahydropyridine (37)

The same procedure was followed as in Example 11 using the compound (13) synthesized in Example 6 to produce the above.

Example 31

Synthesis of (E)-4-[3-(4-fluorophenyl)methylphenyl]-1-(3-phenyl-2-propenyl)piperidine (38)

The same procedure was followed as in Example 11 using the compound (14) synthesized in Example 7 to produce the above.

Example 32

Synthesis of 4-[3-(4-fluorophenyl)methylphenyl]-1-[trans-(2-phenyl)cyclopropylmethyl]piperidine (39)

The same procedure was followed as in Example 11 using the compound (14) synthesized in Example 7 and trans-(2-phenyl)cyclopropylmethyl bromide to produce the above.

Example 33

Synthesis of (E)-1-(4-phenoxyphenyl)-4-(3-phenyl-2-propenyl)piperazine (40)

The same procedure was followed as in Example 11 using the 1-(4-phenoxyphenyl)piperazine [U.S. Pat. No. 4,210,646; DT2631885] to produce the above.

Example 34

Synthesis of 4-[4-(4-fluorophenyl)oxybutyl]-1-(4-phenoxyphenyl)piperazine (41)

The same procedure was followed as in Example 11 using the 1-(4-phenoxyphenyl)piperazine and 2-(4-fluorophenyl)oxybutyl bromide to produce the above.

Example 35

Synthesis of (E)-1-(2-phenoxyphenyl)-4-(3-phenyl-2-propenyl)piperazine (42)

The same procedure was followed as in Example 11 using 1-(2-phenoxyphenyl)piperazine [DT2631885] to produce the above.

Example 36

Synthesis of 1-(2-phenoxyphenyl)-4-[trans-(2-phenyl)cyclopropylmethyl]piperazine (43)

The same procedure was followed as in Example 11 using the 1-(2-phenoxyphenyl)piperazine and trans-(2-phenyl)cyclopropylmethyl bromide to produce the above.

Example 37

Synthesis of (E)-1-(3-phenoxyphenyl)-4-(3-phenyl-2-propenyl)piperazine (44)

The same procedure was followed as in Example 11 using 1-(3-phenoxyphenyl)piperazine [DT2631885] to produce the above.

Example 38

Synthesis of 1-(3-phenoxyphenyl)-4-[trans-(2-phenyl)cyclopropylmethyl]piperazine (45)

The same procedure was followed as in Example 11 using 1-(3-phenoxyphenyl)piperazine and trans-(2-phenyl)cyclopropylmethyl bromide to produce the above.

Example 39

Synthesis of 1-(4-phenoxyphenyl)-4-[(2,3,4-trimethoxyohenyl)methyl]piperazine (46)

The same procedure was followed as in Example 22 using 1-(4-phenoxyphenyl) piperazine to produce the above.

Example 40

Synthesis of (E)-1-[4-(4-fluorophenyl)methylphenyl]-1-(3-phenyl-2-propenyl)piperazine (47)

The same procedure was followed as in Example 11 using the compound (10) synthesized in Example 3 to produce the above.

Example 41

Synthesis of (E)-1-[4-(4-fluorophenyl)methylphenyl]-1-[3-(2,3,4-trimethoxyphenyl)-2-propenyl]piperazine (48)

The same procedure was followed as in Example 11 using the compound (10) synthesized in Example 3 and (2,3,4-trimethoxy) cinnamyl bromide to produce the above.

Example 42

Synthesis of (E)-1-[4-(4-fluorophenyl)methylphenyl]-4-[3-(4-hydroxy-3-methoxyohenyl)-2-propenyl]piperazine (49)

The same procedure was followed as in Example 12 using the compound (7) synthesized in Reference Example 7 to produce the above.

Example 43

Synthesis of (E)-1-[4-(4-fluorophenyl)methylphenyl]-4-[3-(4-fluorophenyl)-2-propenyl]piperazine (50)

The same procedure was followed as in Example 11 using the compound (10) synthesized in Example 3 and 4-fluorocinnamyl bromide to produce the above.

Example 44

Synthesis of (E)-1-(2-benzylphenyl)-4-(3-phenyl-2-propenyl)piperazine (51)

The same procedure was followed as in Example 11 using the 1-(2-benzylphenyl)piperazine [Japanese Examined Patent Publication (Kokoku) No. 6-25191] to produce the above.

Example 45

Synthesis of (E)-1-(2-benzylphenyl)-4-[trans-(2-phenyl)cyclopropylmethyl]piperazine (52)

The same procedure was followed as in Example 11 using 1-(2-benzylphenyl)piperazine and trans-(2-phenyl)cyclopropylmethyl bromide to produce the above.

Example 46

Synthesis of (E)-1-[2-(4-fluorophenyl)methylphenyl]-4-(3-phenyl-2-propenyl)piperazine (53)

The same procedure-was followed as in Example 11 using the compound (15) synthesized in Example 8 to produce the above.

Example 47

Synthesis of (E)-1-[2-(4-fluorophenyl)methylphenyl]-4-[trans-(2-phenyl)cyclopropylmethyl]piperazine (54)

The same procedure was followed as in Example 11 using the compound (15) synthesized in Example 8 and trans-(2-phenyl)cyclopropylmethyl bromide to produce the above.

Example 48

Synthesis of (E)-1-[4-(4-fluorophenyl)methylphenyl]-4-[trans-(2-phenyl)cyclopropylmethyl]piperazine (55)

The same procedure was followed as in Example 11 using the compound (10) synthesized in Example 3 and trans-(2-phenyl)cyclopropylmethyl bromide to produce the above.

Example 49

Synthesis of 1-[4-(4-fluorophenyl)methylphenyl]-4-[(2,3,4-trimethoxyphenyl)methyl]piperazine (56)

The same procedure was followed as in Example 22 using the compound (10) synthesized in Example 3 to produce the above.

Example 50

Synthesis of 4-[4-(4-fluorophenyl)oxybutyl]-1-[4-(4-fluorophenyl)methylphenyl]piperazine (57)

The same procedure was followed as in Example 11 using the compound (10) synthesized in Example 3 and 4-(4-fluorophenyl)oxybutyl bromide to produce the above.

Example 51

Synthesis of 1-[4-(4-fluorophenyl)methylphenyl]-4-[4-((4-fluorophenyl)-4-oxo)butyl]piperazine (58)

The same procedure was followed as in Example 23 using the compound (10) synthesized in Example 3 to produce the above.

Example 52

Synthesis of 4-(4-phenoxyphenyl)-1-(1-phenyl-1-cyclopropane)methylpiperidine (59)

The same procedure was followed as in Example 11 using the compound (9) synthesized in Example 2 and 1-phenyl-1-cyclopropanemethyl bromide to produce the above.

Example 53

Synthesis of 1-ethyl-4-(4-phenoxyphenyl)piperidine (60)

The same procedure was followed as in Example 11 using the compound (9) synthesized in Example 2 and ethyl iodide to produce the above.

Example 54

Synthesis of 1-[4-(4-fluorophenyl)methylphenyl]-4-methylpiperazine (61)

The same procedure was followed as in Example 11 using the compound (10) synthesized in Example 3 and methyl iodide to produce the above.

Example 55

Synthesis of 4-[4-(4-fluorophenyl)methylphenyl]-1-(1-phenyl-1-cyclopropane)methylpiperidine (62)

The same procedure was followed as in Example 11 using the compound (12) synthesized in Example 5 and 1-phenyl-1-cyclopropanemethyl bromide to produce the above.

Example 56

Synthesis of 4-[4-(4-fluorophenyl)methylphenyl]-1-(2-phenyl-2-oxo)ethylpiperidine (63)

The same procedure was followed as in Example 11 using the compound (12) synthesized in Example 5 and phenacyl bromide to produce the above.

Example 57

Synthesis of 4-(4-phenoxyphenyl)-1-(2-phenyl-2-oxo)ethylpiperidine (64)

The same procedure was followed as in Example 11 using the compound (9) synthesized in Example 2 and phenacyl bromide to produce the above.

Example 58

Synthesis of 4-[4-(4-fluorophenyl)methylphenyl]-1-(1-phenyl-1-cyclopropyl)methylpiperidine (65)

The same procedure was followed as in Example 11 using the compound (12) synthesized in Example 5 and 1-phenyl-1-cyclopropylmethyl bromide to produce the above.

Example 59

Synthesis of 1-[2-(4-methoxyphenyl)-2-oxo]ethyl-4-(4-phenoxyphenyl)piperidine (66)

The same procedure was followed as in Example 11 using the compound (9) synthesized in Example 2 and 2-bromo-4'-methoxyacetophenone to produce the above.

Example 60

Synthesis of 1-[2-(4-fluorophenyl)-2-oxo]ethyl-4-(4-phenoxyphenyl)piperidine (67)

The same procedure was followed as in Example 11 using the compound (9) synthesized in Example 2 and 2-bromo-4'-fluoroacetophenone to produce the above.

Example 61

Synthesis of 1-[2-(4-chlorophenyl)-2-oxo]ethyl-4-(4-phenoxyphenyl)piperidine (68)

The same procedure was followed as in Example 11 using the compound (9) synthesized in Example 2 and 2-bromo-4'-chloroacetophenone to produce the above.

Example 62

Synthesis of 1-(1-benzoylethyl)-4-(4-phenoxyphenyl)piperidine (69)

The same procedure was followed as in Example 11 using the compound (9) synthesized in Example 2 and 2-bromopropiophenone to produce the above.

Example 63

Synthesis of 4-[4-(4-methoxyphenyl)methylphenyl]-1-(2-phenyl-2-oxo)ethylpiperidine (70)

The same procedure was followed as in Example 11 using the compound (17) synthesized in Example 10 and phenacyl bromide to produce the above.

Example 64

Synthesis of 1-(1-oxoindan-2-yl)-4-(4-phenoxy)phenylpiperidine (71)

The same procedure was followed as in Example 11 using the compound (9) synthesized in Example 2 and 2-bromo-1-indanone to produce the above.

Example 65

Synthesis of 4-[4-(4-fluorophenyl)methylphenyl]-1-(1-oxoindan-2-yl)piperidine (72)

The same procedure was followed as in Example 11 using the compound (12) synthesized in Example 5 and 2-bromo-1-indanone to produce the above.

Example 66

Synthesis of 2-[4-(4-phenoxyphenyl)piperidin-1-yl]methyl-2-phenyl-1,3-dioxolane (73)

The same procedure was followed as in Example 11 using the compound (9) synthesized in Example 2 and 2-bromomethyl-2-phenyl-1,3-dioxolane to produce the above.

Example 67

Synthesis of 4-(4-phenoxyphenyl)-1-(2-phenyl-2-hydroxyimino)ethylpiperidine (74)

An 8 ml pyridine solution of 500 mg of the compound (64) synthesized in Example 57 and 96 mg of hydroxyamine hydrochloride was stirred for one hour at 100° C. To the reaction mixture was added 10 ml of ice water, then the product was extracted with ethyl acetate. The extract was washed with saturated saline, dried, filtered, then concentrated under reduced pressure. The obtained residue was purified by silica gel column chromatography (methylene chloride:methanol=20:1) to obtain the above-referenced compound (74) in an amount of 437 mg (yield 84%).

Example 68

Synthesis of 4-[4-(4-methoxyphenyl)methylphenyl]-(E)-1-(3-phenyl-2-propenyl)piperidine (75)

The same procedure was followed as in Example 11 using the compound (17) synthesized in Example 10 to produce the above.

Example 69

Synthesis of 1-(benzofuran-2-yl)methyl-4-(4-phenoxyphenyl)piperidine (76)

The same procedure was followed as in Example 11 using the compound (9) synthesized in Example 2 and 2-bromomethylbenzofuran to produce the above.

Example 70

Synthesis of 1-(2-hydroxy-2-phenyl)ethyl-4-(4-phenoxyphenyl)piperidine (77)

To 8 ml of a methanol solution of 450 mg of the compound (64) synthesized in Example 57 was gradually added 46 mg of sodium borohydride under ice cooling. The resulting mixture was stirred at room temperature for one hour. To the reaction was added 12 ml of ice water, then the product was extracted with ethyl acetate. The extract was washed with saturated saline, dried, filtered, then concentrated under reduced pressure. The obtained residue was purified by silica gel column chromatography (methylene chloride:methanol=20:1) so as to obtain the above-referenced compound (77) in an amount of 403 mg (yield 89%).

Example 71

Synthesis of 1-[2-(4-chlorophenyl)-2-hydroxy]ethyl-4-(4-phenoxyyhenyl)piperidine (78)

The same procedure was followed as in Example 70 using the compound (68) synthesized in Example 61 to produce the above.

Example 72

Synthesis of 4-[4-(4-fluorophenyl)methylphenyl]-1-(2-hydroxy-2-phenyl)ethylpiperidine (79)

The same procedure was followed as in Example 70 using the compound (63) synthesized in Example 56 to produce the above.

Example 73

Synthesis of 1-(2-hydroxy-3-phenoxy)propyl-4-(4-phenoxyphenyl)piperidine (80)

A 10 ml isopropyl alcohol solution of 300 mg of the compound (9) synthesized in Example 2 and 165 mg of phenyl glycidyl ether was stirred at 100° C. for two hours. The reaction was concentrated under reduced pressure to obtain a residue which was then purified by silica gel column chromatography (chloroform:methanol=20:1) to obtain the above-referenced compound (80) in an amount of 399 mg (yield 90%).

Example 74

Synthesis of 4-[4-(4-fluorophenyl)methylphenyl]-1-(2-hydroxy-3-phenoxy)propylpiperidine (81)

The same procedure was followed as in Example 73 using the compound (12) synthesized in Example 5 to produce the above.

Example 75

Synthesis of 1-[4-(4-fluorophenyl)methylphenyl]-4-(2-phenyl-2-oxo)ethylpiperazine (82)

The same procedure was followed as in Example 11 using the compound (10) synthesized in Example 3 and phenacyl bromide to produce the above.

The physical properties of the compounds obtained in the above Reference Examples and Examples are shown in Table 1.

TABLE 1

| Compound no. | Chemical structure | Properties m.p. (recrystallization solvent) | IR | $^1$H-NMR (CDCl$_3$) | Elemental analysis |
|---|---|---|---|---|---|
| 1 | 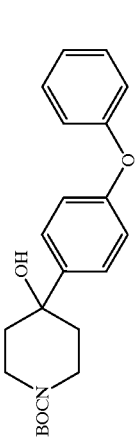 | An oily substance | (CHCl$_2$) 3094, 3436, 3010, 2980, 2875, 1682, 1589, 1507, 1489, 1430, 1367, 1242, 1168 | 1.48(9H, s), 1.77–1.78(2H, m), 1.98(2H, t), 3.25(2H, t), 4.24(2H, m), 6.99(4H, m), 7.08–7.14(1H, m), 7.34(2H, m), 7.40–7.46(2H, m) | — |
| 2 | 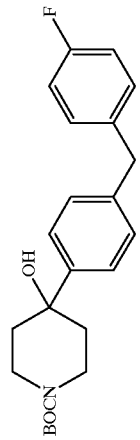 | An oily substance | (CHCl$_2$) 3018, 1682, 1508, 1431, 1367, 1168 | 1.48(9H, s), 1.70–1.74(2H, m), 1.97(2H, t), 3.24(2H, t), 3.94(2H, s), 4.00(2H, m), 6.94–6.99(2H, m), 7.11–7.17 (4H, m), 7.38(2H, d) | — |
| 3 | 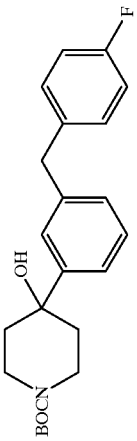 | An oily substance | (CHCl$_2$) 3468, 2979, 1684, 1508, 1426, 1162, 1032 | 1.47(9H, s), 1.6–1.7(2H, m), 1.96(2H, t), 3.25(2H, t), 3.95(2H, s), 6.9–7.45(8H, m) | — |
| 4 | 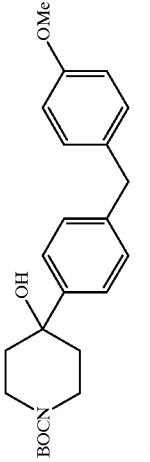 | An oily substance | (CHCl$_2$) 3019, 1676, 1509, 1225, 1206, 785, 772, 761, 750, 736, 672 | 1.42–1.49(9H, m), 1.72(2H, m), 1.98(2H, d), 3.24(2H, dt), 3.78(3H, s), 3.91(2H, s), 3.98(2H, m), 6.83(2H, dd), 7.10(2H, d), 7.17(2H, d), 7.37(2H, dd) | — |
| 5 | 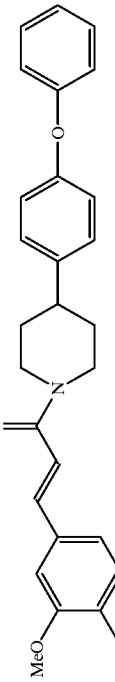 | Colorless crystals 88–90° C. (ethyl acetate/hexane) | (CHCl$_2$) 3020, 2400, 1644, 1594, 1509, 1489, 930 | 1.68(2H, ddd), 1.95(2H, d), 2.78(1H, t), 2.79(1H, brs), 3.22(1H, brs), 3.93(3H, s), 4.26(1H, brs), 4.89(1H, brs), 5.81(1H, s), 6.78(1H, d), 6.90–7.01(5H, m), 7.09–7.17(5H, m), 7.30–7.34 (2H, m), 7.62(1H, d) | C$_{27}$H$_{27}$NO$_4$·1/4 H$_2$O<br>　　　C　　H　　N<br>Calcd; 74.72 6.39 3.23<br>Found; 74.69 6.28 2.94 |

TABLE 1-continued

| Compound no. | Chemical structure | Properties m.p. (recrystallization solvent) | IR | $^1$H-NMR (CDCl$_3$) | Elemental analysis |
|---|---|---|---|---|---|
| 6 | (structure: MeO, HO-phenyl-CH=CH-C(O)-N-tetrahydropyridine-phenyl-O-phenyl) | Colorless crystals 87–88° C. (ethyl acetate/hexane) | (CHCl$_3$) 3020, 2402, 1641, 1590, 1508, 1490, 1438, 1376, 1034, 931 | 2.62(2H, m), 3.89(2H, m), 3.94(3H, s), 4.35(2H, m), 5.77(1H, s), 6.04(1H, m), 6.70–7.45(13H, m), 7.64(1H, d) | — |
| 7 | (structure: MeO, HO-phenyl-CH=CH-C(O)-N-piperazine-N-CH$_2$-phenyl-F) | Colorless crystals 137–138° C. (ethyl acetate/hexane) | (CHCl$_3$) 2364, 1644, 1609, 1513, 1456 | 3.19(4H, t), 3.84(4H, m), 3.88(2H, s), 3.94(3H, s), 5.77(1H, s), 6.74(1H, d), 6.86–7.00(6H, m), 7.07–7.14 (5H, m), 7.63(1H, d) | C$_{27}$H$_{27}$N$_3$O$_3$·1/2 H$_2$O<br>　　C　　H　　N<br>Calcd: 71.19 6.39 6.15<br>Found: 70.92 6.11 6.16 |
| 8 | (structure: HN-tetrahydropyridine-phenyl-O-phenyl) | Colorless crystals 186–189° C. (methylene chloride/ether) | (CHCl$_3$) 3024, 3018, 1674, 1606, 1508, 1489, 1243 | 2.45(2H, td), 3.11(1H, t), 3.53(2H, dd), 6.09(1H, m), 6.94–7.13(5H, m), 7.29–7.39 (4H, m) | — |
| 9 | (structure: HN-piperidine-phenyl-O-phenyl) | Colorless crystals (hydrochloride) 84–87° C. (methylene chloride/ether) | (KBr) (hydrochloride) 3024, 2960, 2712, 1590, 1508, 1489, 1241, 1280 | 1.61(2H, ddd), 1.83(2H, d), 2.60(1H, t), 2.74(2H, td), 3.18(2H, d), 6.94(2H, d), 7.00(2H, d), 7.07(1H, t), 7.17(2H, d), 7.31(2H, t) | — |
| 10 | (structure: HN-piperazine-N-CH$_2$-phenyl-F) | Colorless crystals (dihydrochloride) 139–141° C. (methanol/ether) | (KBr) (dihydrochloride) 3426, 3410, 3000, 2636, 2480, 1602, 1508, 1221, 1158 | 3.03(4H, dd), 3.11(4H, dd), 3.87(2H, s), 6.83–7.14(8H, m) | — |

TABLE 1-continued

| Compound no. | Chemical structure | Properties m.p. (recrystall- ization solvent) | IR | ¹H-NMR (CDCl₃) | Elemental analysis |
|---|---|---|---|---|---|
| 11 | (4-F-C₆H₄-CH₂-C₆H₄-tetrahydropyridine) | Pale yellow crystals | (CHCl₃) 3020, 2926, 2993, 1604, 1508, 1434, 1157, 1016, 930 | 2.43(2H, td), 3.09(2H, t), 3.51(2H, dd), 3.92(2H, s), 6.10(1H, m), 6.94–6.98(2H, m), 7.10–7/15(4H, m), 7.31(2H, d) | — |
| 12 | (4-F-C₆H₄-CH₂-C₆H₄-piperidine) | An oily substance | (CHCl₃) 2930, 2337, 1603, 1508, 1446, 1318, 1016, 862, 820 | 1.57–1.66(2H, m), 1.83(2H, d), 2.58(1H, tt), 2.73(2H, td), 3.17(2H, d), 3.91(2H, s), 6.94–6.97(2H, m), 7.08–7.18 (6H, m) | — |
| 13 | (4-F-C₆H₄-CH₂-C₆H₄-tetrahydropyridine) | An oily substance | (CHCl₃) 2924, 1604, 1508, 1436, 1157, 1093 | 2.45(2H, m), 3.1(2H, t), 3.52(2H, m), 3.94(2H, s), 6.09(1H, t), 6.9–7.35(8H, m) | — |
| 14 | (4-F-C₆H₄-CH₂-C₆H₄-piperidine) | An oily substance | (CHCl₃) 2938, 1606, 1508, 1446, 1318, 1157, 1094, 928 | 1.66(2H, m), 1.83(2H, m), 2.6(1H, tt), 2.75(2H, td), 3.2(2H, m), 3.96(2H, s), 6.9–7.4(8H, m) | — |

TABLE 1-continued

| Compound no. | Chemical structure | Properties m.p. (recrystall- ization solvent) | IR | ¹H-NMR (CDCl₃) | Elemental analysis |
|---|---|---|---|---|---|
| 15 | 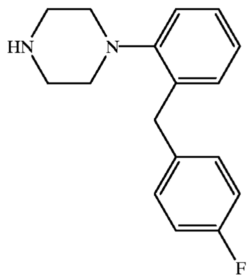 | An oily substance | (CHCl₃) 3020, 2400, 1508, 1489, 1156, 1135, 932, 848 | 2.80(4H, dd), 2.96(4H, dd), 4.04(2H, s), 6.91–7.23(8H, m) | — |
| 16 | 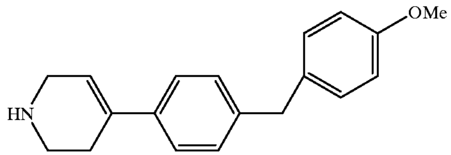 | Colorless crystals | (CHCl₃) 3020, 1508, 1226, 1212, 1208, 775, 768, 758, 752, 732 | 2.43(2H, m), 3.09(2H, t), 3.51(2H, dd), 3.78(3H, s), 3.90(2H, s), 6.09(H, bs), 6.82(2H, d), 7.12(4H, dd), 7.29(2H, d) | — |
| 17 | 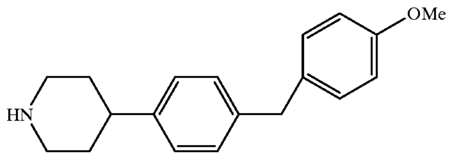 | An oily substance | (CHCl₃) 3023, 1654, 1560, 1508, 1227, 1203, 799, 722 | 1.62(2H, d), 1.81(2H, d), 2.57(1H, tt), 2.72(2H, dt), 3.17(2H, m), 3.77(3H, s), 3.89(2H, s), 6.82(2H, d), 7.09–7.14(6H, m) | — |
| 18 | 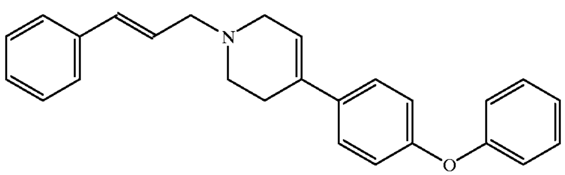 | Colorless crystals (hydrochloride) 202–205° C. (methanol/ ether) | (KBr) (hydrochloride) 2482, 1588, 1508, 1486, 1236, 1173, 980, 867, 821, 750, 692 | 2.59(2H, d), 2.78(2H, t), 3.22(2H, dd), 3.30(2H, dd), 6.03(1H, m), 6.36(1H, d), 6.58(1H, d), 6.96(2H, dd), 7.01(2H, d), 7.10(1H, t), 7.24–7.41(9H, m) | $C_{20}H_{24}ClNO$ (hydrochloride). 1/4 $H_2O$<br>　　　　C　　H　　N<br>Calcd: 76.46 6.54 3.43<br>Found: 76.19 6.41 3.48 |

TABLE 1-continued

| Compound no. | Chemical structure | Properties m.p. (recrystall-ization solvent) | IR | $^1$H-NMR (CDCl$_3$) | Elemental analysis |
|---|---|---|---|---|---|
| 19 | (structure) | Yellow crystals (hydrochloride) 103–106° C. (methanol/ether) | (KBr) (hydrochloride) 2934, 1653, 1594, 1508, 1490, 1281, 1234, 1170, 1124, 1032, 871, 749, 692 | 1.77–1.85(4H, m), 2.10(2H, dt), 2.53(1H, t), 3.13–3.19(4H, m), 3.90(3H, s), 5.66(1H, brs), 6.17(1H, dt), 6.46(1H, d), 6.86–7.00(6H, m), 7.07(1H, t), 7.18(2H, d), 7.29–7.33(2H, m) | C$_{27}$H$_{26}$ClNO$_2$(hydrochloride). 7/5 H$_2$O<br>C H N<br>Calcd; 67.96 6.93 2.94<br>Found: 67.88 6.66 2.94 |
| 20 | (structure) | Colorless crystals (hydrochloride) 103–106° C. (methanol/ether) | (KBr) (hydrochloride) 2936, 2700, 2594, 1589, 1509, 1492, 1243, 1053, 827 | 2.59(2H, m), 2.85(2H, t), 2.93(2H, t), 3.3(2H, dd), 4.14(2H, t), 6.02(1H, t), 6.8–7.15(9H, m), 7.32(2H, d), 7.36(2H, d) | C$_{26}$H$_{26}$ClFNO$_2$(hydrochloride)<br>C H N<br>Calcd; 70.50 5.92 3.29<br>Found: 70.01 5.78 3.30 |
| 21 | (structure) | Colorless crystals (hydrochloride) 200–204° C. (methanol/ether) | (KBr) (hydrochloride) 2930, 2526, 1654, 1589, 1504, 1490, 1239, 1170, 978, 869, 749, 693 | 1.75–1.87(4H, m), 2.10(2H, dt), 2.50(1H, tt), 3.12(2H, d), 3.20(2H, d), 6.34(1H, d), 6.55(1H, dt), 6.94(2H, d), 6.99(2H, d), 7.07(1H, t), 7.19(2H, d), 7.22–7.33(5H, m), 7.39(2H, d) | C$_{26}$H$_{26}$ClNO (hydrochloride)<br>C H N<br>Calcd; 76.92 6.95 3.45<br>Found: 76.77 6.95 3.45 |
| 22 | (structure) | Colorless crystals (hydrochloride) 199–201° C. (methanol/ether) | (KBr) (hydrochloride) 2929, 2664, 2551, 1590, 1508, 1490, 1241, 1170, 872, 842, 749, 694 | 1.84–1.94(6H, m), 2.09(2H, m), 2.44–2.53(3H, m), 2.66(2H, t), 3.10(2H, m), 6.94(2H, dd), 6.99(2H, d), 7.07(1H, t), 7.17–7.21(5H, m), 7.26–7.33 (4H, m) | C$_{26}$H$_{30}$ClNO (hydrochloride). 1/5 H$_2$O<br>C H N<br>Calcd; 75.87 7.44 3.40<br>Found: 75.84 7.32 3.40 |
| 23 | (structure) | Colorless crystals (fumarate) 156–158° C. (methanol/ether) | (KBr) (fumarate) 2939, 2497, 1715, 1590, 1496, 1294, 1100, 983, 872, 797, 696 | 1.81–1.86(4H, m), 2.10–2.16 (2H, m), 2.50(1H, tt), 3.14(2H, m), 3.23(2H, m), 3.86(3H, s), 3.869(3H, s), 3.873(3H, s), 6.24(1H, d), 6.66(1H, d), 6.74(1H, d), 6.94(2H, d), 7.00(2H, d), 7.07(1H, t), 7.18–7.34(5H, m) | C$_{33}$H$_{37}$NO$_2$ (fumarate). 1/4 H$_2$O<br>C H N<br>Calcd; 68.32 6.52 2.41<br>Found: 68.25 6.45 2.42 |

TABLE 1-continued

| Compound no. | Chemical structure | Properties m.p. (recrystall-ization solvent) | IR | ¹H-NMR (CDCl₃) | Elemental analysis |
|---|---|---|---|---|---|
| 24 | (MeO, HO-phenyl-CH=CH-CH₂-N-tetrahydropyridine-phenyl-O-phenyl) | Yellow crystals (hydrochloride) 200–204° C. (methanol/ether) | (KBr) (hydrochloride) 3424, 2932, 2586, 1654, 1594, 1511, 1484, 1280, 1172, 1125, 1032, 972, 868, 808, 756, 693 | 2.59(2H, d), 2.78(2H, t), 3.22(2H, d), 3.27(2H, d), 3.90(3H, s), 5.62(1H, brs), 6.03(1H, m), 6.19(1H, d), 6.49(1H, d), 6.84–7.36(12H, m) | $C_{27}H_{28}ClNO_3$ (hydrochloride). 3/2 $H_2O$<br>C H N<br>Calcd: 67.99 6.55 2.94<br>Found: 67.83 6.16 3.07 |
| 25 | (F-phenyl-CH=CH-CH₂-N-piperidine-phenyl-O-phenyl) | Colorless crystals (hydrochloride) 198–200° C. (methanol/ether) | (KBr) (hydrochloride) 3445, 2930, 2606, 1654, 1592, 1514, 1468, 1254, 1164, 984, 834, 747, 692 | 1.75–1.87(4H, m), 2.10(2H, dt), 2.50(1H, t), 3.12(2H, m), 3.19(2H, m), 6.24(1H, d), 6.50(1H, d), 6.94–7.02(6H, m), 7.07(1H, t), 7.18(2H, d), 7.25–7.36(4H, m) | $C_{24}H_{27}ClFNO$ (hydrochloride). 1/2 $H_2O$<br>C H N<br>Calcd: 72.13 6.52 3.24<br>Found: 72.22 6.38 3.36 |
| 26 | (phenyl-cyclopropyl-CH₂-N-piperidine-phenyl-O-phenyl) | Colorless crystals (fumarate) 158–160° C. (methanol/ether) | (KBr) (fumarate) 3034, 2944, 2532, 1718, 1596, 1511, 1260, 868, 754, 691 | 0.85(1H, ddd), 1.00(1H, ddd), 1.30(1H, m), 1.70(1H, m), 1.77–1.85(4H, m), 2.10–2.15 (2H, m), 2.42–2.51(2H, m), 2.56(1H, dd), 3.18(2H, m), 6.93(2H, d), 6.99(2H, d), 7.06–7.33(10H, m) | $C_{21}H_{39}NO_6$ (fumarate)<br>C H N<br>Calcd: 74.53 6.66 2.80<br>Found: 74.06 6.65 2.80 |
| 27 | (F-phenyl-O-CH₂CH₂-N-piperidine-phenyl-O-phenyl) | Colorless crystals (hydrochloride) 146–148° C. (methanol/ether) | (KBr) (hydrochloride) 2936, 1589, 1508, 1485, 1240, 1172, 978, 825 | 1.75–1.95(4H, m), 2.22(2H, td), 2.5(1H, m), 2.83(2H, t), 3.11(2H, d), 4.1(2H, t), 6.85(1H, d), 6.86(1H, d), 6.9(2H, d), 6.9–7.05(4H, m), 7.1(1H, t), 7.17(2H, d), 7.31(2H, t) | — |

TABLE 1-continued

| Compound no. | Chemical structure | Properties m.p. (recrystall-ization solvent) | IR | $^1$H-NMR (CDCl$_3$) | Elemental analysis |
|---|---|---|---|---|---|
| 28 | (4-fluorophenoxy-phenyl-piperidine-propoxy structure) | Colorless crystals (hydrochloride) 154–156° C. (methanol/ether) | (KBr) (hydrochloride) 2920, 2510, 1589, 1514, 1502, 1234, 1170, 1073, 870, 822, 761, 694 | 1.69–1.83(8H, m), 2.05(2H, t), 2.42–2.52(3H, m), 3.07(2H, m), 3.95(2H, t), 6.81–6.85(2H, m), 3.95(2H, t), 6.81–6.85(2H, m), 6.93–7.01(6H, m), 7.07(1H, t), 7.18(2H, d), 7.25–7.33(2H, m) | C$_{27}$H$_{31}$ClFNO$_2$ (hydrochloride) C H N Calcd; 71.12 6.86 2.98 Found; 70.90 6.80 3.09 |
| 29 | (trimethoxybenzyl-phenoxyphenyl-piperidine structure) | Colorless crystals (hydrochloride) 178–180° C. (methanol/ether) | (KBr) (hydrochloride) 2944, 2481, 1590, 1490, 1287, 1238, 1170, 1103, 870, 802, 748, 693 | 1.70–1.82(4H, m), 2.10(2H, dt), 2.48(1H, tt), 3.02(2H, m), 3.52(2H, s), 3.86(3H, s), 3.88(3H, s), 3.90(3H, s), 6.65(1H, d), 6.91–7.09(6H, m), 7.18(2H, d), 7.28–7.33(2H, m) | C$_{27}$H$_{32}$ClNO$_4$ (hydrochloride)·H$_2$O C H N Calcd; 66.45 7.02 2.87 Found; 66.56 6.65 2.89 |
| 30 | (4-fluorobenzoyl-propyl-phenoxyphenyl-piperidine structure) | Colorless crystals (hydrochloride) 194–196° C. (methanol/ether) | (KBr) (hydrochloride) 2942, 2642, 2547, 1687, 1600, 1508, 1490, 1250, 1157, 932 | 1.66–1.75(2H, m), 1.81(2H, d), 1.99(2H, dt), 2.08(2H, t), 2.43–2.50(3H, m), 3.00(2H, t), 3.05(2H, m), 6.92–6.95(2H, m), 6.98–7.00(2H, m), 7.06–7.16 (5H, m), 7.29–7.34(2H, m), 7.99–8.04(2H, m) | C$_{27}$H$_{27}$ClFNO$_2$ (hydrochloride) C H N Calcd; 71.43 6.44 3.09 Found; 71.01 6.37 3.09 |
| 31 | (cinnamyl-fluorobenzyl-phenyl-tetrahydropyridine structure) | Colorless crystals (hydrochloride) 195–197° C. (methanol/ether) | (KBr) (hydrochloride) 2930, 2666, 2448, 1599, 1511, 1502, 1451, 1218, 978, 941, 847, 803, 742, 693 | 2.58(2H, d), 2.76(2H, t), 3.21(2H, m), 3.29(2H, d), 3.92(2H, s), 6.04(1H, m), 6.35(1H, d), 6.57(1H, d), 6.96(2H, t), 7.09–7.40(12H, m) | C$_{27}$H$_{27}$ClFN (hydrochloride)·1/5 H$_2$O C H N Calcd; 76.56 6.52 3.31 Found; 76.62 6.43 3.32 |
| 32 | (cinnamyl-fluorobenzyl-phenyl-piperidine structure) | Colorless crystals (hydrochloride) 203–205° C. (methanol/ether) | (KBr) (hydrochloride) 2940, 2488, 1600, 1504, 1458, 1221, 1158, 978, 816, 752, 695 | 1.78–1.84(4H, m), 2.09(2H, dt), 2.47(1H, tt), 3.11(2H, m), 3.19(2H, dd), 3.91(2H, s), 6.33(1H, dt), 6.53(1H, d), 6.93–6.98(2H, m), 7.07–7.40(11H, m) | C$_{27}$H$_{29}$ClFN (hydrochloride) C H N Calcd; 76.85 6.93 3.32 Found; 76.76 6.86 3.33 |

TABLE 1-continued

| Compound no. | Chemical structure | Properties m.p. (recrystall- ization solvent) | IR | $^1$H-NMR (CDCl$_3$) | Elemental analysis |
|---|---|---|---|---|---|
| 33 | 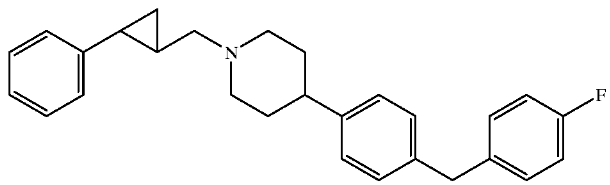 | Colorless crystals (hydrochloride) 176–178° C. (methanol/ ether) | (KBr) (hydrochloride) 2929, 2500, 1604, 1512, 1504, 1457, 1222, 1158, 820, 755, 700 | 0.85(1H, ddd), 0.97(1H, ddd), 1.29(1H, m), 1.70(1H, m), 1.81(4H, m), 2.12(2H, m), 2.44(2H, m), 2.52(1H, m), 3.17(2H, m), 3.91(2H, s), 6.96(1H, t), 7.05–7.15(7H, m), 7.23–7.27(3H, m) | C$_{28}$H$_{31}$ClFN (hydrochloride). 1/4 H$_2$O<br>C  H  N<br>Calcd; 76.34 7.21 3.18<br>Found; 76.28 7.10 3.24 |
| 34 | 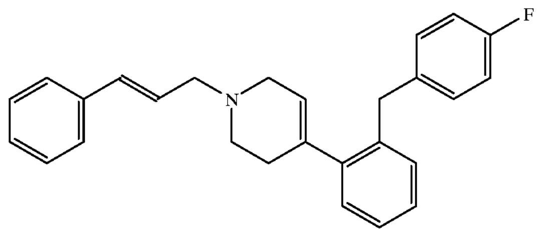 | Colorless crystals (hydrochloride) 160–162° C. (methanol/ ether) | (KBr) (hydrochloride) 3498, 2908, 2506, 1654, 1508, 1448, 1126, 1156, 973 | 2.35(2H, m), 2.75(2H, t), 3.2(2H, m), 3.35(2H, d), 4.00(2H, s), 5.52(1H, m), 6.41(1H, dr), 6.61(1H, d), 6.9–7.6(13H, m) | C$_{27}$H$_{27}$ClFN (hydrochloride)<br>C  H  N<br>Calcd; 77.22 6.48 3.34<br>Found; 76.98 6.47 3.34 |
| 35 | 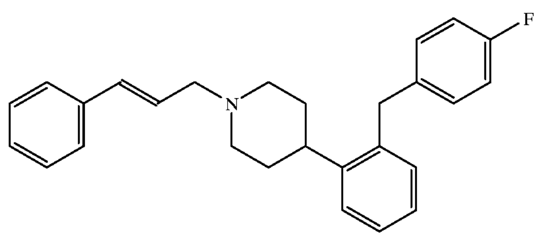 | Colorless crystals (hydrochloride) 200–202° C. (methanol/ ether) | (KBr) (hydrochloride) 3436, 2942, 2530, 1602, 1508, 1450, 1436, 1220, 1158, 978 | 1.7–2.1(4H, m), 2.75(2H, m), 3.07(2H, m), 3.16(2H, d), 3.4(2H, m), 4.05(2H, s), 6.25(1H, dt), 6.56(1H, d), 6.8–7.5(13H, m) | C$_{27}$H$_{29}$ClFN (hydrochloride)<br>C  H  N<br>Calcd; 76.85 6.93 3.32<br>Found; 76.45 6.93 3.28 |
| 36 | 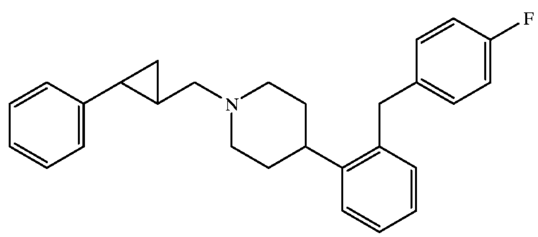 | Colorless foam (hydrochloride) | (KBr) (hydrochloride) 3388, 3030, 2935, 2656, 2524, 1604, 1508, 1456, 1220, 1156, 957 | 0.85(1H, dt), 0.97(1H, dt), 1.27(1H, m), 1.47–1.6(4H, m), 1.67(1H, m), 1.7–2.04(2H, m), 2.4(1H, dd), 2.52(1H, m), 2.66(1H, m), 3.1(2H, m), 4.02(1H, d), 6.85–7.35(13H, m) | — |

TABLE 1-continued

| Compound no. | Chemical structure | Properties m.p. (recrystallization solvent) | IR | ¹H-NMR (CDCl₃) | Elemental analysis |
|---|---|---|---|---|---|
| 37 | (4-fluorobenzyl-phenyl-piperidine-cinnamyl structure) | A colorless oil (hydrochloride) | (KBr) (hydrochloride) 2944, 2512, 1607, 1508, 1451, 1216, 1094, 989 | 2.6(2H, m), 2.78(2H, t), 3.2–3.4(4H, m), 3.97(2H, s), 6.06(1H, brs), 6.35(1H, dt), 6.59(1H, d), 6.9–7.5(9H, m) | — |
| 38 | (4-fluorobenzyl-phenyl-piperidine-cinnamyl structure) | Colorless crystals (hydrochloride) 190–192° C. (methanol/ether) | (KBr) (hydrochloride) 2944, 2512, 1607, 1508, 1451, 1216, 1158, 989 | 1.8(4H, m), 2.07(2H, m), 2.47(1H, m), 3.11(2H, m), 3.29(2H, d), 3.91(2H, s), 6.33(1H, dt), 6.53(1H, d), 6.9–7.5(13H, m) | C₂₇H₂₉ClFN (hydrochloride) C H N Calcd; 76.85 6.93 3.32 Found; 76.77 6.88 3.34 |
| 39 | (4-fluorobenzyl-phenyl-piperidine-cyclopropyl structure) | Colorless foam (hydrochloride) | (KBr) (hydrochloride) 3446, 2940, 2658, 2526, 1604, 1508, 1436, 1219, 1157, 1094 | 0.87(1H, d), 1.0(1H, d), 1.31(1H, m), 1.72(1H, m), 1.84(4H, m), 2.25(2H, m), 2.43(1H, dd), 2.47(1H, m), 2.52(1H, dd), 3.2(2H, m), 3.94(2H, s), 6.9–7.4(13H, m) | — |
| 40 | (phenoxyphenyl-piperazine-cinnamyl structure) | Colorless crystals (dihydrochloride) 205–207° C. (methanol/ether) | (KBr) (dihydrochloride) 2402, 1590, 1510, 1490, 1456, 1250, 1171, 960, 750, 693 | 2.69(4H, m), 3.20(4H, m), 3.23(2H, d), 6.31(1H, dt), 6.57(1H, d), 6.90–7.04(7H, m), 7.23–7.33(5H, m), 7.39(2H, d) | C₂₆H₂₈Cl₂N₂O (hydrochloride). 2/5 H₂O C H N Calcd; 66.64 6.44 6.22 Found; 66.66 6.14 6.24 |
| 41 | (phenoxyphenyl-piperazine-butoxy-fluorophenyl structure) | Colorless crystals (dihydrochloride) 173–175° C. (methanol/ether) | (KBr) (dihydrochloride) 2984, 2354, 1588, 1504, 1490, 1456, 1250, 1208, 829, 756 | 1.71(2H, tt), 1.82(2H, tt), 2.47(2H, t), 2.62(4H, t), 3.16(4H, t), 3.96(2H, t), 6.82(1H, d), 6.83(1H, d), 6.90–6.98(8H, m), 7.02(1H, t), 7.26(1H, d), 7.29(1H, d) | C₂₆H₃₁Cl₂CN₂O₂(hydrochloride) C H N Calcd; 63.29 6.33 5.68 Found; 63.12 6.22 5.68 |

TABLE 1-continued

| Compound no. | Chemical structure | Properties m.p. (recrystall- ization solvent) | IR | ¹H-NMR (CDCl₃) | Elemental analysis |
|---|---|---|---|---|---|
| 42 | 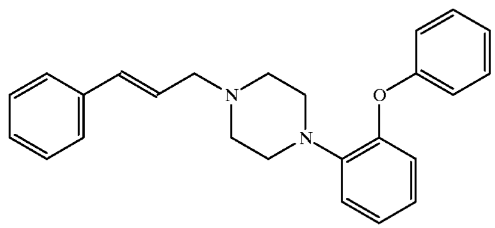 | Colorless crystals (dihydrochloride) 140–142° C. (methanol/ether) | (KBr) (dihydro- chloride) 2960, 2380, 1590, 1494, 1446, 1235, 1171, 978, 951, 750 | 2.49(4H, m), 3.13(2H, d), 3.14(4H, t), 6.25(1H, dt), 6.49(1H, d), 6.91–6.98(4H, m), 7.03(2H, t), 7.08–7.12(1H, m), 7.21–7.31(5H, m), 7.36(2H, d) | $C_{26}H_{28}Cl_2N_2O$ (hydrochloride). 1/4 $H_2O$    C    H    N Calcd: 67.04 6.41 6.25 Found: 67.01 6.28 6.26 |
| 43 | 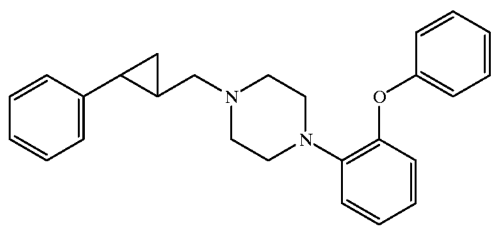 | Colorless crystals (dihydrochloride) 123–125° C. (methanol/ether) | (KBr) (dihydro- chloride) 3012, 2360, 1588, 1492, 1448, 1256, 202, 969, 750, 694 | 0.80(1H, ddd), 0.93(1H, ddd), 1.22(1H, m), 1.65(1H, m), 2.32(1H, dd), 2.47(1H, dd), 2.51(4H, m), 3.12(4H, t), 6.90–7.15(10H, m), 7.22–7.28 (4H, m) | $C_{26}H_{30}Cl_2N_2O$ (hydrochloride). 1/5 $H_2O$    C    H    N Calcd: 67.73 6.65 6.08 Found: 67.79 6.50 6.12 |
| 44 | 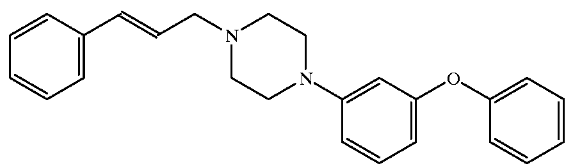 | Colorless crystals (dihydrochloride) 148–150° C. (methanol/ether) | (KBr) (dihydro- chloride) 2375, 1591, 1488, 1260, 1210, 980, 949, 778, 753, 688 | 2.64(4H, t), 3.21(2H, d), 3.22(4H, t), 6.29(1H, dt), 6.46(1H, dd), 6.55(1H, d), 6.61(1H, dd), 6.67(1H, dd), 7.01(1H, t), 7.07(1H, t), 7.16–7.25(5H, m), 7.31(1H, t), 7.39(2H, d) | $C_{26}H_{27}Cl_2N_2O$ (hydrochloride). 1/4 $H_2O$    C    H    N Calcd: 67.04 6.41 6.25 Found: 66.92 6.31 6.25 |
| 45 | 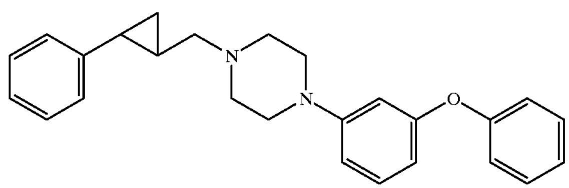 | Colorless crystals (dihydrochloride) 172–174° C. (methanol/ether) | (KBr) (dihydro- chloride) 2530, 2346, 1580, 1515, 1485, 1220, 954, 748, 698 | 0.85(1H, ddd), 0.98(1H, ddd), 1.26(1H, m), 1.70(1H, m), 2.39(1H, dd), 2.59(1H, m), 2.66(4H, m), 3.19(4H, t), 6.45(1H, dd), 6.59(1H, s), 6.65(1H, d), 6.99–7.33(11H, m) | — |

TABLE 1-continued

| Compound no. | Chemical structure | Properties m.p. (recrystallization solvent) | IR | ¹H-NMR (CDCl₃) | Elemental analysis |
|---|---|---|---|---|---|
| 46 | (structure: 2,3,4-trimethoxycinnamyl-piperazine-4-phenoxyphenyl) | Colorless crystals (dihydrochloride) 166–169° C. (methanol/ether) | (KBr) (dihydrochloride) 2987, 2438, 1661, 1491, 1421, 1292, 1236, 1201, 1096, 871, 754 | 2.64(4H, t), 3.15(4H, t), 3.54(2H, s), 3.86(3H, s), 3.88(3H, s), 3.90(3H, s), 6.66(1H, d), 6.91–6.96(5H, m), 7.00–7.04(2H, m), 7.26–7.30 (2H, m) | $C_{26}H_{24}Cl_2N_2O_4$ (hydrochloride)<br>C H N<br>Calcd; 61.30 6.73 5.50<br>Found; 61.22 6.25 5.51 |
| 47 | (structure: 2,3-dimethoxycinnamyl-piperazine-4-(4-fluorobenzyl)phenyl) | Colorless crystals (dihydrochloride) 180–182° C. (methanol/ether) | (KBr) (dihydrochloride) 2370, 1603, 1597, 1510, 1508, 1458, 1223, 966, 820, 754, 695 | 2.66(4H, t), 3.19(4H, t), 3.21(2H, d), 3.86(2H, s), 3.90(3H, s), 6.55(1H, d), 6.30(1H, d), 6.94(2H, t), 6.86(2H, d), 6.94(2H, t), 7.05(2H, d), 7.11(2H, dd), 7.23(1H, t), 7.31(2H, t), 7.38(2H, d) | $C_{26}H_{29}Cl_2FN_2$ (hydrochloride)<br>C H N<br>Calcd; 67.97 6.36 6.10<br>Found; 67.80 6.27 6.10 |
| 48 | (structure: 2,3-dimethoxycinnamyl-piperazine-4-(4-fluorobenzyl)phenyl with OMe) | Colorless crystals (dihydrochloride) 168–170° C. (methanol/ether) | (KBr) (dihydrochloride) 2934, 2365, 1597, 1510, 1494, 1460, 1418, 1298, 1222, 1098, 1060, 1016, 948, 813 | 2.66(4H, t), 3.19(4H, t), 3.22(2H, d), 3.86(2H, s), 3.866(5H, s), 3.871(3H, s), 6.20(1H, dt), 6.66(1H, d), 6.75(1H, d), 6.86(2H, d), 6.94(2H, t), 7.05(2H, d), 7.11(2H, dd), 7.18(1H, d) | $C_{29}H_{25}Cl_2FN_2O_3$ (hydrochloride)<br>C H N<br>Calcd; 63.40 6.42 5.10<br>Found; 63.75 6.39 5.23 |
| 49 | (structure: 3-methoxy-4-hydroxycinnamyl-piperazine-4-(4-fluorobenzyl)phenyl) | Yellow crystals (dihydrochloride) 115–117° C. (methanol/ether) | (KBr) (dihydrochloride) 3134, 2544, 1602, 1514, 1456, 1279, 1220, 1159, 1122, 1032, 808 | 2.66(4H, t), 3.19(2H, d), 3.20(4H, t), 3.86(2H, s), 3.89(3H, s), 5.67(2H, brs), 6.14(1H, dt), 6.47(1H, d), 6.84–6.88(4H, m), 6.94(3H, m), 7.05(2H, d), 7.11(2H, dd) | — |
| 50 | (structure: 4-fluorocinnamyl-piperazine-4-(4-fluorobenzyl)phenyl) | Colorless crystals (dihydrochloride) 148–150° C. (methanol/ether) | (KBr) (dihydrochloride) 2364, 1602, 1510, 1436, 1228, 1158, 962, 830 | 2.65(4H, t), 3.19(4H, t), 3.20(2H, d), 3.86(2H, s), 6.21(1H, d), 6.51(1H, d), 6.86(2H, dd), 6.92–7.13 (10H, m), 7.34(2H, dd) | $C_{26}H_{23}Cl_2F_2N_2$ (hydrochloride)<br>C H N<br>Calcd; 65.41 5.91 5.87<br>Found; 65.52 5.81 5.87 |

TABLE 1-continued

| Compound no. | Chemical structure | Properties m.p. (recrystallization solvent) | IR | ¹H-NMR (CDCl₃) | Elemental analysis |
|---|---|---|---|---|---|
| 51 | 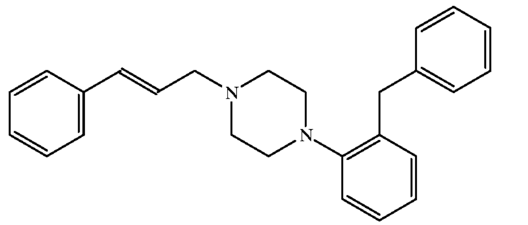 | Colorless crystals (dihydrochloride) 145–147° C. (methanol/ether) | (KBr) (dihydrochloride) 3028, 2339, 1598, 1494, 1449, 1367, 1239, 1169, 1070, 1029, 964, 744, 700 | 2.63(4H, m), 2.29(4H, t), 3.22(2H, d), 4.08(2H, s), 6.31(1H, dt), 6.55(1H, d), 7.02(1H, dd), 7.10(1H, d), 7.16–7.29(8H, m), 7.31(2H, d), 7.38(2H, d) | — |
| 52 | 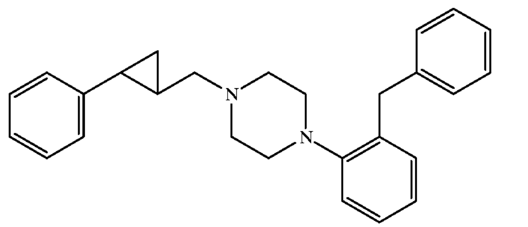 | Colorless crystals (dihydrochloride) 93–95° C. (methanol/ether) | (KBr) (dihydrochloride) 3354, 2957, 2468, 2368, 1604, 1496, 1463, 1226, 1087, 1030, 972, 940, 761, 697 | 0.86(1H, ddd), 0.98(1H, m), 1.28(1H, m), 1.70(1H, m), 2.43(1H, dd), 2.56(1H, dd), 2.66(4H, m), 2.90(4H, t), 4.07(2H, s), 6.99–7.27(14H, m) | $C_{27}H_{32}Cl_2N_2$ (hydrochloride)<br>C H N<br>Calcd; 71.20 7.08 6.15<br>Found; 70.77 7.16 6.19 |
| 53 | 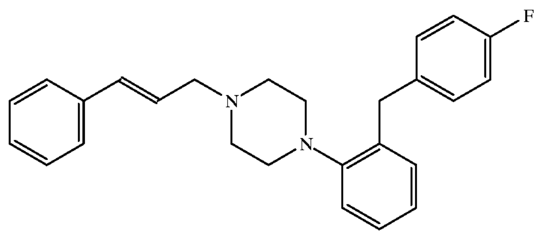 | Colorless crystals (dihydrochloride) 136–138° C. (methanol/ether) | (KBr) (dihydrochloride) 3416, 2921, 2368, 1600, 1509, 1493, 1451, 1222, 1158, 968, 768, 744, 692 | 2.63(4H, m), 2.90(4H, m), 3.22(2H, d), 4.03(2H, s), 6.31(1H, dt), 6.55(1H, d), 6.94(2H, dt), 7.01–7.21 (2H, m), 7.23–7.26(5H, m), 7.31(2H, t), 7.39(2H, d) | — |
| 54 | 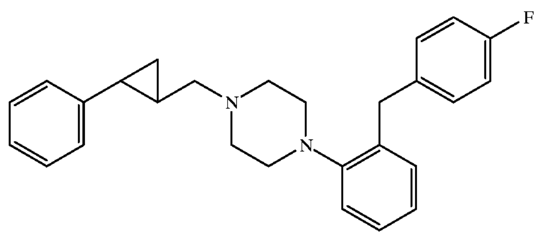 | Colorless crystals (dihydrochloride) 108–110° C. (methanol/ether) | (KBr) (dihydrochloride) 3416, 2921, 2586, 1601, 1508, 1456, 1224, 1158, 764, 700 | 0.85(1H, ddd), 0.98(1H, m), 1.28(1H, m), 1.70(1H, m), 2.43(1H, dd), 2.58(1H, dd), 2.65(4H, m), 2.89(4H, t), 4.02(2H, s), 6.92(2H, t), 7.03(2H, dd), 7.06(2H, d), 7.11–7.27(7H, m) | $C_{27}H_{31}Cl_2FN_2$ (hydrochloride)<br>C H N<br>Calcd; 68.50 6.60 5.92<br>Found; 69.00 6.50 6.03 |

TABLE 1-continued

| Compound no. | Chemical structure | Properties m.p. (recrystall- ization solvent) | IR | ¹H-NMR (CDCl₃) | Elemental analysis |
|---|---|---|---|---|---|
| 55 | (4-fluorobenzyl piperazine with phenylcyclopropylmethyl substituent) | Colorless crystals (fumarate) 160–162° C. (methanol/ether) | (KBr) (fumarate) 3011, 2930, 2570, 1714, 1576, 1558, 1513, 1436, 1225, 1157, 977, 811, 758, 697 | 0.85(1H, ddd), 0.98(1H, ddd), 1.27(1H, m), 1.70(1H, m) 2.40(1H, dd), 2.60(1H, dd), 2.69(4H, ddd), 3.17(4H, t), 3.86(2H, s), 6.85(2H, d), 6.94(2H, t), 7.05(4H, t), 7.09–7.16(3H, m), 7.25(2H, t) | C₃₁H₃₃FN₂O₄ (fumarate). 3/5 H₂O<br>C H N<br>Calcd; 70.60 6.54 5.31<br>Found; 70.67 6.35 5.33 |
| 56 | (trimethoxybenzyl piperazine with 4-fluorophenyl) | Colorless crystals (dihydrochloride) 192–194° C. (methanol/ether) | (KBr) (dihydro- chloride) 3420, 2943, 2358, 1602, 1504, 1288, 1158, 1106, 959, 812 | 2.62(4H, t), 3.15(4H, t), 3.53(2H, s), 3.86(3H, s), 3.88(5H, s), 3.89(3H, s), 6.65(1H, d), 6.84(2H, d), 6.90–7.08(5H, m), 7.11(2H, dd) | C₂₇H₃₃Cl₂FN₂O₃(hydrochloride). 1/2 H₂O<br>C H N<br>Calcd; 60.90 6.44 5.26<br>Found; 60.71 6.13 5.27 |
| 57 | (4-fluorobenzyl-phenyl-piperazine-propoxy-4-fluorophenyl) | Colorless crystals (dihydrochloride) 135–137° C. (methanol/ether) | (KBr) (dihydro- chloride) 2987, 2338, 1602, 1511, 1505, 1475, 1458, 1248, 1222, 836, 757 | 1.63–1.87(4H, m), 2.45(2H, t), 2.60(4H, t), 3.17(4H, t), 3.87(2H, s), 3.95(2, t), 6.81–6.88(4H, m), 6.96(4H, dt), 7.04–7.15(4H, m) | C₂₇H₃₂Cl₂F₂N₂O (hydrochloride)<br>C H N<br>Calcd; 63.65 6.50 5.50<br>Found; 63.89 6.27 5.55 |
| 58 | (4-fluorobenzyl-phenyl-piperazine-butanone-4-fluorophenyl) | Colorless crystals (dihydrochloride) 159–161° C. (methanol/ether) | (KBr) (dihydro- chloride) 2987, 2337, 1688, 1598, 1511, 1503, 1437, 1214, 1157, 991, 819 | 1.98(2H, m), 2.46(2H, t), 2.58(4H, t), 3.00(2H, t), 3.11(4H, t), 3.86(2H, s), 6.83(2H, d), 6.94(2H, t), 7.04(2H, d), 7.11(2H, d), 7.13(2H, d), 7.99(2H, d), 8.01(2H, d) | — |

TABLE 1-continued

| Compound no. | Chemical structure | Properties m.p. (recrystall-ization solvent) | IR | $^1$H-NMR (CDCl$_3$) | Elemental analysis |
|---|---|---|---|---|---|
| 59 | (structure: 4-phenoxyphenyl-piperidine with N-CH$_2$-C(cyclopropyl)(phenyl)) | Colorless crystals (hydrochloride) 181–182° C. (ether/methylene chloride) | (KBr) (hydrochloride) 3428, 3028, 2927, 2638, 2544, 1589, 1508, 1490, 1433, 1239, 1166, 966 | 0.79(2H, dd), 0.95(2H, dd), 1.55–1.85(4H, m), 2.12(2H, td), 2.43(1H, tt), 2.62(2H, s), 3.1(2H, m), 6.9–7.5(14H, m) | C$_{27}$H$_{20}$ClNO (hydrochloride) C H N Calcd; 77.21 7.20 3.34 Found; 76.89 7.19 3.34 |
| 60 | (structure: 4-phenoxyphenyl-piperidine with N-Et) | Colorless crystals (hydrochloride) 148–150° C. (methanol/ether) | (CHCl$_3$) 3019, 2399, 2360, 1634, 1510, 1488, 1418, 930, 870 | 1.54(3H, t), 2.06–2.09(2H, m), 2.65(2H, m), 2.79–2.28(3H, m), 3.09(2H, q), 3.64–3.60(2H, m), 6.96–7.35(9H, m) | — |
| 61 | (structure: 4-fluorobenzyl-phenyl-piperazine with N-Me) | Colorless crystals (dihydrochloride) 133–135° C. (methanol/ether) | (CHCl$_3$) 2943, 2364, 1614, 1509, 1456, 1378, 1290, 1156, 1007, 924, 816 | 2.34(3H, s), 2.56(4H, t), 3.17(4H, t), 3.86(2H, s), 6.86(2H, d), 6.92–6.99(2H, m), 7.05(2H, d), 7.10–7.13(2H, m) | C$_{13}$H$_{23}$Cl$_2$FN$_2$(hydrochloride) 5/4 H$_2$O C H N Calcd; 60.51 6.49 7.84 Found; 57.02 6.49 7.37 |
| 62 | (structure: 4-fluorobenzyl-pyridine with cyclohexyl-CH$_2$-C(cyclopropyl)(phenyl)) | Colorless crystals (hydrochloride) 188–190° C. (methylene chloride/ether) | (KBr) (hydrochloride) 3428, 2930, 2546, 1602, 1508, 1436, 1222, 1155, 968, 813, 759, 701 | 0.74(2H, dd), 0.87(2H, dd), 1.60–1.71(4H, m), 2.00(2H, dt), 2.38(1H, tt), 2.59(2H, s), 3.07(2H, s), 3.90(2H, s), 7.05–7.38(13H, m) | C$_{22}$H$_{31}$ClFN(hydrochloride) 1/5 H$_2$O C H N Calcd; 76.50 7.20 3.19 Found; 76.64 7.37 3.17 |

TABLE 1-continued

| Compound no. | Chemical structure | Properties m.p. (recrystall- ization solvent) | IR | $^1$H-NMR (CDCl$_3$) | Elemental analysis |
|---|---|---|---|---|---|
| 63 | [4-fluorobenzyl-phenyl-piperidine-N-CH$_2$-C(O)-phenyl structure] | Colorless crystals (hydrochloride) 179–181° C. (methanol/ether) | (KBr) (hydrochloride) 3402, 2928, 2620, 2544, 1694, 1599, 1508, 1450, 1225, 962, 755, 690 | 1.81–196(4H, m), 2.30(2H, dt), 2.51(1H, tt), 3.14(2H, m), 3.88(2H, s), 3.92(2H, m), 6.94–8.03(13H, m) | C$_{26}$H$_{27}$ClFNO (hydrochloride). 1/3 H$_2$O    C    H    N Calcd; 72.64 6.49 6.26 Found; 72.52 6.35 3.30 |
| 64 | [4-phenoxyphenyl-piperidine-N-CH$_2$-C(O)-phenyl structure] | Colorless crystals (hydrochloride) 183–185° C. (methanol/ether) | (KBr) (hydrochloride) 3391, 2948, 2537, 1703, 1590, 1508, 1490, 1450, 1248, 755, 691 | 1.82–1.95(4H, m), 2.30(2H, dt), 2.52(1H, tt), 3.13(2H, m), 3.85(2H, s), 6.94(2H, dd), 7.00(2H, d), 7.08(1H, t), 7.19(2H, d), 7.32(2H, m), 7.47(2H, t), 7.57(1H, t), 8.03(2H, d) | C$_{25}$H$_{26}$ClNO$_2$ (hydrocloride). 1/4 H$_2$O    C    H    N Calcd; 72.80 6.48 3.40 Found; 72.75 6.36 3.43 |
| 65 | [4-fluorobenzyl-phenyl-piperidine-cyclopropyl-phenyl structure] | Colorless crystals (hydrochloride) 223–225° C. (methanol/ether) | (KBr) (hydrochloride) 2931, 2528, 1601, 1508, 1445, 1220, 1157, 969, 819, 748, 694 | 1.80–1.83(4H, m), 2.10(2H, d), 2.42–2.55(5H, m), 3.09(2H, m), 3.91(2H, s), 6.20–6.26(1H, m), 6.44(1H, m), 6.94–7.36(13H, m) | C$_{27}$H$_{31}$ClFN (hydrochloride) 1/5 H$_2$O    C    H    N Calcd; 76.50 7.20 3.19 Found; 76.70 7.11 3.21 |
| 66 | [4-phenoxyphenyl-piperidine-N-CH$_2$-C(O)-4-methoxyphenyl structure] | Colorless crystals (hydrochloride) 196–198° C. (methanol/ether) | (KBr) (hydrochloride) 3444, 2936, 1681, 1601, 1508, 1490, 1237, 1173, 964, 832 | 1.82–1.99(4H, m), 2.32(2H, d), 2.52(1H, tt), 3.13(2H, m), 3.80(2H, s), 3.87(3H, s), 6.94(4H, d), 6.99(2H, dd), 7.07(1H, t), 7.19(2H, dd), 7.31(2H, t), 8.04(2H, dd) | C$_{21}$H$_{28}$ClNO$_3$ (hydrochloride)    C    H    N Calcd; 71.30 6.44 3.20 Found; 70.72 6.61 3.18 |

TABLE 1-continued

| Compound no. | Chemical structure | Properties m.p. (recrystall-ization solvent) | IR | $^1$H-NMR (CDCl$_3$) | Elemental analysis |
|---|---|---|---|---|---|
| 67 | (4-fluorophenacyl-piperidine-4-phenyl-O-phenyl) | Colorless crystals (hydrochloride) 185–186° C. (methanol/ether) | (KBr) (hydrochloride) 3484, 2930, 2646, 1692, 1600, 1510, 1492, 1250, 1237, 760 | 1.82–1.84(4H, m), 2.29(2H, dt), 2.51(1H, tt), 3.09(2H, m), 3.78(2H, s), 6.94(2H, dd), 6.99(2H, d), 7.07(1H, t), 7.12(2H, d), 7.17(2H, t), 7.31(2H, dt), 8.10(2H, dd) | C$_{26}$H$_{26}$ClFNO$_2$ (hydrochloride)<br>C H N<br>Calcd; 70.50 5.92 3.29<br>Found; 70.22 5.88 3.29 |
| 68 | (4-chlorophenacyl-piperidine-4-phenyl-O-phenyl) | Colorless crystals (hydrochloride) 175–176° C. (methanol/ether) | (KBr) (hydrochloride) 3418, 2946, 1694, 1590, 1510, 1488, 1403, 1242, 962, 871 | 1.79–1.87(4H, m), 2.28(2H, dt), 2.53(1H, tt), 3.07(2H, m), 3.77(2H, s), 6.94(2H, d), 6.99(2H, d), 7.06(1H, t), 7.161(2H, d), 7.24(2H, t), 7.42(2H, d), 7.99(2H, d) | C$_{26}$H$_{25}$Cl$_2$NO$_2$ (hydrochloride)<br>C H N<br>Calcd; 67.88 5.70 3.17<br>Found; 67.59 5.62 3.13 |
| 69 | (α-methylphenacyl-piperidine-4-phenyl-O-phenyl) | Colorless crystals (hydrochloride) 202–204° C. (methanol/ether) | (KBr) (hydrochloride) 3444, 2937, 1686, 1590, 1508, 1490, 1449, 1235, 978, 704 | 1.31(3H, d), 1.65(1H, dt), 1.76(2H, dt), 1.85(1H, m), 2.29(1H, dt), 2.46(1H, tt), 2.67(1H, dt), 2.89(1H, m), 3.07(1H, m), 4.15(1H, q), 6.92(2H, dd), 6.98(2H, d), 7.06(1H, t), 7.14(2H, d), 7.28(2H, t), 7.45(2H, t), 7.55(1H, t), 8.12(2H, d) | C$_{28}$H$_{23}$ClNO$_2$ (hydrochloride)<br>C H N<br>Calcd; 74.01 6.69 3.32<br>Found; 74.12 6.87 3.31 |
| 70 | (phenacyl-piperidine-4-phenyl-CH$_2$-phenyl-OMe) | Colorless crystals (hydrochloride) 210–212° C. (methanol/ether) | (KBr) (hydrochloride) 3442, 2935, 2649, 1699, 1511, 1450, 1245, 1031, 810, 759, 690 | 1.79–1.93(4H, m), 2.28(2H, dt), 2.48(1H, tt), 3.11(2H, m), 3.77(3H, s), 3.83(2H, s), 3.88(2H, s), 6.82(2H, d), 7.08–7.15(6H, m), 7.45(2H, t), 7.56(1H, t), 8.03(2H, d) | C$_{27}$H$_{30}$ClNO$_2$ (hydrochloride)<br>C H N<br>Calcd; 74.38 6.94 3.21<br>Found; 74.19 6.93 3.18 |

TABLE 1-continued

| Compound no. | Chemical structure | Properties m.p. (recrystall- ization solvent) | IR | ¹H-NMR (CDCl₃) | Elemental analysis |
|---|---|---|---|---|---|
| 71 | 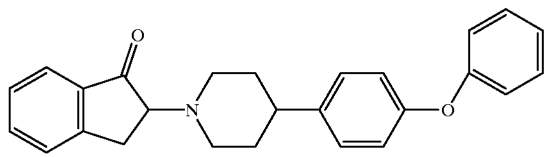 | Colorless crystals (hydrochloride) 166–167° C. | (KBr) (hydrochloride) 3464, 2608, 1721, 1608, 1588, 1511, 1584, 1236, 907 | 1.83–1.89(4H, m), 2.47–2.56 (2H, m), 2.80–2.88(1H, m), 2.92(1H, m), 3.03(1H, m), 3.19(1H, dd), 3.30(1H, dd), 3.38(1H, dd), 6.94(2H, d), 6.99(2H, d), 7.07(1H, t), 7.18(2H, d), 7.31(2H, t), 7.38(1H, t), 7.46(1H, d), 7.61(1H, t), 7.77(1H, d) | $C_{21}H_{20}ClNO_2$ (hydrochloride)<br>C H N<br>Calcd; 74.36 6.24 3.34<br>Found; 74.10 6.22 3.35 |
| 72 | 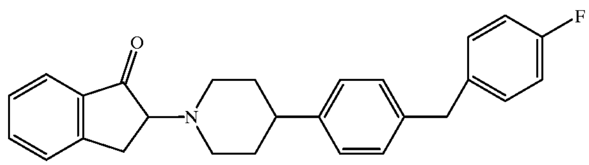 | Pale yellow crystals (hydrochloride) 175–177° C. (methanol/ ether) | (KBr) (hydrochloride) 3476, 2925, 1720, 1607, 1508, 1467, 1221, 1158, 811, 761 | 1.80–1.88(4H, m), 2.50(2H, dt), 2.81(1H, m), 2.89(1H, m), 3.02(1H, m), 3.18(1H, m), 3.29(1H, dd), 3.77(1H, dd), 3.91(2H, s), 6.95(2H, t), 7.07–7.10(6H, m), 7.37(1H, t), 7.46(1H, d), 7.60(1H, t), 7.76(1H, d) | — |
| 73 | 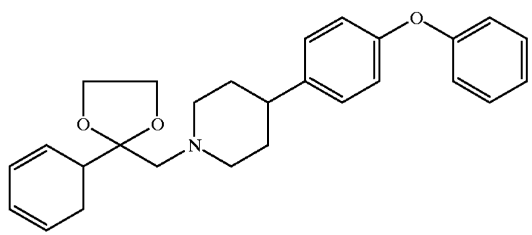 | Colorless crystals (fumarate) 199–200° C. (methanol/ ether) | (KBr) (fumarate) 2450, 2960, 2900, 1686, 1560, 1508, 1490, 1234, 1214, 1026, 707 | 1.69–1.74(4H, m), 2.27(2H, m), 2.41(1H, m), 2.81(2H, s), 3.03(2H, m), 3.84(2H, m), 4.13(2H, m), 6.9–7.45(10H, m), 7.17(2H, d), 7.54(2H, d) | $C_{21}H_{23}NO_7$ (fumarate)<br>C H N<br>Calcd; 70.04 6.26 2.63<br>Found; 69.46 6.29 2.64 |
| 74 | 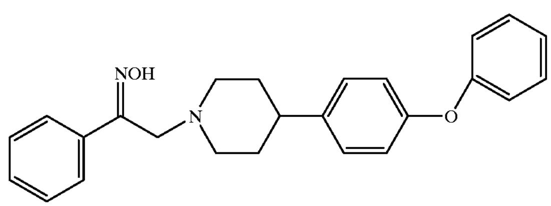 | Foamy substance (hydrochloride) | (KBr) (hydrochloride) 3416, 3060, 1589, 1508, 1489, 1238, 1170, 870, 752, 696 | 1.55–2.10(4H, m), 2.19 and 2.32 (total 2H, both m), 2.54 and 2.58(total 1H, both t), 3.09 and 3.23 (total 2H, both m), 3.43 and 3.85(total 2H, both s), 6.90–8.80(15H, m) | — |

TABLE 1-continued

| Compound no. | Chemical structure | Properties m.p. (recrystall-ization solvent) | IR | ¹H-NMR (CDCl₃) | Elemental analysis |
|---|---|---|---|---|---|
| 75 | (structure: piperidine with cinnamyl N-substituent and 4-(4-methoxybenzyl)phenyl group) | Colorless crystals (hydrochloride) 211–212° C. (methanol/ether) | (KBr) (hydrochloride) 3451, 2928, 2639, 1512, 1451, 1247, 1178, 1032, 749, 694 | 1.75–1.83(4H, m), 2.08(2H, d) 2.47(1H, tt), 3.10(2H, m), 3.19(2H, dd), 3.77(3H, s), 3.88(2H, s), 6.32(1H, dt), 6.53(1H, d), 6.82(2H, dd), 7.02–7.20(6H, m), 7.21(1H, t), 7.30(2H, t), 7.38(2H, d) | $C_{28}H_{32}ClNO$ (hydrochloride) C H N Calcd; 77.49 7.43 3.23 Found; 77.69 7.73 3.21 |
| 76 | (structure: 4-(4-phenoxyphenyl)piperidine with benzofuran-2-ylmethyl N-substituent) | Colorless crystals (hydrochloride) 212–214° C. (methanol/ether) | (KBr) (hydrochloride) 3444, 2928, 2521, 1589, 1508, 1490, 1453, 1241, 1170, 870, 754, 674 | 1.82–1.89(4H, m), 2.21(2H, dt), 2.48(1H, tt), 3.10(2H, m), 3.74(2H, s), 6.60(1H, s), 6.93(2H, d), 6.99(2H, d), 7.07(1H, t), 7.16–7.33(6H, m), 7.50(1H, d), 7.51(1H, d) | $C_{30}H_{30}ClNO_{2}$ (hydrochloride) C H N Calcd; 74.36 6.24 3.34 Found; 74.46 6.27 3.37 |
| 77 | (structure: 4-(4-phenoxyphenyl)piperidine with 2-hydroxy-2-phenylethyl N-substituent) | Colorless crystals (hydrochloride) 196–197° C. (methanol/ether) | (KBr) (hydrochloride) 3302, 2962, 2692, 2362, 1590, 1508, 1490, 1061, 870, 754, 694 | 1.75–2.05(4H, m), 2.23(1H, m), 2.40–2.70(4H, m), 2.98(1H, m), 3.33(1H, dd), 4.79(1H, m), 6.90–7.50(14H, m) | $C_{25}H_{28}ClNO_{2}$ (hydrochloride) C H N Calcd; 73.25 6.88 3.42 Found; 72.99 6.76 3.41 |
| 78 | (structure: 4-(4-phenoxyphenyl)piperidine with 2-hydroxy-2-(4-chlorophenyl)ethyl N-substituent) | Colorless crystals (hydrochloride) 215–216° C. (methanol/ether) | (KBr) (hydrochloride) 3220, 2949, 2638, 1590, 1509, 1490, 1243, 1074, 1016, 872, 819, 758 | 1.72–2.00(4H, m), 2.20(1H, m), 2.39–2.64(4H, m), 2.95(1H, m), 3.28(1H, m), 4.75(1H, dd), 6.98(2H, d), 7.02(2H, d), 7.11(1H, t), 7.21(2H, d), 7.35(6H, m) | $C_{25}H_{27}Cl_{2}NO_{2}$ (hydrochloride) C H N Calcd; 67.57 6.12 3.15 Found; 67.53 6.16 3.14 |

TABLE 1-continued

| Compound no. | Chemical structure | Properties m.p. (recrystallization solvent) | IR | $^1$H-NMR (CDCl$_3$) | Elemental analysis |
|---|---|---|---|---|---|
| 79 | (4-fluorophenoxy-phenyl-piperidine with N-CH2-CH(OH)-phenyl) | Colorless crystals (hydrochloride) 134–135° C. (methanol/ether) | (KBr) (hydrochloride) 3064, 1599, 1504, 1438, 1218, 1155, 962, 813, 761, 702 | 1.70–2.00(4H, m), 2.19(1H, m), 2.42–2.61(4H, m), 2.95(1H, m), 3.32(1H, m), 3.95(2H, s), 4.78(1H, dd), 7.14(2H, t), 7.16–7.52(11H, m) | C$_{24}$H$_{29}$ClFNO(hydrochloride)<br>C H N<br>Calcd: 73.31 6.86 3.29<br>Found: 72.61 6.73 3.21 |
| 80 | (phenoxy-phenyl-piperidine with N-CH2-CH(OH)-CH2-O-phenyl) | Colorless crystals (hydrochloride) 151–152° C. (methanol/ether) | (KBr) (hydrochloride) 3268, 2657, 1590, 1509, 1490, 1246, 1171, 1050, 755, 693 | 1.65–1.95(4H, m), 2.14(1H, m), 2.43(1H, m), 2.45–2.70(3H, m), 2.98(1H, m), 3.14(1H, m), 4.01(2H, m), 4.12(1H, m), 6.92–6.99(5H, m), 7.01(2H, d), 7.08(1H, t), 7.18(2H, d), 7.25–7.40(4H, m) | C$_{24}$H$_{30}$ClNO$_2$ (hydrochloride)<br>C H N<br>Calcd: 70.98 6.87 3.18<br>Found: 70.90 6.82 3.20 |
| 81 | (4-fluorophenoxy-phenyl-piperidine with N-CH2-CH(OH)-CH2-O-phenyl) | Colorless crystals (hydrochloride) 160–161° C. (methanol/ether) | (KBr) (hydrochloride) 3306, 2930, 2646, 1599, 1508, 1250, 1222, 812, 762, 694 | 1.70–2.00(4H, m), 2.16(1H, m), 2.40–2.76(4H, m), 3.01(1H, m), 3.15(1H, m), 3.95(1H, s), 4.03(1H, m), 4.13(1H, m), 6.90–7.40(13H, m) | C$_{27}$H$_{21}$ClFNO$_2$ (hydrochloride)<br>C H N<br>Calcd: 71.12 6.85 3.07<br>Found: 71.02 6.78 3.16 |
| 82 | (4-fluorobenzyl-phenyl-piperazine with N-CH2-C(=O)-phenyl) | Colorless crystals (dihydrochloride) 130–131° C. (methanol/ether) | (KBr) (dihydrochloride) 2905, 2368, 1703, 1600, 1508, 1448, 1278, 1232, 968, 758, 688 | 2.79(4H, t), 3.26(4H, t), 3.89(4H, s), 6.88(2H, d), 6.97(2H, t), 7.10(2H, d), 7.15(2H, t), 7.49(2H, t), 7.60(1H, t), 8.05(2H, d) | C$_{26}$H$_{27}$Cl$_2$FN$_2$O (hydrochloride)<br>C H N<br>Calcd: 65.08 5.90 6.07<br>Found: 65.72 5.95 6.16 |

The anti-veratrizine action of the above synthetic compounds, the T-type $Ca^{2+}$ channel inhibiting action, the anticonvulsant action, the dopamine $D_2$ receptor blocking action, and the $LD_{50}$ were evaluated by the following methods. The results are shown in Table 2, Table 3, Table 4, Table 5, and Table 6.

Veratridine-induced Sodium Channel Activity Inhibiting Action

The membrane potential of the synaptosomes prepared from the brain membrane of Wistar rats (male, 10 to 12 weeks old) was measured by the method of Aiuchi et al. [T. Aiuchi et al: Biochimi. Biophys. Acta. 771, 228 (19854)] using a membrane potential sensitive fluorescent dye Rhodamine 6G to evaluate the effects of suppression of the compound on the veratridine-inducing depolarization response.

The results are shown in Table 2.

TABLE 2

| Compound no. | Antiveratridine action (inhibiting rate %) (0.1 μm of compound) |
|---|---|
| 18 | 16 |
| 19 | 26.1 |
| 21 | 20.3 |
| 26 | 36.5 |
| 28 | 38 |
| 29 | 9.9 |
| 32 | 33.3 |
| 41 | 20.8 |
| 46 | 11.7 |
| 47 | 22.9 |
| 48 | 20.5 |
| 49 | 17.3 |
| 56 | 18.4 |
| 57 | 25 |
| 58 | 33.9 |
| 62 | 23.9 |
| 63 | 31.1 |
| 64 | 34.5 |
| 65 | 38.7 |
| 66 | 19.6 |
| 67 | 15 |
| 68 | 38.9 |
| 69 | 11.2 |
| 73 | 16.1 |
| 74 | 14.6 |
| 75 | 55.2 |
| 77 | 31.1 |
| 78 | 44.4 |
| 79 | 37.1 |
| 80 | 49.7 |
| 81 | 24.1 |
| 82 | 16.9 |

T-Type Calcium Channel Inhibiting Action

The hippocampal CA1 pyramidal cells were isolated from Wistar rats (female, 1 week old) in accordance with the method of Takahashi et al. [K. Takahashi et al.; J. Pharmacol. Exp. Ther., 256, 169 (1991)] and the T-type calcium current under conditions of a fixed membrane potential was measured using the whole-cell configuration of the pach clamp technique. The effects of the compounds were evaluated from the rate of suppression of the peak current after one minute of application using the concentration clamp method.

The results are shown in Table 3.

TABLE 3

| Compound no. | T-type $Ca^{2+}$ channel inhibiting action $IC_{50}$ (μM) |
|---|---|
| 21 | 0.8 |
| 26 | 2.8 |
| 32 | 0.6 |
| 47 | 2.7 |
| 50 | 4.2 |
| 73 | 4.6 |
| 75 | 1.4 |
| 79 | 3.1 |
| 80 | 1.9 |

Audiogenic Seizure Suppressing Action

The audiogenic seizure suppressing action of the compounds was evaluated by the method of Sarro et al. [G. B. De Sarro et al.; Br. J. Pharmacol., 93, 247 (1988)]. That is, DBA/2N mice (male, 3 weeks) were administered with the compound dissolved in 10% 2-hydroxypropyl-β-cyclodextrin intraperitoneally. After 20 minutes, a supersonic washer was used to apply audio stimulus of at least 90 dB for one minute. The wild running (WR), clonic seizures (clonus), tonic seizures (tonus), and respiratory arrest (RA) were evaluated. The seizure suppressing action was evaluated from the rate or suppression of the average value of the seizure score found from 0=no response, 1=WR, 2=clonus, 3=tonus, and 4=RA.

The results are shown in Table 4.

TABLE 4

| Compound no. | Antiseizure action (suppression rate %) (compound 10 mg/kg, i.p.) |
|---|---|
| 18 | 27.9 |
| 19 | 53.6 |
| 21 | 77.3 |
| 22 | 85.7 |
| 24 | 49.1 |
| 25 | 72 |
| 26 | 78 |
| 27 | 34 |
| 28 | 56.9 |
| 29 | 66.2 |
| 31 | 48 |
| 32 | 94 |
| 34 | 34 |
| 41 | 42.7 |
| 42 | 60 |
| 46 | 27.9 |
| 47 | 64.1 |
| 48 | 53.6 |
| 49 | 60 |
| 50 | 72 |
| 51 | 71.4 |
| 52 | 20 |
| 55 | 62 |
| 56 | 50 |
| 58 | 66 |
| 62 | 44 |
| 63 | 76 |
| 64 | 94 |
| 65 | 72 |
| 66 | 39.2 |
| 67 | 37 |
| 69 | 64.7 |
| 70 | 73.9 |
| 71 | 32 |
| 73 | 52.2 |
| 74 | 44.4 |
| 75 | 99 |
| 77 | 85.7 |
| 78 | 66 |

TABLE 4-continued

| Compound no. | Antiseizure action (suppression rate %) (compound 10 mg/kg, i.p.) |
|---|---|
| 79 | 79.8 |
| 80 | 66.3 |
| 81 | 61 |
| 82 | 71.9 |

Dopamine $D_2$ Receptor Blocking Action

57 μl of the membrane fraction prepared from the striatum of Wister male rats (6 weeks old) was incubated in a buffer at 25° C. for one hour along with the compound and 1.0 nM [$^3$H] raclopride. A GF/C glass filter (0.1% polyethylene imine treatment) was used for separation of the B and F, then the radioactivity was measured by a beta plate and the effect of the compound was evaluated.

The results are shown in Table 5.

TABLE 5

| Compound no. | Dopamine $D_2$ receptor blocking action $IC_{50}$ (nM) |
|---|---|
| 21 | 2680 |
| 26 | 3370 |
| 32 | 3380 |
| 47 | 3960 |
| 49 | 987 |
| Flunarizine | 228 |

Acute Toxicity Test

Medicine was intravenously administered to ddY mice (male, 6 weeks old). The 50 percent lethal dosage $LD_{50}$ of the acute toxicity was calculated by an ordinary method from the death rate up to 24 hours after administration.

The results are shown in Table 6.

TABLE 6

| Compound no. | $LD_{50}$ (mg/kg, i.v.) |
|---|---|
| 21 | 40.9 |
| 26 | 32.9 |
| 32 | 32.9 |
| 47 | 43.2 |

As explained above, the present invention can provide medicaments for the alleviation or treatment of symptoms based on ischemic diseases and symptoms derived from seizures, epilepsy, and migraine which have a powerful action in suppressing cytotoxic $Ca^{2+}$ overload and which are free from side effects.

We claim:

1. A pharmaceutical composition of matter for the alleviation or treatment of symptoms based on ischemic diseases or symptoms derived from seizures, epilepsy and migraine headaches comprising in an amount effective for alleviating or treating said symptoms a compound having the formula (I) or its pharmaceutically acceptable salt:

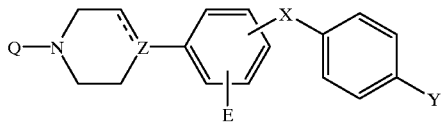
(I)

wherein, Q represents a group having the formula:

R—A—B— in which R represents a hydrogen atom, a substituted or unsubstituted phenyl group, a substituted or unsubstituted phenoxy group, or a substituted or unsubstituted benzoyl group, A represents a connecting bond, a cycloalkylene group, an alkenylene group which may be substituted by a lower alkyl group, a dialkoxymethylene group, or a hydroxyiminomethylene group, and B represents an alkylene group which may be substituted by a hydroxyl group or an alkoxy group;

a group having the formula:

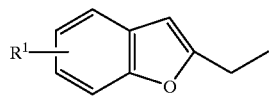

in which $R^1$ represents a hydrogen atom, a halogen atom, an alkyl group which may be substituted by a halogen atom, an alkoxy group, or an hydroxyl group; or a group having the formula:

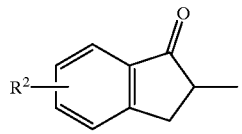

in which $R^2$ represents a hydrogen atom, a halogen atom, an alkyl group which may be substituted by a halogen atom, an alkoxyl group, or a hydroxyl group;

X represents an oxygen atom or a methylene group, the substitution of X for the benzene ring being in a para position, E and Y may be the same or different from each other and represent a hydrogen atom, a hydroxyl group, a halogen atom, an alkoxy group, or an alkyl group which may be substituted by a halogen atom, wherein the dotted line shows the presence or absence of a bond, when said dotted line shows the presence of a bond, further wherein Z represents a carbon atom, and when said dotted line shows the absence of a bond, Z represents CH.

2. A pharmaceutical composition of matter for the alleviation or treatment of symptoms based on ischemic diseases or symptoms derived from seizures, epilepsy and migraine headaches as claimed in claim 1, wherein, in the formula (I), Q represents a group having the formula:

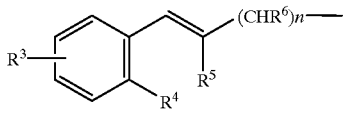

in which $R^3$ represents a hydrogen atom, a halogen atom, an alkyl group which may be substituted by a halogen atom, alkoxy group, or hydroxyl group, $R^4$ and $R^5$ are the same or different from each other and represent a hydrogen atom or a lower alkyl group, $R^6$ represents a hydrogen atom, a hydroxyl group, an alkoxy group, or an alkyl group, and n is an integer of 1 to 6;

$R^4$ and $R^5$ are taken together to represent —O—, $R^6$ is a hydrogen atom, and n is 1.

3. A pharmaceutical composition of matter for the alleviation or treatment of symptoms based on ischemic diseases or symptoms derived from seizures, epilepsy and migraine headaches as claimed in claim 1, wherein, in the formula (I), Q represents a group having the formula:

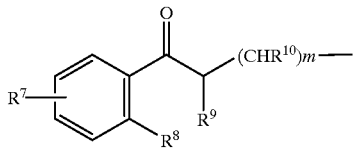

in which $R^7$ represents a hydrogen atom, a halogen atom, an alkyl group which may be substituted by a halogen atom, an alkoxy group, or hydroxyl group, $R^8$ and $R^9$ are the same or different from each other and represent a hydrogen atom or an alkyl group, $R^{10}$ represents a hydrogen atom, a hydroxyl group, an alkoxy group or an alkyl group, and m is an integer from 0 to 6; or $R^8$ and $R^9$ are taken together to represent a methylene group and m is 0.

4. A pharmaceutical composition of matter for the alleviation or treatment of symptoms based on ischemic diseases or symptoms derived from seizures, epilepsy and migraine headaches as claimed in claim 1, wherein, in the formula (I), R represents a substituted or unsubstituted phenyl group and A represents an alkenylene group.

5. A pharmaceutical composition of matter for the alleviation or treatment of symptoms based on ischemic diseases or symptoms derived from seizures, epilepsy and migraine headaches as claimed in claim 1, wherein, in the formula (I), R represents a substituted or unsubstituted benzoyl group and A represents a connecting bond.

6. A pharmaceutical composition of matter for the alleviation or treatment of symptoms based on ischemic diseases or symptoms derived from seizures, epilepsy and migraine headaches as claimed in claim 1, wherein, in the formula (I), R represents a substituted or unsubstituted phenyl group, A represents a connecting bond, and B represents a dimethylene group which is substituted by a hydroxyl group.

7. A pharmaceutical composition of matter for the alleviation or treatment of symptoms based on ischemic diseases or symptoms derived from seizures, epilepsy and migraine headaches as claimed in claim 1, wherein, in the formula (I), R represents a substituted or unsubstituted phenoxy group, A represents a connecting band, and B represents a trimethylene group which is substituted by a hydroxyl group.

8. A method for alleviating or treating symptoms based on ischemic diseases or symptoms derived from seizures, epilepsy and migraine headaches comprising administering in an amount effective for alleviating or treating said symptoms a compound having the formula (I) or its pharmaceutically acceptable salt:

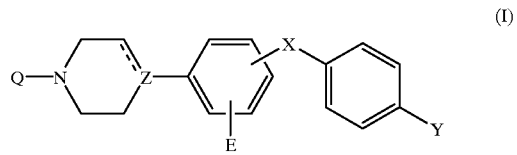

(I)

wherein, Q represents a group having the formula:

in which R represents a hydrogen atom, a substituted or unsubstituted phenyl group, a substituted or unsubstituted phenoxy group, or a substituted or unsubstituted benzoyl group, A represents a connecting bond, a cycloalkylene group, an alkenylene group which may be substituted by a lower alkyl group, a dialkoxymethylene group, or a hydroxyiminomethylene group, and B represents an alkylene group which may be substituted by a hydroxyl group or an alkoxy group;

a group having the formula:

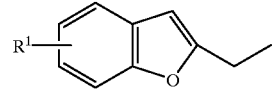

in which $R^1$ represents a hydrogen atom, a halogen atom, an alkyl group which may be substituted by a halogen atom, an alkoxy group, or an hydroxyl group; or a group having the formula:

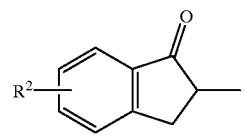

in which $R^2$ represents a hydrogen atom, a halogen atom, an alkyl group which may be substituted by a halogen atom, an alkoxyl group, or a hydroxyl group;

X represents an oxygen atom or a methylene group, the substitution of X for the benzene ring being in an ortho, meta, or para position, E and Y may be the same or different from each other and represent a hydrogen atom, a hydroxyl group, a halogen atom, an alkoxy group, or an alkyl group which may be substituted by a halogen atom, wherein the dotted line shows the presence or absence of a bond, when said dotted line shows the presence of a bond, further wherein Z represents a carbon atom, and when said dotted line shows the absence of a bond, Z represents CH.

9. A $Ca^{2+}$ overload suppressant composition comprising a compound of the formula (I) or its pharmaceutically acceptable salt:

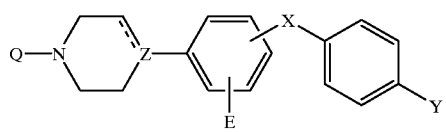
(I)

wherein, Q represents a group having the formula:

R—A—B— in which R represents a hydrogen atom, a substituted or unsubstituted phenyl group, a substituted or unsubstituted phenoxy group, or a substituted or unsubstituted benzoyl group, A represents a connecting bond, a cycloalkylene group, an alkenylene group which may be substituted by a lower alkyl group, a dialkoxymethylene group, or a hydroxyiminomethylene group, and B represents an alkylene group which may be substituted by a hydroxyl group or an alkoxy group;

a group having the formula:

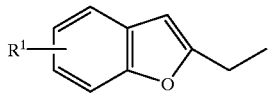

in which $R^1$ represents a hydrogen atom, a halogen atom, an alkyl group which may be substituted by a halogen atom, an alkoxy group, or an hydroxyl group; or a group having the formula:

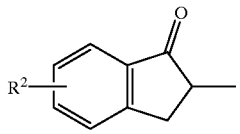

in which $R^2$ represents a hydrogen atom, a halogen atom, an alkyl group which may be substituted by a halogen atom, an alkoxyl group, or a hydroxyl group;

X represents an oxygen atom or a methylene group, the substitution of X for the benzene ring being in an ortho, meta, or para position, E and Y may be the same or different from each other and represent a hydrogen atom, a hydroxyl group, a halogen atom, an alkoxy group, or an alkyl group which may be substituted by a halogen atom, wherein the dotted line shows the presence or absence of a bond, further wherein when said dotted line shows the presence of a bond, Z represents a carbon atom, and wherein when said dotted line shows the absence of a bond, Z represents CH;

said compound of the formula (I) being present in an amount effective to suppress a $Ca^{2+}$ overload.

10. A method for suppressing a $Ca^{2+}$ overload in cells damaged by ischemia comprising administering in an amount effective to suppress a $Ca^{2+}$ overload a compound having the formula (I) or its pharmaceutically acceptable salt:

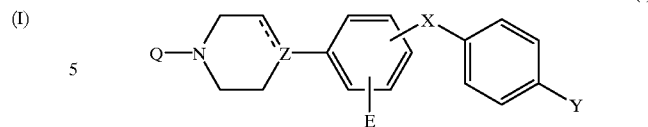
(I)

wherein, Q represents a group having the formula:

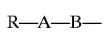

R—A—B— in which R represents a hydrogen atom, a substituted or unsubstituted phenyl group, a substituted or unsubstituted phenoxy group, or a substituted or unsubstituted benzoyl group, A represents a connecting bond, a cycloalkylene group, an alkenylene group which may be substituted by a lower alkyl group, a dialkoxymethylene group, or a hydroxyiminomethylene group, and B represents an alkylene group which may be substituted by a hydroxyl group or an alkoxy group;

a group having the formula:

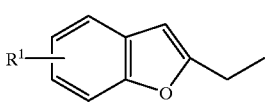

in which $R^1$ represents a hydrogen atom, a halogen atom, an alkyl group which may be substituted by a halogen atom, an alkoxy group, or an hydroxyl group; or a group having the formula:

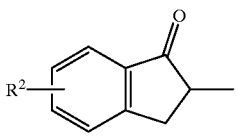

in which $R^2$ represents a hydrogen atom, a halogen atom, an alkyl group which may be substituted by a halogen atom, an alkoxyl group, or a hydroxyl group;

X represents an oxygen atom or a methylene group, the substitution of X for the benzene ring being in an ortho, meta, or para position, E and Y may be the same or different from each other and represent a hydrogen atom, a hydroxyl group, a halogen atom, an alkoxy group, or an alkyl group which may be substituted by a halogen atom, wherein the dotted line shows the presence or absence of a bond, further wherein when said dotted line shows the presence of a bond, Z represents a carbon atom, and wherein when said dotted line shows the absence of a bond, Z represents CH.

11. A compound having the formula (I") or its salts:

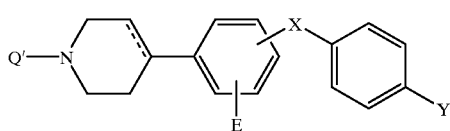

wherein, Q' represents a group having the formula:

in which R' represents a substituted or unsubstituted phenyl group, a substituted or unsubstituted phenoxy group, or a substituted or unsubstituted benzoyl group, A represents a connecting bond, a cycloalkylene group, an alkenylene group which may be substituted by a lower alkyl group, a dialkoxymethylene group, or a hydroxyiminomethylene group, and B represents an alkylene group which may be substituted by a hydroxyl group or an alkoxy group;

a group having the formula:

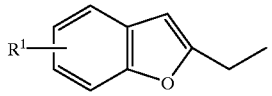

in which $R^1$ represents a hydrogen atom a halogen atom, an alkyl group which may be substituted by a Halogen atom, an alkoxy group, or a hydroxyl group; or a group having the formula:

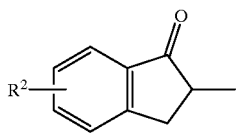

in which $R^2$ represents a hydrogen atom, a halogen atom, an alkyl group which may be substituted by a halogen atom, an alkoxy group, or a hydroxyl group, X represents an oxygen atom or a methylene group, the substitution of X for the benzene ring being in a para position, E and Y may be the same or different from each other and represent a hydrogen atom, a hydroxyl group, a halogen atom, an alkoxy group, or an alkyl group which may be substituted by a halogen atom, the dotted line shows the presence or absence of a bond, and when X is a methylene group, A is a connecting bond and B is an unsubstituted alkylene group, $R^2$ does not represent an unsubstituted phenyl group.

12. A compound or its salt as claimed in claim 11, wherein, in the formula (I"), Q' represents a group having the formula:

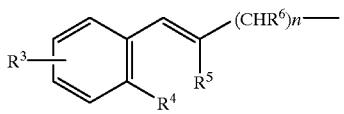

in which $R^3$ represents a hydrogen atom, a halogen atom, an alkyl group which may be substituted by a halogen atom, an alkoxy group, or a hydroxyl group, $R^4$ and $R^5$ are the same or different from each other and represent a hydrogen atom or a lower alkyl group, $R^6$ represents a hydrogen atom, a hydroxyl group, an alkoxy group, or an alkyl group, and n is an integer of 1 to 6, or $R^4$ and $R^5$ are take together to represent —O—, $R^6$ is a hydrogen atom and n is 1.

13. A compound or its salt as claimed in claim 11, wherein, in the formula (I"), Q' represents a group having the formula:

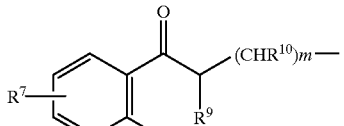

in which $R^7$ represents a hydrogen atom, a halogen atom, an alkyl group which may be substituted by a halogen atom, an alkoxy group, or a hydroxyl group, $R^8$ and $R^9$ are the same or different from each other and represent a hydrogen atom or an alkyl group, $R^{10}$ represents a hydrogen atom, a hydroxyl group, an alkoxy group or an alkyl group, and m is an integer from 0 to 6 or $R^8$ and $R^9$ are take together to represent a methylene group and m is 0.

14. A compound or its salt as claimed in claim 11, wherein, in the formula (I"), R' represents a substituted or unsubstituted phenyl group and A represents an alkenylene group.

15. A compound or its salt as claimed in claim 11, wherein, in the formula (I"), R' represents a substituted or unsubstituted benzoyl group and A represents a connecting bond.

16. A compound or its salt as claimed in claim 11, wherein, in the formula (I"), R' represents a substituted or unsubstituted phenyl group, A represents a connecting bond, and B represents a dimethylene group which is substituted by a hydroxyl group.

17. A compound or its salt as claimed in claim 11, wherein, in the formula (I"), R' represents a substituted or unsubstituted phenoxy group, A represents a connecting bond, and B represents a trimethylene group which is substituted by a hydroxyl group.

18. A pharmaceutical composition comprising a compound having the formula (I") or its pharmaceutically acceptable salt:

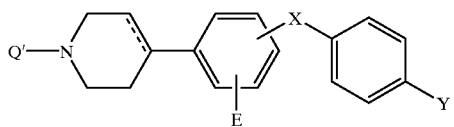

wherein, Q' represents a group having the formula:

in which R' represents a substituted or unsubstituted phenyl group, a substituted or unsubstituted phenoxy group, or a substituted or unsubstituted benzoyl group, A represents a connecting bond, a cycloalkylene group, an alkenylene group which may be substituted by a lower alkyl group, a dialkoxymethylene group, or a, hydroxy-iminomethylene group, and B represents an alkylene group which may be substituted by a hydroxyl group or an alkoxy group;

a group having the formula:

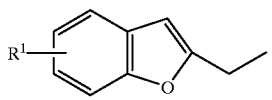

in which $R^1$ represents a hydrogen atom, a halogen atom, an alkyl group which may be substituted by a halogen atom, an alkoxy group, or a hydroxyl group; or a group having the formula:

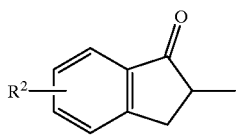

in which $R_2$ represents a hydrogen atom, a halogen atom, an alkyl group which may be substituted by a halogen atom, an alkoxy group, or a hydroxyl group;

X represents an oxygen atom or a methylene group, the substitution of X for the benzene ring being in a para position, E and Y may be the same or different from each other and represent a hydrogen atom, a hydroxyl group, a halogen atom, an alkoxy group, or an alkyl group which may be substituted by a halogen atom, the dotted line shows the presence or absence of a bond and when X is a methylene group, A is a connecting bond and B is an unsubstituted alkylene group, R' does not represent an unsubstituted phenyl group.

19. A pharmaceutical composition as claimed in claim 18, wherein, in the formula (I"), Q' represents a group having the formula:

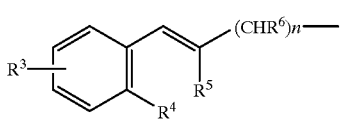

in which $R^3$ represents a hydrogen atom, a halogen atom, an alkyl group which may be substituted by a halogen atom, an alkoxy group, or a hydroxyl group, $R^4$ and $R^5$ are the same or different from each other and represent a hydrogen atom or a lower alkyl group, $R^6$ represents a hydrogen atom, a hydroxyl group, an alkoxy group, or an alkyl group, and n is an integer of 1 to 6 or $R^4$ and $R^5$ are take together to represent —O—, $R^6$ is hydrogen atom and n is 1.

20. A pharmaceutical composition as claimed in claim 18, wherein, in the formula (I"), Q' represents a group having the formula:

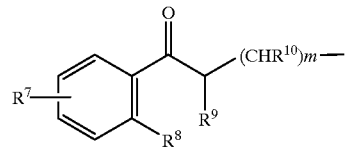

in which $R^7$ represents a hydrogen atom, a halogen atom, an alkyl group which may be substituted by a halogen atom, an alkoxy group, or a hydroxyl group, $R^8$ and $R^9$ are the same or different from each other and represent a hydrogen atom or an alkyl group, $R^{10}$ represents a hydrogen atom, a hydroxyl group, an alkoxy group or an alkyl group, and m is an integer from 0 to 6 or $R^8$ and $R^9$ are take together to represent a methylene group and m is 0.

21. A pharmaceutical composition of matter for the alleviation or treatment of symptoms based on ischemic diseases or symptoms derived from seizures, epilepsy and migraine headaches comprising in an amount effective for alleviating or treating said symptoms a compound having the formula (I") or its pharmaceutically acceptable salt:

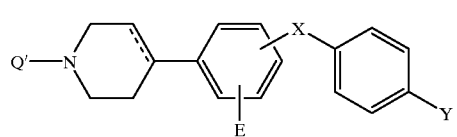

wherein, Q' represents a group having the formula:

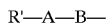

in which R' represents a substituted or unsubstituted phenyl group, a substituted or unsubstituted phenoxy group, or a substituted or unsubstituted benzoyl group, A represents a connecting bond, a cycloalkylene group, an alkenylene group which may be substituted by a lower alkyl group, a dialkoxymethylene group, or a hydroxy-iminomethylene group, and B represents an alkylene group which may be substituted by a hydroxyl group or an alkoxy group;

a group having the formula:

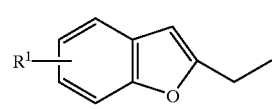

in which $R^1$ represents a hydrogen atom, a halogen atom, an alkyl group which may be substituted by a halogen atom, an alkoxy group, or a hydroxyl group; or a group having the formula:

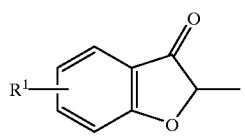

in which $R^2$ represents a hydrogen atom, a halogen atom, an alkyl group which may be substituted by a halogen atom, an alkoxy group, or a hydroxyl group, X represents an oxygen atom or a methylene group, the substitution of X for the benzene ring being in a para position, E and Y may be the same or different from each other and represent a hydrogen atom, a hydroxyl group, a halogen atom, an alkoxy group, or an alkyl group which may be substituted by a halogen atom, the dotted line shows the presence or absence of a bond, and when X is a methylene group, A is a connecting bond and B is an unsubstituted alkylene group, R' does not represent an unsubstituted phenyl group.

22. A $Ca^{2+}$ overload suppressant composition comprising in an amount effective to suppress $Ca^{2+}$ overload a compound having the general formula (I″) or its pharmaceutically acceptable salt:

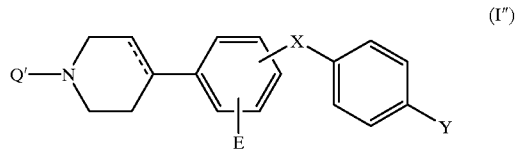

(I″)

wherein, Q' represents a group having the formula:

R'—A—B— in which R' represents a substituted or unsubstituted phenyl group, a substituted or unsubstituted phenoxy group, or substituted or unsubstituted benzoyl group, A represents a connecting bond, a cycloalkylene group, an alkenylene group which may be substituted by a lower alkyl group, a dialkoxymethylene group, or a hydroxyiminomethylene group, and B represents an alkylene group which may be substituted by a hydroxyl group or an alkoxy group;

a group having the formula:

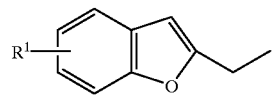

in which $R^1$ represents, a hydrogen atom, a halogen atom, an alkyl group which may be substituted by a halogen atom, an alkoxy group, or a hydroxyl group; or a group having the formula:

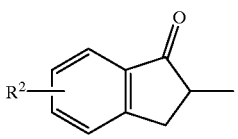

in which $R^2$ represents a hydrogen atom, a halogen atom, an alkyl group which may be substituted by a halogen atom, an alkoxy group, or a hydroxyl group;

X represents an oxygen atom or a methylene group, the substitution of X for the benzene ring being in a para position, E and Y may be the same or different from each other and represent a hydrogen atom, a hydroxyl group, a halogen atom, an alkoxy group, or an alkyl group which may be substituted by a halogen atom, the dotted line shows the presence or absence of a bond, and when X is a methylene group, A is a connecting bond and B is an unsubstituted alkylene group, R' does not represent an unsubstituted phenyl group.

23. A pharmaceutical composition comprising, as an effective ingredient, a compound according to claim 17, or its pharmaceutically acceptable salt.

24. A pharmaceutical composition for the alleviation or treatment of symptoms based on ischemic diseases or symptoms derived from seizures, epilepsy and migraine comprising a compound according to claim 17, or its pharmaceutically acceptable salt, in an amount effective for alleviation or treatment of symptoms based on ischemic diseases or symptoms derived from seizures, epilepsy and migraine.

25. A $Ca^{2+}$ overload suppressant composition comprising, as an effective ingredient, a compound according to claim 17, or its pharmaceutically acceptable salt.

26. A method for alleviation or treatment of symptoms based on ischemic diseases or symptoms derived from seizures, epilepsy and migraine comprising applying to a patient a compound of the formula (I″) according to claim 11, or its pharmaceutically acceptable salt, in an amount effective for alleviation or treatment of symptoms based on ischemic diseases or symptoms derived from seizures, epilepsy and migraine.

27. A method for preventing neuronal cell death or cardiovascular cell injury in ischemia by suppressing a $Ca^{2+}$ overload comprising administering in an amount effective to suppress a $Ca^{2+}$ overload a compound having the formula (I) or its pharmaceutically acceptable salt:

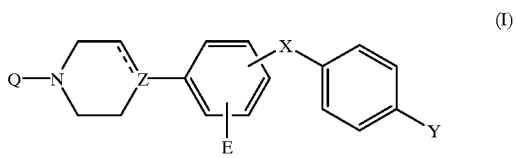

(I)

wherein, Q represents a group having the formula:

R—A—B—, in which

R represents a hydrogen atom, a substituted or unsubstituted phenyl group, a substituted or unsubstituted phenoxy group, or a substituted or unsubstituted benzoyl group, A represents a connecting bond, a cycloalkylene group, an alkenylene group which may be substituted by a lower alkyl group, a dialkoxymethylene group, or a hydroxyiminomethylene group, and B represents an alkylene group which may be substituted by a hydroxyl group or an alkoxy group;

a group having the formula:

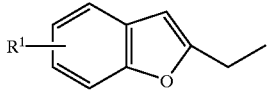

in which $R^1$ represents a hydrogen atom, a halogen atom, an alkyl group which may be substituted by a halogen, an alkoxy group, or a hydroxyl group; or a group having the formula:

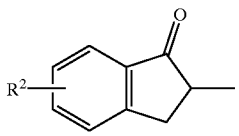

in which $R^2$ represents a hydrogen atom, a halogen atom, an alkyl group which may be substituted by a halogen atom, an alkoxy group, or a hydroxyl group;

X represents an oxygen atom or methylene group, the substitution of X for the benzene ring being in a para position, E and Y may be the same or different from each other and represent a hydrogen atom, a hydroxyl group, a halogen atom, an alkoxy group, or an alkyl group which may be substituted by a halogen atom, wherein the dotted line shows the presence or absence of a bond, when said dotted line shows the presence of a bond, further wherein Z represents a carbon atom, and when said dotted line shows the absence of a bond, Z represents CH.

28. A method for protecting neuronal cells or cardiovascular cells from injury in ischemia by suppressing a $Ca^{2+}$ overload comprising administering in an amount effective to suppress a $Ca^{2+}$ overload a compound having the formula (I) or its pharmaceutically acceptable salt:

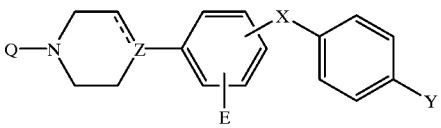

(I)

wherein, Q represents a group having the formula:

R—A—B—,

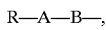

in which

R represents a hydrogen atom, a substituted or unsubstituted phenyl group, a substituted or unsubstituted phenoxy group, or a substituted or unsubstituted benzoyl group, A represents a connecting bond, a cycloalkylene group, an alkenylene group which may be substituted by a lower alkyl group, a dialkoxymethylene group, or a hydroxyiminomethylene group, and B represents an alkylene group which may be substituted by a hydroxyl group or an alkoxy group;

a group having the formula:

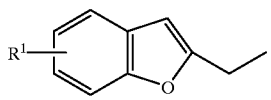

in which $R^1$ represents a hydrogen atom, a halogen atom, an alkyl group which may be substituted by a halogen, an alkoxy group, or a hydroxyl group; or a group having the formula:

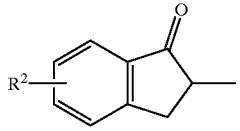

in which $R^2$ represents a hydrogen atom, a halogen atom, an alkyl group which may be substituted by a halogen atom, an alkoxy group, or a hydroxyl group;

X represents an oxygen atom or methylene group, the substitution of X for the benzene ring being in a para position, E and Y may be the same or different from each other and represent a hydrogen atom, a hydroxyl group, a halogen atom, an alkoxy group, or an alkyl group which may be substituted by a halogen atom, wherein the dotted line shows the presence or absence of a bond, when said dotted line shows the presence of a bond, further wherein Z represents a carbon atom, and when said dotted line shows the absence of a bond, Z represents CH.

29. A compound having the general formula (IIa) or its salt:

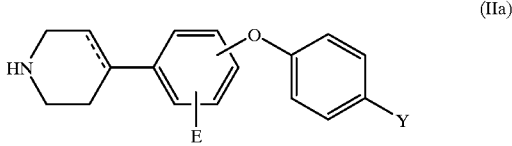

(IIa)

wherein, E and Y may be the same or different from each other and represent a hydrogen atom, a hydroxyl group, a halogen atom, an alkoxy group, or an alkyl group which may be substituted by a halogen atom, the dotted line shows the presence or absence of a bond, and the substitution of the benzene ring bonding with the piperidine ring or the tetrahydropyridine ring and the group —$OC_6H_4Y$ is in a para position.

30. A compound having the formula (IIb) or its salt:

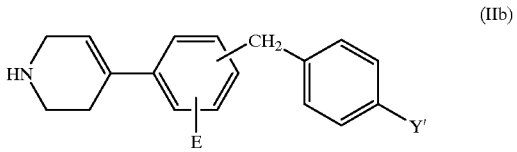

(IIb)

wherein, E represents a hydrogen atom, a hydroxyl group, a halogen atom, an alkoxy group, or an alkyl group which may be substituted by a halogen atom, Y' represents a hydroxyl group, a halogen atom, an alkoxy group, or an alkyl group which may be substituted by a halogen atom, and the substitution of the benzene ring bonding with the tetrahydropyridine ring and group —CH$_2$C$_6$H$_4$Y' is in a para position.

31. A compound having the formula (IIc) or its salt:

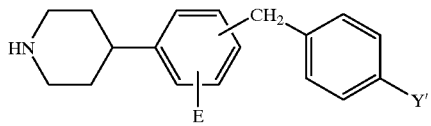

(IIc)

wherein, E represents a hydrogen atom, a hydroxyl group, a halogen atom, an alkoxy group, or an alkyl group which may be substituted by a halogen atom, Y' represents a hydroxyl group, a halogen atom, an alkoxy group, or an alkyl group which may be substituted by a halogen atom, and the substitution of the benzene ring bonding with the piperidine ring and the group —CH$_2$C$_6$H$_4$Y' is in a para position.

* * * * *